(12) United States Patent
Petkovich et al.

(10) Patent No.: US 6,861,238 B1
(45) Date of Patent: Mar. 1, 2005

(54) RETINOID METABOLIZING PROTEIN

(75) Inventors: P. Martin Petkovich, Kingston (CA); Jay A. White, Kingston (CA); Barbara R. Beckett, Kingston (CA); Glenville Jones, Kingston (CA)

(73) Assignee: Queen's University at Kingston, Kingston (CA)

( * ) Notice: Subject to any disclaimer, the term of this patent is extended or adjusted under 35 U.S.C. 154(b) by 101 days.

(21) Appl. No.: 09/668,482

(22) Filed: Sep. 25, 2000

Related U.S. Application Data

(60) Division of application No. 08/882,164, filed on Jun. 25, 1997, now Pat. No. 6,306,624, which is a continuation-in-part of application No. PCT/CA97/00440, filed on Jun. 23, 1997, and a continuation-in-part of application No. 08/724,466, filed on Oct. 1, 1996, now Pat. No. 6,063,606, which is a continuation-in-part of application No. 08/667,546, filed on Jun. 21, 1996, now abandoned.

(51) Int. Cl.$^7$ ............................ C12N 9/02; C12N 1/21; C12N 5/06; C07H 21/04
(52) U.S. Cl. .................... 435/189; 435/252.3; 435/325; 536/23.2
(58) Field of Search ............................ 435/189, 252.3, 435/325, 191; 536/23.2

(56) References Cited

FOREIGN PATENT DOCUMENTS

| EP | 0 721 984 A1 | 7/1996 |
|---|---|---|
| WO | WO92/16658 | 10/1992 |
| WO | WO93/22331 | 11/1993 |
| WO | WO96/23080 | 8/1996 |

OTHER PUBLICATIONS

Vetter et al. (1992) Plant Physiology, vol. 100, pp. 998–1007.*
Shen et al. (1993) Proc. Natl. Acad. Sci. USA, vol. 90, pp. 11483–11487.*
Elizabeth A. Duell, Sewon Kang, and John J. Voorhees, Retinoic Acid Iso mers Applied to Human Skin in Vivo Each Induce a 4–Hydroxylase That Inactivates Only Trans Retinoic Acid. The Journal of Investigative Dermatology—pp. 316–320—vol. 106 No. 2, (1996).
Adamson P.C. et al., "Time Course of Induction of Metabolism . . . " Cancer Research, 53: 472–476 (1993).
Boylan J.F. et al., "Targeted Disruption of Retinoic Acid Receptor . . . " Molecular and Cellular Biology, 15: 2, 843–851 (Feb. 1995).
De Coster R. et al., "Experimental Studies with Liarozole . . . " J. Steroid Molec. Biol., 43: 1–3, 197–201 (1992).
Fiorella, P.D. et al., "Microsomal Retinoic Acid Metabolism . . . " Journal of Biological Chemistry, 269: 14, 10538–10544 (Apr. 1994).
Denison, M.S. et al., "Xenobiotic–inducible transcription of cytochrome P450 genes", J. Biol. Chem., 270: 18175–18178 (1995).

Duell, E.A. et al., "Human skin levels of retinoic acid and cytochrome P–450–derived 4–hydroxyretinoic acid after topical application of retinoic acid in vivo compared to concentrations required to stimulate retinoic acid receptor–mediated transcription in vitro", J. Clin. Invest., 90: 1269–1274 (1992).
Duell, E.A. et al., "All–trans, 9–cis and 13–cis retinoic acid each induce a cytochrome P450 4–retinoic acid hydroxylase which causes all–trans but not 9–cis or 13–cis retinoic acid to self–metabolize", SID Abstracts, J Investigative Dermatology 102: 641 (1994).
Frolik, C.A., et al., "Isolation and identification of 4–hydroxy– and 4–oxoretinoic acid. In vitro metabolites of all–trans–retinoic acid in hamster trachea and liver", Biochemistry, 18: 2092–2097 (1979).
Muindi, J.R.F. et al., "Clinical pharmacology of all–trans retinoic acid", Leukemia, 8: S16–S21 (1994).
Roberts, A.B. et al., "In vitro metabolism of retinoic acid in hamster intestine and liver", J. Biol. Chem., 254: 6296–6302 (1979).
Roberts, A.B. et al., "Retinoid–dependent induction of the in vivo and in vitro metabolism of retinoic acid in tissues of the vitamin A–deficient hamster", J. Biol. Chem., 254: 6303–6309 (1979).
Takatsuka, J. et al., "Retinoic acid metabolism and inhibition of cell proliferation: an unexpected liaison", Cancer Res., 56: 675–678 (1996).
Van Wauwe, J.P., et al., "Ketoconazole inhibits the in vitro and in vivo metabolism of all–trans–retinoic acid", J. Pharm. Exp. Ther. 245: 718–722 (1988).
Van Wauwe, J.P. et al., "Effects of cytochrome P–450 inhibitors on the in vivo metabolism of all–trans–retinoic acid in rats", J. Pharm. Exp. Ther. 252: 365–369 (1990).
Van Wauwe, J.P. et al., "Liarozole, an inhibitor of retinoic acid metabolism, exerts retinoid–mimetic effects in vivo", J. Pharm. Exp. Ther. 261: 773–779 (1992).
Williams, J.B., et al., "Inhibition of retinoic acid metabolism by imidazole antimycotics in F9 embryonal carcinoma cells", Biochem. Pharm. 36: 1386–1388 (1987).
Wouters, W., et al., "Effects of liarozole, a new antitumoral compound, on retinoic acid–induced inhibition of cell growth and on retinoic acid metabolism in MCF–7 human breast cancer cells", Cancer Res. 52: 2841–2846 (1992).
Achkar, C.C. et al., "4–Oxoretinol, a new natural ligand and transactivator of the retinoic acid receptors", Proc. Natl. Acad. Sci. USA, 93: 4879–4884 (1996).

(List continued on next page.)

Primary Examiner—Elizabeth Slobodyansky

(57) ABSTRACT

Amino acid sequences and corresponding nucleic acid sequence of retinoid metabolizing protein found in human, mouse and zebrafish are described, as well as methods of using same.

11 Claims, 20 Drawing Sheets

(1 of 20 Drawing Sheet(s) Filed in Color)

OTHER PUBLICATIONS

Akimenko, M.-A. et al., "Anterior duplication of the Sonic hedgehog expression pattern in the pectoral fin buds of zebrafish treated with retinoic acid", Dev. Biol., 170: 243–247 (1995).

Akimenko, M.-A. et al., "Differential induction of four msx homeobox genes during fin development and regeneration in zebrafish", Development, 121: 347–357 (1995).

Akiyoshi–Shibata, M. et al., "Further oxidatization of hydroxycalcidiol by calcidiol 24–hydroxylase. A study with the mature enzyme expressed in *Escherichia coli*", Eur. J. Biochem., 224: 335–343 (1994).

Blumberg, B. et al., "Novel retinoic acid receptor ligands in Xenopus embryos", Proc. Natl. Acad. Sci. USA, 93: 4873–4878 (1996).

Boyle, A.L. et al., "Rapid physical mapping of cloned DNA on banded mouse chromosomes by fluorescence in situ hybridization", Genomics 12: 106–115 (1992).

Castonguay, A. et al., "Expression of xenobiotic–metabolizing enzymes in cultured rat tracheal epithelial cells", Environ. Health Perspect. 103: 254–258 (1995).

Chambon, P., "The molecular and genetic dissection of the retinoid signaling pathway", Recent Progress in Hormone Research, 50: 317–332 (1995).

Chen, K.-S., et al., "Cloning of the human 1 α,25–dihydroxyvitamin D–3 24–hydroxylase gene promoter and identification of two vitamin D–responsive elements", Biochim. Biophys. Acta, 1263: 1–9 (1995).

Costaridis, P. et al., "Endogenous retinoids in the zebrafish embryo and adult", Dev. Dynamics, 205: 41–51 (1996).

Creech Kraft, J. et al., "Temporal distribution, localization and metabolism of all–trans–retinol, didehydroretinol and all–trans–retinal during Xenopus development", Biochem J., 301: 111–119 (1994).

Fiorella, P.D. et al., "Expression of cellular retinoic acid–binding protein (Type II) in *Escherichia coli*", J. Biol. Chem., 268: 21545–21552 (1993).

Green, S., et al., "versatile in vivo and in vitro eukaryotic expression sector for protein engineering", Nucl. Acids Res., 16: 369 (1988).

Gubler, M.L. et al., "Metabolism of Retinoic Acid and Retinol . . . " Methods in Enzymology, 189, 525–530 (1990).

Guengerich, F.P., "Reactions and significance of cytochrome P–450 enzymes", J. Biol. Chem., 266: 10019–10022 (1991).

Han, I.S. et al., "Highly specific cytochrome P450–like enzymes for all–trans–retinoic acid in T47D human breast cancer cells", J. Clin. Endocr. Metab. 81: 2069–2075 (1996).

Heng, H.H.Q. et al., "Modes of DAPI banding and simultaneous in situ hybridization", Chromosoma, 102: 325–332 (1993).

Hillier, et al., Accession R51129, EST–STS, EST–STS–Two databases (May, 1995).

Jones, B.B. et al., "New retinoid X receptor subtypes in zebra fish (Danio rerio) differentially modulate transcription and do not bind 9–cis retinoic acid", Mol. Cell. Biol., 15: 5226–5234 (1995).

Lammer, E.J. et al., "Retinoic acid embryopathy", N. Engl. J. Med., 313: 837–841 (1985).

Leo, M.A. et al., "Metabolism of retinol and retinoic acid by human liver cytochrome P450IIC8", Arch. Biochem. Biophys. 269: 305–312 (1989).

Leo, M.A. et al., "Retinoic acid metabolism by a system reconstituted with cytochrome P–450", Arch. Biochem. Biophys. 234: 305–312 (1984).

Liang, P. et al., "Differential display of eukaryotic messenger RNA by means of the polymerase chain reaction", Science, 257: 967–971 (1992).

Lichter, P. et al., "High–resolution mapping of human chromosome 11 by in situ hybridization with cosmid clones", Science, 247: 64–69 (1990).

Maden, M. et al., "Retinoic acid and development of the central nervous system", BioEssays, 14: 431–438 (1992).

Makin, G. et al., "Target cell metabolism of 1,25–dihydroxyvitamin D3 to calcitroic acid", Biochem. J., 262: 173–180 (1989).

Mangelsdorf, D.J. et al., "The RXR heterodimers and orphan receptors", Cell 83: 841–850 (1995).

Martini, R. et al., "Participation of P450 3A enzymes in rat hepatic microsomal retinoic acid 4–hydroxylation", Arch. Biochem. Biophys. 303: 57–66 (1993).

Martini, R. et al., "Retinal dehydrogenation and retinoic . . . " Biochemical Pharmacology, 47, No. 5, 905–909, 1994.

Marikar, Y. et al., "Regulation, properties, and solubilization of a unique cytochrome P–450 that specifically metabolizes all–trans retinoic acid to less active 4–hydroxy retinoic acid in human keratinocyte HACAT cells", Abstract, J. Invest. Dermatol. 106(4): 807 (1996).

Monia, B.P. et al., "Antitumor activity of a phosphorothioate antisense oligodeoxynucleotide targeted against C–raf kinase", Nature Med., 2: 668–675 (1996).

Morriss–Kay, G., "Retinoic acid and craniofacial development: molecules and morphogenesis", BioEssays, 15: 9–15 (1993).

Muindi, J.R.F. et al., "Clinical pharmacology of oral all–trans retinoic acid in patients with acute promyelocytic leukemia", Cancer Res., 52: 2138–2142 (1992).

Muindi, J.R.F., et al., "Clinical pharmacology of all–trans retinoic Acid" Liekemis 8:1807–1812 (1994).

Muindi, J.F. et al., "Lipid Hydroperoxides Greatly Increase the Rate . . . " Cancer Research, 53, 1226–1229 (Mar. 1993).

Murtha, M.L. et al., "Detection of homeobox genes in development and evolution", Proc. Natl. Acad. Sci. USA, 88: 10711–10715 (1991).

Napoli, J.L. et al., "The biosynthesis of retinoic acid from retinol by rat tissues in vitro", Arch. Biochem. Biophys., 255: 95–101 (1987).

Nelson, D.R. et al., "The P450 superfamily: update on new sequences, gene mapping, accession Numbers, early trivial names of enzymes, and nomenclature", DNA and Cell Biol., 12: 1–51 (1993).

Ogura, T. et al., "A retinoic acid–triggered cascade of HOXB1 gene activation", Proc. Natl. Acad. Sci. USA 92: 387–391(1995).

Ohyama, Y. et al., "Identification of a vitamin D–responsive element in the 5'–flanking region of the rat 25–hydroxyvitamin D3 24–hydroxylase gene", J. Biol. Chem., 269: 10545–10550 (1994).

Pijnappel, W.W.M. et al., "The retinoid ligand 4–oxo–retinoic acid is a highly active modulator of positional specification", Nature, 366: 340–344 (1993).

Raner, G.M. et al., "Metabolism of all–trans, 9–cis, and 13–cis isomers of retinal by purified isozymes of microsomal cytochrome P450 and mechanism–based inhibition of retinoid oxidation by citral", Mol. Pharmacol. 49: 515–522 (1996).

Reddy, A.P. et al., "Characterization and purification of human retinoic acid receptor–γ1 overexpressed in the baculovirus–insect cell system", Biochem J., 287: 833–840 (1992).

Thaller, C., et al., "Isolation of 3,4–didehydroretinoic acid, a novel morphogenetic signal in the chick wing bud", Nature, 345: 815–819 (1990).

Tomita, S., et al., "Characteristic properties of a retinoic acid synthetic cytochrome P–450 purified from liver microsomes of 3–methylcholanthrene–induced rats", Biochim. Biophys. Acta 1290: 273–281 (1996).

White, J.A., et al., "A zebrafish retinoic acid receptor expressed in the regenerating caudal fin", Development, 120: 1861–1872 (1994).

White, J.A., et al., "Identification of the retinoic acid–inducible all–trans–retinoic acid 4–hydroxylase", J. Biol. Chem. 271: 29922–29927 (1996).

Windhorst, D.B., "The use of isotretinoin in disorders of keratinization", J. Am. Acad. Dermatol. 6: 708–709 (1982).

Zierold, C. et al., "Two vitamin D response elements function in the rat I,25–dihydroxyvitamin D 24–hydroxylase promoter", J. Biol. Chem., 270: 1675–1678 (1995).

George et al., (1988) Macromolecular Sequencing and Synthesis, Selected Methods and Applications, pp. 127–149. Alan R. Liss, Inc.

Nelson, DD.R., "A second CUP26 P450 in humans and zebrafish: CYP26B1", *Archies of Biochemistry and Biophysics.* 371(2): 345–347 (1999).

* cited by examiner

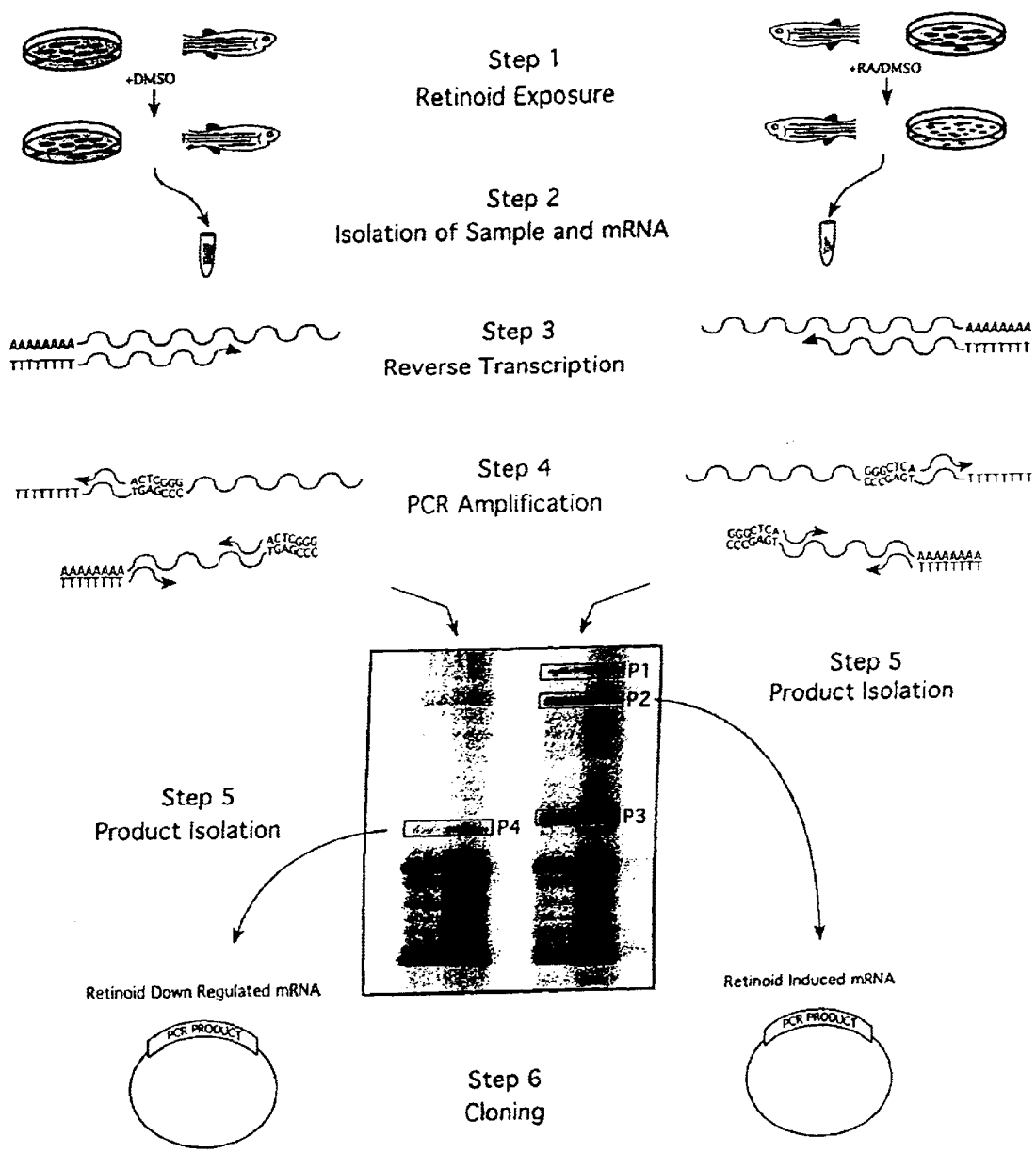

Fig. 1. Schematic representation of the steps involved in the isolation of retinoid-regulated genes using the differential display technique. The cloned products isolated in step 6 can then be used for sequencing, Northern blotting or screening of cDNA libraries. P1, P2 and P3 correspond to fragments from RA induced mRNAs. P4 represents a PCR product from an mRNA which is down-regulated.

C

```
MetGlyLeuTyrThrLeuMetValThrPheLeuCysThrIleValLeuProValLeuLeu    20
PheLeuAlaAlaValLysLeuTrpGluMetLeuMetIleArgArgValAspProAsnCys    40
ArgSerProLeuProProGlyThrMetGlyLeuProPheIleGlyGluThrLeuGlnLeu    60
IleLeuGlnArgArgLysPheLeuArgMetLysArgGlnLysTyrGlyCysIleTyrLys    80
ThrHisLeuPheGlyAsnProThrValArgValMetGlyAlaAspAsnValArgGlnIle   100
LeuLeuGlyGluHisLysLeuValSerValGlnTrpProAlaSerValArgThrIleLeu   120
GlySerAspThrLeuSerAsnValHisGlyValGlnHisLysAsnLysLysLysAlaIle   140
MetArgAlaPheSerArgAspAlaLeuGlnHisTyrIleProValIleGlnGlnGluVal   160
LysSerAlaIleGlnGluTrpLeuGlnLysAspSerCysValLeuValTyrProGluMet   180
LysLysLeuMetPheArgIleAlaMetArgIleLeuLeuGlyPheGluProGluGlnIle   200
LysThrAspGluGlnGluLeuValGluAlaPheGluGluMetIleLysAsnLeuPheSer   220
LeuProIleAspValProPheSerGlyLeuTyrArgGlyLeuArgAlaArgAsnPheIle   240
HisSerLysIleGluGluAsnIleArgLysLysIleGlnAspAspAspAsnGluAsnGlu   260
GlnLysTyrLysAspAlaLeuGlnLeuLeuIleGluAsnSerArgArgSerAspGluPro   280
PheSerLeuGlnAlaMetLysGluAlaAlaThrGluLeuLeuPheGlyGlyHisGluThr   300
ThrAlaSerThrAlaThrSerLeuValMetPheLeuGlyLeuAsnThrGluValValGln   320
LysValArgGluGluValGlnGluLysValGluMetGlyMetTyrThrProGlyLysGly   340
LeuSerMetGluLeuLeuAspGlnLeuLysTyrThrGlyCysValIleLysGluThrLeu   360
ArgIleAsnProProValProGlyGlyPheArgValAlaLeuLysThrPheGluLeuAsn   380
GlyTyrGlnIleProLysGlyTrpAsnValIleTyrSerIleCysAspThrHisAspVal   400
AlaAspValPheProAsnLysGluGluPheGlnProGluArgPheMetSerLysGlyLeu   420
GluAspGlySerArgPheAsnTyrIleProPheGlyGlyGlySerArgMetCysValGly   440
LysGluPheAlaLysValLeuLeuLysIlePheLeuValGluLeuThrGlnHisCysAsn   460
TrpIleLeuSerAsnGlyProProThrMetLysThrGlyProThrIleTyrProValAsp   480
AsnLeuProThrLysPheThrSerTyrValArgAsn                           492
```

B

```
TGCCAGTGGACAATCTCCCTACCAAATTCACTAGTTATGTCCAGAAATTA              50
GCCTAAACCGGAGCCTTTGTACATATGTTTTTATTTTAGATGAACTGTGA             100
TGTATTGGATATTTTCTAATTTGTTTATATAAAGCAGATGTGTATATAAG             150
TCTATGCGAAGAAGCGAAAACGAGGGCACTACTTTCTCATGGATCACTGT             200
AATGCTACAAGAGTGTCTGTGATGTATATTTATAATGTAGTTGTGTCATAT            250
AGCTTTTGTACTGTATGCAACTTATTTAACTCGCTCTTTATCTCATGGGT             300
TTTATTTAATAAAACATGTTCTTACAAAAAAAAAAA                           337
```

D

```
              -8   -4    0    4    8
P450RAI       PFGGGSRMCVGKEFAKVLLK
ATCYTP450     *****P*L*P*Y*L*R*A*S
RATCYP4A1     SA*N*IQMSEM*
RABCYP4A5     SA*N*IQMNE**
CYP4503A12    ***T*P*N*I*NR**IMNM*
hCYTP4OH      S**N*IQMNE**
```

FIG. 9

```
mP450RAI   MGLPALLASALCTFVLPLLLFLAALKLWDLYCVSSRDRSCALPLPPGTMGFPPFFGETLQM   60
hP450RAI   .................I..........G...............................   60
zP450RAI   ...YT.MVTF...I...V......V...EMLMIRRV.PN.RS.........L..I.....L   60 mP450RAI   VLQRRKFLQMKRRKYGFIYKTHLFGRPTVRVMGADNVRRILLGEHRLVSVHWPASVRTIL    120
hP450RAI   ..........................................DD...............   120
zP450RAI   I.......R..Q...C........N..........Q......K....Q............  120 mP450RAI   GAGCLSNLHDSSHKQRKKVIMQAFSREALQCYVLVIAEEVSSCLEQWLSCGERGLLVYPE    180
hP450RAI   .S..................R......E...P..T...G.S...................  180
zP450RAI   .SDT...V.GVQ..NK..A..R....D..EH.IP..QQ..K.AIQE..Q-KDSCV.....  179 mP450RAI   VKRLMFRIAMRILLGCEPGPAGGGEDEQQLVEAFEEMTRNLFSLPIDVPFSGLYRGVKAR    240
hP450RAI   ................QL..D.DS.................................M...  240
zP450RAI   M.K...........F..EQI--KT...E........IK.................LR..  237 mP450RAI   NLIHARIEENIRAKIRRLQATEPDGGCKDALQLLIEHSWERGERLDMQALKQSSTELLFG   300
hP450RAI   .......Q......CG.R.S.AGQ....................................  300
zP450RAI   .F..SK......K..QDDDNENEQ-KY.........N.RRSD.PFSL..M.EAA......  296 mP450RAI   GHETTASAATSLITYLGLYPHVLQKVREEIKSKGLLCKSNQDNKLDMETLEQLKYIGCVI   360
hP450RAI   .........................L...................I.............  360
zP450RAI   ........T....VMF...NTE.V......VQE.VEMGMYTPGKG.S..L.D....T...  356 mP450RAI   KETLRLNPPVPGGFRVALKTFELNGYQIPKGWNVIYSICDTHDVADIFTNKEEFNPDRFI   420
hP450RAI   .......................................E...........S.......  420
zP450RAI   .....I............................V.P.....Q.E..M............  416 mP450RAI   VPHPEDASRFSFIPFGGGLRSCVGKEFAKILLKIFTVELARHCDWQLLNGPPTMKTSPTV   480
hP450RAI   A............................................................  480
zP450RAI   SKGL..G...NY......S.M........V.....L...TQ..N.I.S........G..I  476 mP450RAI   YPVDNLPARFTYFQGDI                                              497
hP450RAI   ...........H.H.E.                                              497
zP450RAI   .......TK..SYVRN-                                              492
```

*a*
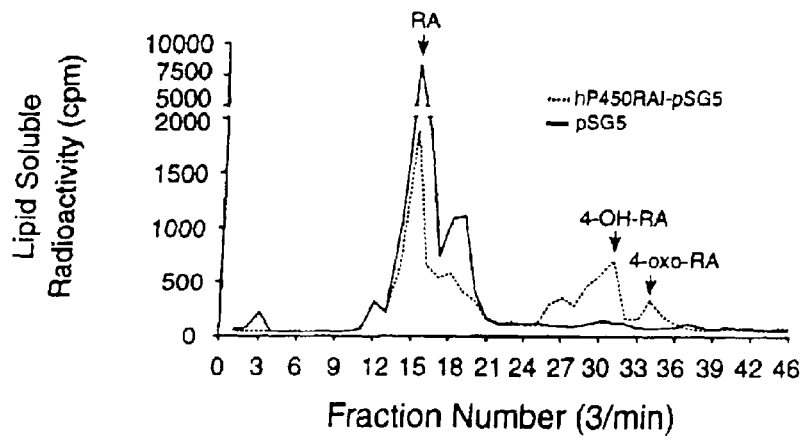
*b*
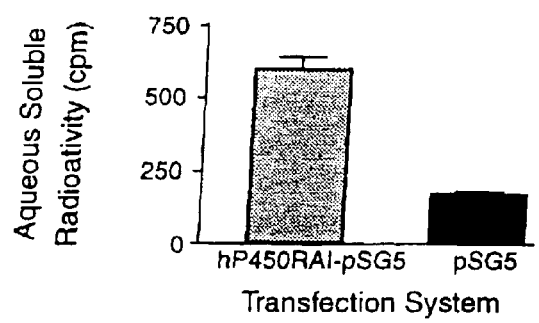
FIG. 10
*c*
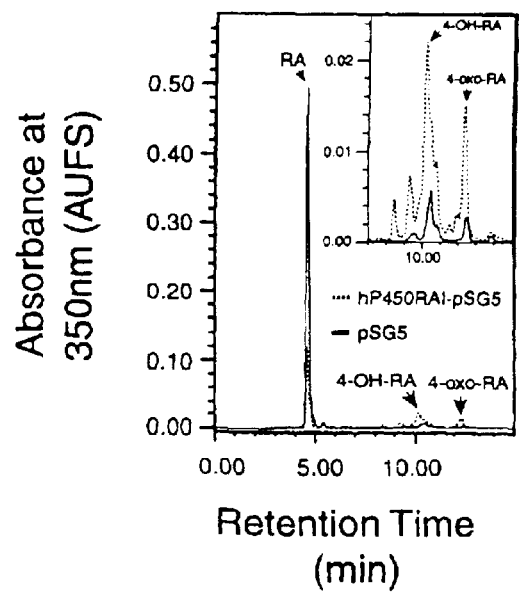

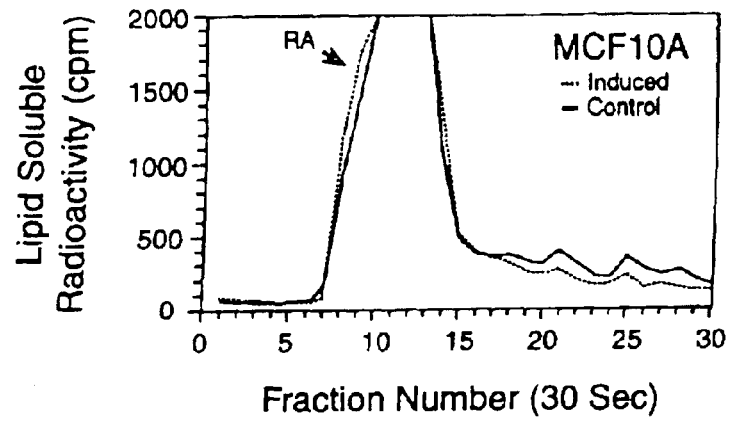
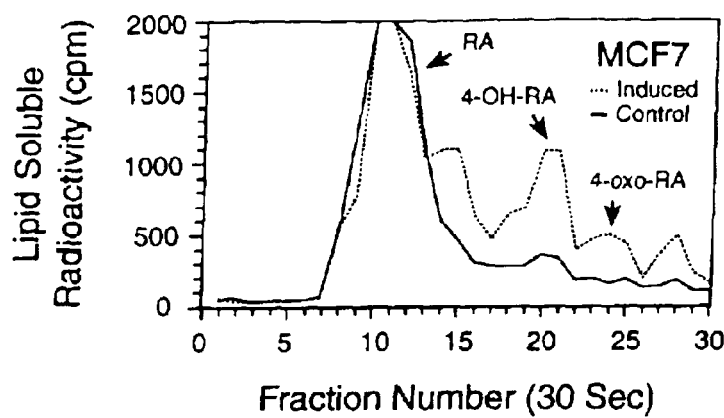
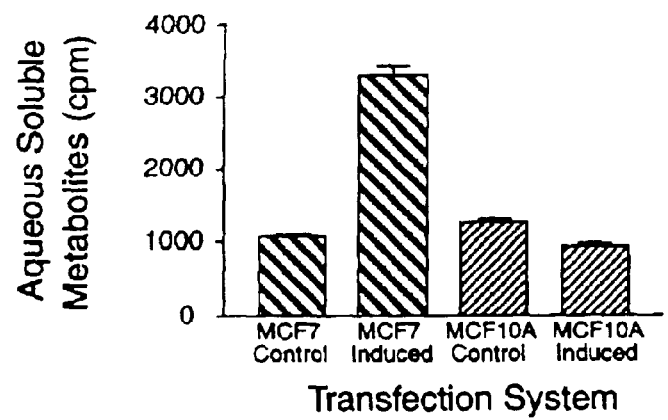
FIG. 12

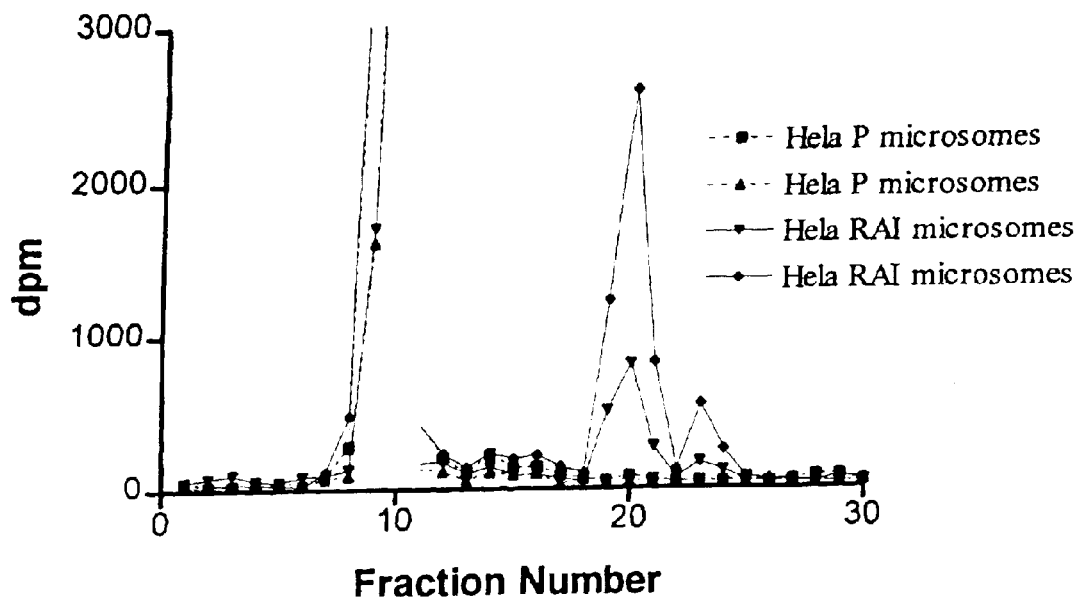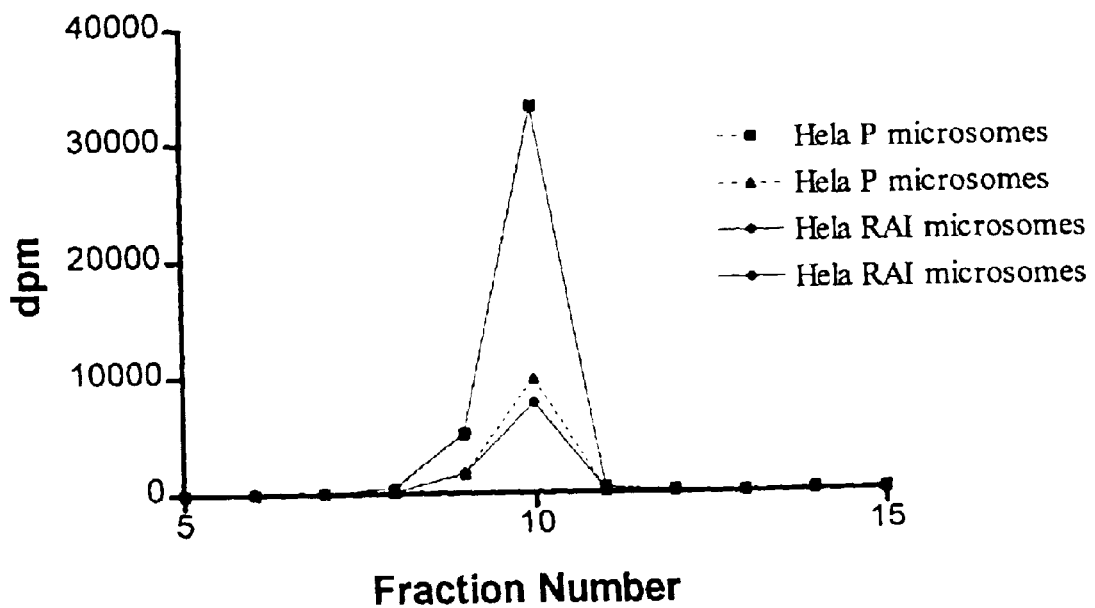
FIG. 13

```
hRAI promoter   -CG----------CA-C---------------------------CC-----CAGGAGG
mRAI promoter   -CG----------CACC--------------------------CC-----CAGGAGG
zRAI promoter   TCGGGGAATTAACACCTTTTCAAAGTGAAATCTCAGGATTGTCTGCCTTCTACAGGAGG hRAI promoter   ----------CGCGCTCGGAGGGAA--GCCGCCAC--CGCCGCCGCCTCTGCCTCGGCG
mRAI promoter   ----------CGCGCTCAGAGGGAA--GCCGCCAG--TG-CGCCGCCTCTGCCTCGGCG
zRAI promoter   TGGTATTAAAATGCGCCTATAACAAATGGTTGAGAGTTTGGAGCCGCTTCTGCCCTG--- hRAI promoter   CGGAACAAACGGTTAAAGATTTT---GGGCCASCGCCTCCGCGGGGGGAGGAGCCAGGGG
mRAI promoter   CGGAACAAACGGTTAAAGATTTTTTTGGGC-AGCGCCT-CGAGGGGGGAGGAGCCAGGGG
zRAI promoter   -------------------------TGGGC-----------GGGGCGAG-----ATG-- hRAI promoter   CCCCAATCCCGCAATTAAAGATGAACTTTGGGTGAACTAATT-GTCTGACCAAGGTAACG
mRAI promoter   CCCGA--TCCCCAATTAAAGATGAACTTTGGGTGAACTAATTTGTCTGACCAAGGTAACG
zRAI promoter   -----ACACCACAATTAAAGATGAACTTTGTGTGAACTAATTTATCTGAGGAAGTTAACA hRAI promoter   TGGGCAGCAACCTGGGCCGCC----TATAAAGCGGCAGCGCCGTGGGGTTTGAAGCGCTG
mRAI promoter   TGGGCAGTAACCTGGGCGGCC---TTATAAAGAGGGCGCGCGGCGGGGTTCGGAGCTAGG
zRAI promoter   GGAGGAGACCTGCGCGCAATGGATATATAAGGGCGCGCAGGCGAGGACGCCCTCAGTTTG hRAI promoter   GCGGCGGCGGCAGGTGGCGCGGGAGGTCG------------------------CG
mRAI promoter   GCGGCGGCGGCAGGTGGCGCGGGAGGCTG------------------------AA
zRAI promoter   TGCGTAAAGACGCGTCTCCTCTCCAGAAGCTTGTTTTTCGTTTTGGCGATCAGTTGCGCG hRAI promoter   GCGCGCCATGG
mRAI promoter   GCGTGCCATGG
zRAI promoter   CTTCAACATGG
```

FIG. 15

Cells were treated for twelve hours with the indicated concentrations of *all-trans* retinoic acid (*at*RA) and 4-HPR. Total RNA was extracted using TRIzol, and, following electrophoresis, Northern blotting was performed as described. The nitrocellulose was probed with radiolabelled P450RAI or GAPDH.

SEQUENCE LISTING (1) GENERAL INFORMATION:

(iii) NUMBER OF SEQUENCES: 43

(2) INFORMATION FOR SEQ ID NO: 1

(i) SEQUENCE CHARACTERISTICS:
      (A) LENGTH: 337 base pairs
      (B) TYPE: nucleic acid
      (C) STRANDEDNESS: single
      (D) TOPOLOGY: linear (xi) SEQUENCE DESCRIPTION: SEQ ID NO: 1

```
TGCCAGTGGA CAATCTCCCT ACCAAATTCA CTAGTTATGT CCAGAAATTA GCCTAAACCG      60

GAGCCTTTGT ACATATGTTT TTATTTTAGA TGAACTGTGA TGTATTGGAT ATTTTCTAAT     120

TTGTTTATAT AAAGCAGATG TGTATATAAG TCTATGCGAA GAAGCGAAAA CGAGGGCACT     180

ACTTTCTCAT GGATCACTGT AATGCTACAG AGTGTCTGTG ATGTATATTT ATAATGTAGT     240

TGTGTCATAT AGCTTTTGTA CTGTATGCAA CTTATTTAAC TCGCTCTTTA TCTCATGGGT     300

TTTATTTAAT AAAACATGTT CTTACAAAAA AAAAAAA                              337
```

(2) INFORMATION FOR SEQ ID NO: 2

(i) SEQUENCE CHARACTERISTICS:
      (A) LENGTH: 492 amino acids
      (B) TYPE: amino acid
      (C) STRANDEDNESS: single
      (D) TOPOLOGY: linear (xi) SEQUENCE DESCRIPTION: SEQ ID NO: 2

```
Met Gly Leu Tyr Thr Leu Met Val Thr Phe Leu Cys Thr Ile Val Leu
 1               5                  10                  15

Pro Val Leu Leu Phe Leu Ala Ala Val Lys Leu Trp Glu Met Leu Met
            20                  25                  30

Ile Arg Arg Val Asp Pro Asn Cys Arg Ser Pro Leu Pro Pro Gly Thr
        35                  40                  45

Met Gly Leu Pro Phe Ile Gly Glu Thr Leu Gln Leu Ile Leu Gln Arg
    50                  55                  60
```

-continued

```
Arg Lys Phe Leu Arg Met Lys Arg Gln Lys Tyr Gly Cys Ile Tyr Lys
 65              70                  75                  80

Thr His Leu Phe Gly Asn Pro Thr Val Arg Val Met Gly Ala Asp Asn
                 85                  90                  95

Val Arg Gln Ile Leu Leu Gly Glu His Lys Leu Val Ser Val Gln Trp
                100                 105                 110

Pro Ala Ser Val Arg Thr Ile Leu Gly Ser Asp Thr Leu Ser Asn Val
                115                 120                 125

His Gly Val Gln His Lys Asn Lys Lys Ala Ile Met Arg Ala Phe
        130                 135                 140

Ser Arg Asp Ala Leu Glu His Tyr Ile Pro Val Ile Gln Gln Glu Val
145                 150                 155                 160

Lys Ser Ala Ile Gln Glu Trp Leu Gln Lys Asp Ser Cys Val Leu Val
                165                 170                 175

Tyr Pro Glu Met Lys Lys Leu Met Phe Arg Ile Ala Met Arg Ile Leu
                180                 185                 190

Leu Gly Phe Glu Pro Glu Gln Ile Lys Thr Asp Glu Gln Glu Leu Val
                195                 200                 205

Glu Ala Phe Glu Glu Met Ile Lys Asn Leu Phe Ser Leu Pro Ile Asp
210                 215                 220

Val Pro Phe Ser Gly Leu Tyr Arg Gly Leu Arg Ala Arg Asn Phe Ile
225                 230                 235                 240

His Ser Lys Ile Glu Glu Asn Ile Arg Lys Lys Ile Gln Asp Asp Asp
                245                 250                 255

Asn Glu Asn Glu Gln Lys Tyr Lys Asp Ala Leu Gln Leu Leu Ile Glu
                260                 265                 270

Asn Ser Arg Arg Ser Asp Glu Pro Phe Ser Leu Gln Ala Met Lys Glu
                275                 280                 285

Ala Ala Thr Glu Leu Leu Phe Gly Gly His Glu Thr Thr Ala Ser Thr
        290                 295                 300

Ala Thr Ser Leu Val Met Phe Leu Gly Leu Asn Thr Glu Val Val Gln
305                 310                 315                 320

Lys Val Arg Glu Glu Val Gln Glu Lys Val Glu Met Gly Met Tyr Thr
                325                 330                 335

Pro Gly Lys Gly Leu Ser Met Glu Leu Leu Asp Gln Leu Lys Tyr Thr
                340                 345                 350

Gly Cys Val Ile Lys Glu Thr Leu Arg Ile Asn Pro Pro Val Pro Gly
        355                 360                 365

Gly Phe Arg Val Ala Leu Lys Thr Phe Glu Leu Asn Gly Tyr Gln Ile
        370                 375                 380

Pro Lys Gly Trp Asn Val Ile Tyr Ser Ile Cys Asp Thr His Asp Val
385                 390                 395                 400

Ala Asp Val Phe Pro Asn Lys Glu Glu Phe Gln Pro Glu Arg Phe Met
                405                 410                 415

Ser Lys Gly Leu Glu Asp Gly Ser Arg Phe Asn Tyr Ile Pro Phe Gly
                420                 425                 430

Gly Gly Ser Arg Met Cys Val Gly Lys Glu Phe Ala Lys Val Leu Leu
        435                 440                 445

Lys Ile Phe Leu Val Glu Leu Thr Gln His Cys Asn Trp Ile Leu Ser
        450                 455                 460

Asn Gly Pro Pro Thr Met Lys Thr Gly Pro Thr Ile Tyr Pro Val Asp
465                 470                 475                 480
```

```
                                    Asn Leu Pro Thr Lys Phe Thr Ser Tyr Val Arg Asn
                                                    485                 490

(2) INFORMATION FOR SEQ ID NO: 3

(i) SEQUENCE CHARACTERISTICS:
        (A) LENGTH: 1850 base pairs
        (B) TYPE: nucleic acid
        (C) STRANDEDNESS: single
        (D) TOPOLOGY: linear (xi) SEQUENCE DESCRIPTION: SEQ ID NO: 3

TGTCGCCGTT GCTGTCGGTT GCTGTCGGAC GCTGTCTCCT CTCCAGAAGC TTGTTTTTCG            60

TTTTGGCGAT CAGTTGCGCG CTTCAAC ATG GGG CTG TAC ACC CTT ATG GTC ACC          114
                              Met Gly Leu Tyr Thr Leu Met Val Thr
                                1               5

TTT CTC TGC ACC ATC GTG CTA CCC GTT TTA CTC TTT CTC GCC GCG GTG            162
Phe Leu Cys Thr Ile Val Leu Pro Val Leu Leu Phe Leu Ala Ala Val
10              15                  20                  25

AAG TTG TGG GAG ATG TTA ATG ATC CGA CGA GTC GAT CCG AAC TGC AGA            210
Lys Leu Trp Glu Met Leu Met Ile Arg Arg Val Asp Pro Asn Cys Arg
                30                  35                  40

AGT CCT CTA CCG CCA GGT ACC ATG GGC TTG CCG TTC ATT GGA GAA ACG            258
Ser Pro Leu Pro Pro Gly Thr Met Gly Leu Pro Phe Ile Gly Glu Thr
            45                  50                  55

CTC CAG CTG ATC CTC CAG AGA AGG AAG TTT CTG CGC ATG AAA CGG CAG            306
Leu Gln Leu Ile Leu Gln Arg Arg Lys Phe Leu Arg Met Lys Arg Gln
        60                  65                  70

AAA TAC GGG TGC ATC TAC AAG ACG CAC CTC TTC GGG AAC CCG ACT GTC            354
Lys Tyr Gly Cys Ile Tyr Lys Thr His Leu Phe Gly Asn Pro Thr Val
75                  80                  85

AGG GTG ATG GGA GCT GAT AAT GTG AGG CAG ATT CTG CTG GGC GAA CAC            402
Arg Val Met Gly Ala Asp Asn Val Arg Gln Ile Leu Leu Gly Glu His
90              95                  100                 105

AAG CTG GTG TCT GTT CAG TGG CCA GCA TCA GTG AGA ACC ATC CTG GGC            450
Lys Leu Val Ser Val Gln Trp Pro Ala Ser Val Arg Thr Ile Leu Gly
            110                 115                 120

TCT GAC ACC CTC TCC AAT GTC CAT GGA GTT CAA CAC AAA AAC AAG AAA            498
Ser Asp Thr Leu Ser Asn Val His Gly Val Gln His Lys Asn Lys Lys
        125                 130                 135

AAG GCC ATT ATG AGG GCG TTC TCT CGA GAT GCT CTG GAG CAC TAC ATT            546
Lys Ala Ile Met Arg Ala Phe Ser Arg Asp Ala Leu Glu His Tyr Ile
    140                 145                 150

CCC GTG ATC CAG CAG GAG GTG AAG AGC GCC ATA CAG GAA TGG CTG CAA            594
Pro Val Ile Gln Gln Glu Val Lys Ser Ala Ile Gln Glu Trp Leu Gln
155                 160                 165

AAA GAC TCC TGC GTG CTG GTT TAT CCA GAA ATG AAG AAA CTC ATG TTT            642
Lys Asp Ser Cys Val Leu Val Tyr Pro Glu Met Lys Lys Leu Met Phe
170                 175                 180                 185

CGG ATA GCT ATG AGA ATC CTG CTT GGT TTT GAA CCA GAG CAA ATA AAG            690
Arg Ile Ala Met Arg Ile Leu Leu Gly Phe Glu Pro Glu Gln Ile Lys
                190                 195                 200

ACG GAC GAG CAA GAA CTG GTG GAA GCT TTT GAG GAA ATG ATC AAA AAC            738
Thr Asp Glu Gln Glu Leu Val Glu Ala Phe Glu Glu Met Ile Lys Asn
            205                 210                 215

TTG TTC TCC TTG CCA ATC GAC GTT CCT TTC AGT GGT CTG TAC AGG GGT            786
Leu Phe Ser Leu Pro Ile Asp Val Pro Phe Ser Gly Leu Tyr Arg Gly
        220                 225                 230

TTG AGG GCA CGC AAT TTC ATT CAC TCC AAA ATT GAG GAA AAC ATC AGG            834
Leu Arg Ala Arg Asn Phe Ile His Ser Lys Ile Glu Glu Asn Ile Arg
    235                 240                 245
```

-continued

```
AAG AAA ATT CAA GAT GAC GAC AAT GAA AAC GAA CAG AAA TAC AAA GAC       882
Lys Lys Ile Gln Asp Asp Asp Asn Glu Asn Glu gln Lys Tyr Lys Asp
250                 255                 260                 265

GCC CTT CAG CTG TTG ATC GAG AAC AGC AGA AGA AGT GAC GAA CCT TTT       930
Ala Leu Gln Leu Leu Ile Glu Asn Ser Arg Arg Ser Asp Glu Pro Phe
                270                 275                 280

AGT TTG CAG GCG ATG AAA GAA GCA GCT ACA GAG CTT CTA TTT GGA GGT       978
Ser Leu Gln Ala Met Lys Glu Ala Ala Thr Glu Leu Leu Phe Gly Gly
            285                 290                 295

CAT GAA ACC ACC GCC AGC ACT GCA ACC TCA CTT GTC ATG TTT CTG GGT      1026
His Glu Thr Thr Ala Ser Thr Ala Thr Ser Leu Val Met Phe Leu Gly
        300                 305                 310

CTG AAC ACA GAA GTG GTG CAG AAG GTC AGA GAG GAG GTT CAG GAG AAG      1074
Leu Asn Thr Glu Val Val Gln Lys Val Arg Glu Glu Val Gln Glu Lys
    315                 320                 325

GTT GAA ATG GGC ATG TAT ACA CCT GGA AAG GGC TTG AGT ATG GAG CTG      1122
Val Glu Met Gly Met Tyr Thr Pro Gly Lys Gly Leu Ser Met Glu Leu
330                 335                 340                 345

TTG GAC CAG CTG AAG TAC ACT GGA TGT GTG ATT AAA GAG ACT CTT AGA      1170
Leu Asp Gln Leu Lys Tyr Thr Gly Cys Val Ile Lys Glu Thr Leu Arg
                350                 355                 360

ATC AAC CCT CCT GTT CCC GGA GGA TTC AGA GTC GCA CTC AAA ACC TTT      1218
Ile Asn Pro Pro Val Pro Gly Gly Phe Arg Val Ala Leu Lys Thr Phe
            365                 370                 375

GAA TTG AAT GGT TAC CAA ATT CCT AAA GGA TGG AAC GTC ATT TAC AGC      1266
Glu Leu Asn Gly Tyr Gln Ile Pro Lys Gly Trp Asn Val Ile Tyr Ser
        380                 385                 390

ATC TGT GAC ACG CAC GAT GTG GCC GAC GTC TTT CCA AAC AAA GAG GAG      1314
Ile Cys Asp Thr His Asp Val Ala Asp Val Phe Pro Asn Lys Glu Glu
    395                 400                 405

TTC CAG CCG GAG AGA TTC ATG AGC AAA GGT CTG GAG GAC GGG TCC AGG      1362
Phe Gln Pro Glu Arg Phe Met Ser Lys Gly Leu Glu Asp Gly Ser Arg
410                 415                 420                 425

TTT AAC TAC ATC CCC TTC GGA GGA GGA TCC AGG ATG TGT GTG GGC AAA      1410
Phe Asn Tyr Ile Pro Phe Gly Gly Gly Ser Arg Met Cys Val Gly Lys
                430                 435                 440

GAG TTC GCC AAA GTG TTA CTC AAG ATC TTT TTA GTT GAG TTA ACG CAG      1458
Glu Phe Ala Lys Val Leu Leu Lys Ile Phe Leu Val Glu Leu Thr Gln
            445                 450                 455

CAT TGC AAT TGG ATT CTC TCA AAC GGA CCC CCG ACA ATG AAA ACA GGC      1506
His Cys Asn Trp Ile Leu Ser Asn Gly Pro Pro Thr Met Lys Thr Gly
        460                 465                 470

CCG ACT ATT TAC CCA GTG GAC AAT CTC CCT ACC AAA TTC ACT AGT TAT      1554
Pro Thr Ile Tyr Pro Val Asp Asn Leu Pro Thr Lys Phe Thr Ser Tyr
    475                 480                 485

GTC AGA AAT TAGCCTAACC GGAGCTTTGT ACATATGTTT TTATTTTAGA              1603
Val Arg Asn
490

TGAACTGTGA TGTATTGGAT ATTTTCTATT TTGTTTATAT AAAGCAGATG TGTATATAAG    1663

TCTATGCGAG GAAGCGAAAA CGAGGGCACT ACTTTCTCAT GGATCACTGT AATGCTACAG    1723

AGTGTCTGTG ATGTATATTT ATAATGTAGT TGTGTTATAT AGCTTTTGTA CTGTATGCAA    1783

CTTATTTAAC TCGCTCTTTA TCTCATGGGT TTTATTTAAT AAAACATGTT CTTACAAAAA    1843

AAAAAAA                                                              1850
```

(2) INFORMATION FOR SEQ ID NO: 4

(i) SEQUENCE CHARACTERISTICS:

(A) LENGTH: 497 amino acids
(B) TYPE: amino acid
(C) STRANDEDNESS: single
(D) TOPOLOGY: linear (xi) SEQUENCE DESCRIPTION: SEQ ID NO: 4

```
Met Gly Leu Pro Ala Leu Leu Ala Ser Ala Leu Cys Thr Phe Val Leu
 1               5                  10                  15

Pro Leu Leu Phe Leu Ala Ala Ile Lys Leu Trp Asp Leu Tyr Cys
            20                  25                  30

Val Ser Gly Arg Asp Arg Ser Cys Ala Leu Pro Leu Pro Pro Gly Thr
            35                  40                  45

Met Gly Phe Pro Phe Phe Gly Glu Thr Leu Gln Met Val Leu Gln Arg
 50                  55                  60

Arg Lys Phe Leu Gln Met Lys Arg Arg Lys Tyr Gly Phe Ile Tyr Lys
 65                  70                  75                  80

Thr His Leu Phe Gly Arg Pro Thr Val Arg Val Met Gly Ala Asp Asn
                    85                  90                  95

Val Arg Arg Ile Leu Leu Gly Asp Asp Arg Leu Val Ser Val His Trp
                100                 105                 110

Pro Ala Ser Val Arg Thr Ile Leu Gly Ser Gly Cys Leu Ser Asn Leu
            115                 120                 125

His Asp Ser Ser His Lys Gln Arg Lys Val Ile Met Arg Ala Phe
130                 135                 140

Ser Arg Glu Ala Leu Glu Cys Tyr Val Pro Val Ile Thr Glu Glu Val
145                 150                 155                 160

Gly Ser Ser Leu Glu Gln Trp Leu Ser Cys Gly Glu Arg Gly Leu Leu
                    165                 170                 175

Val Tyr Pro Glu Val Lys Arg Leu Met Phe Arg Ile Ala Met Arg Ile
                180                 185                 190

Leu Leu Gly Cys Glu Pro Gln Leu Ala Gly Asp Gly Asp Ser Glu Gln
            195                 200                 205

Gln Leu Val Glu Ala Phe Glu Glu Met Thr Arg Asn Leu Phe Ser Leu
210                 215                 220

Pro Ile Asp Val Pro Phe Ser Gly Leu Tyr Arg Gly Met Lys Ala Arg
225                 230                 235                 240

Asn Leu Ile His Ala Arg Ile Glu Gln Asn Ile Arg Ala Lys Ile Cys
                245                 250                 255

Gly Leu Arg Ala Ser Glu Ala Gly Gln Gly Cys Lys Asp Ala Leu Gln
                260                 265                 270

Leu Leu Ile Glu His Ser Trp Glu Arg Gly Glu Arg Leu Asp Met Gln
            275                 280                 285

Ala Leu Lys Gln Ser Ser Thr Glu Leu Leu Phe Gly Gly His Glu Thr
290                 295                 300

Thr Ala Ser Ala Ala Thr Ser Leu Ile Thr Tyr Leu Gly Leu Tyr Pro
305                 310                 315                 320

His Val Leu Gln Lys Val Arg Glu Glu Leu Lys Ser Lys Gly Leu Leu
                325                 330                 335

Cys Lys Ser Asn Gln Asp Asn Lys Leu Asp Met Glu Ile Leu Glu Gln
                340                 345                 350

Leu Lys Tyr Ile Gly Cys Val Ile Lys Glu Thr Leu Arg Leu Asn Pro
            355                 360                 365

Pro Val Pro Gly Gly Phe Arg Val Ala Leu Lys Thr Phe Glu Leu Asn
370                 375                 380
```

-continued

```
Gly Tyr Gln Ile Pro Lys Gly Trp Asn Val Ile Tyr Ser Ile Cys Asp
385                 390                 395                 400

Thr His Asp Val Ala Glu Ile Phe Thr Asn Lys Glu Glu Phe Asn Pro
                405                 410                 415

Asp Arg Phe Ser Ala Pro His Pro Glu Asp Ala Ser Arg Phe Ser Phe
                420                 425                 430

Ile Pro Phe Gly Gly Gly Leu Arg Ser Cys Val Gly Lys Glu Phe Ala
                435                 440                 445

Lys Ile Leu Leu Lys Ile Phe Thr Val Glu Leu Ala Arg His Cys Asp
450                 455                 460

Trp Gln Leu Leu Asn Gly Pro Pro Thr Met Lys Thr Ser Pro Thr Val
465                 470                 475                 480

Tyr Pro Val Asp Asn Leu Pro Ala Arg Phe Thr His Phe His Gly Glu
                485                 490                 495

Ile
```

(2) INFORMATION FOR SEQ ID NO: 5

(i) SEQUENCE CHARACTERISTICS:
        (A) LENGTH: 1494 base pairs
        (B) TYPE: nucleic acid
        (C) STRANDEDNESS: single
        (D) TOPOLOGY: linear (xi) SEQUENCE DESCRIPTION: SEQ ID NO: 5

```
ATG GGG CTC CCG GCG CTG CTG GCC AGT GCG CTC TGC ACC TTC GTG CTG     48
Met Gly Leu Pro Ala Leu Leu Ala Ser Ala Leu Cys Thr Phe Val Leu
1               5                   10                  15

CCG CTG CTG CTC TTC CTG GCT GCG ATC AAG CTC TGG GAC CTG TAC TGC     96
Pro Leu Leu Leu Phe Leu Ala Ala Ile Lys Leu Trp Asp Leu Tyr Cys
                20                  25                  30

GTG AGC GGC CGC GAC CGC AGT TGT GCC CTC CCA TTG CCC CCC GGG ACT    144
Val Ser Gly Arg Asp Arg Ser Cys Ala Leu Pro Leu Pro Pro Gly Thr
            35                  40                  45

ATG GGC TTC CCC TTC TTT GGG GAA ACC TTG CAG ATG GTA CTG CAG CGG    192
Met Gly Phe Pro Phe Phe Gly Glu Thr Leu Gln Met Val Leu Gln Arg
        50                  55                  60

AGG AAG TTC CTG CAG ATG AAG CGC AGG AAA TAC GGC TTC ATC TAC AAG    240
Arg Lys Phe Leu Gln Met Lys Arg Arg Lys Tyr Gly Phe Ile Tyr Lys
65                  70                  75                  80

ACG CAT CTG TTC GGG CGG CCC ACC GTA CGG GTG ATG GGC GCG GAC AAT    288
Thr His Leu Phe Gly Arg Pro Thr Val Arg Val Met Gly Ala Asp Asn
                85                  90                  95

GTG CGG CGC ATC TTG CTC GGA GAC GAC CGG CTG GTG TCG GTC CAC TGG    336
Val Arg Arg Ile Leu Leu Gly Asp Asp Arg Leu Val Ser Val His Trp
            100                 105                 110

CCA GCG TCG GTG CGC ACC ATT CTG GGA TCT GGC TGC CTC TCT AAC CTG    384
Pro Ala Ser Val Arg Thr Ile Leu Gly Ser Gly Cys Leu Ser Asn Leu
        115                 120                 125

CAC GAC TCC TCG CAC AAG CAG CGC AAG AAG GTG ATT ATG CGG GCC TTC    432
His Asp Ser Ser His Lys Gln Arg Lys Lys Val Ile Met Arg Ala Phe
    130                 135                 140

AGC CGC GAG GCA CTC GAA TGC TAC GTG CCG GTG ATC ACC GAG GAA GTG    480
Ser Arg Glu Ala Leu Glu Cys Tyr Val Pro Val Ile Thr Glu Glu Val
145                 150                 155                 160

GGC AGC AGC CTG GAG CAG TGG CTG AGC TGC GGC GAG CGC GGC CTC CTG    528
Gly Ser Ser Leu Glu Gln Trp Leu Ser Cys Gly Glu Arg Gly Leu Leu
                165                 170                 175

GTC TAC CCC GAG GTG AAG CGC CTC ATG TTC CGA ATC GCC ATG CGC ATC    576
```

```
                Val Tyr Pro Glu Val Lys Arg Leu Met Phe Arg Ile Ala Met Arg Ile
                            180                 185                 190

CTA CTG GGC TGC GAA CCC CAA CTG GCG GGC GAC GGG GAC TCC GAG CAG           624
Leu Leu Gly Cys Glu Pro Gln Leu Ala Gly Asp Gly Asp Ser Glu Gln
            195                 200                 205

CAG CTT GTG GAG GCC TTC GAG GAA ATG ACC CGC AAT CTC TTC TCG CTG           672
Gln Leu Val Glu Ala Phe Glu Glu Met Thr Arg Asn Leu Phe Ser Leu
            210                 215                 220

CCC ATC GAC GTG CCC TTC AGC GGG CTG TAC CGG GGC ATG AAG GCG CGG           720
Pro Ile Asp Val Pro Phe Ser Gly Leu Tyr Arg Gly Met Lys Ala Arg
225                 230                 235                 240

AAC CTC ATT CAC GCG CGC ATC GAG CAG AAC ATT CGC GCC AAG ATC TGC           768
Asn Leu Ile His Ala Arg Ile Glu Gln Asn Ile Arg Ala Lys Ile Cys
            245                 250                 255

GGG CTG CGG GCA TCC GAG GCG GGC CAG GGC TGC AAA GAC GCG CTG CAG           816
Gly Leu Arg Ala Ser Glu Ala Gly Gln Gly Cys Lys Asp Ala Leu Gln
            260                 265                 270

CTG TTG ATC GAG CAC TCG TGG GAG AGG GGA GAG CGG CTG GAC ATG CAG           864
Leu Leu Ile Glu His Ser Trp Glu Arg Gly Glu Arg Leu Asp Met Gln
            275                 280                 285

GCA CTA AAG CAA TCT TCA ACC GAA CTC CTC TTT GGA GGA CAC GAA ACC           912
Ala Leu Lys Gln Ser Ser Thr Glu Leu Leu Phe Gly Gly His Glu Thr
290                 295                 300

ACG GCC AGT GCA GCC ACA TCT CTG ATC ACT TAC CTG GGG CTC TAC CCA           960
Thr Ala Ser Ala Ala Thr Ser Leu Ile Thr Tyr Leu Gly Leu Tyr Pro
305                 310                 315                 320

CAT GTT CTC CAG AAA GTG CGA GAA GAG CTG AAG AGT AAG GGT TTA CTT          1008
His Val Leu Gln Lys Val Arg Glu Glu Leu Lys Ser Lys Gly Leu Leu
            325                 330                 335

TGC AAG AGC AAT CAA GAC AAC AAG TTG GAC ATG GAA ATT TTG GAA CAA          1056
Cys Lys Ser Asn Gln Asp Asn Lys Leu Asp Met Glu Ile Leu Glu Gln
            340                 345                 350

CTT AAA TAC ATC GGG TGT GTT ATT AAG GAG ACC CTT CGA CTG AAT CCC          1104
Leu Lys Tyr Ile Gly Cys Val Ile Lys Glu Thr Leu Arg Leu Asn Pro
            355                 360                 365

CCA GTT CCA GGA GGG TTT CGG GTT GCT CTG AAG ACT TTT GAA TTA AAT          1152
Pro Val Pro Gly Gly Phe Arg Val Ala Leu Lys Thr Phe Glu Leu Asn
370                 375                 380

GGA TAC CAG ATT CCC AAG GGC TGG AAT GTT ATC TAC AGT ATC TGT GAT          1200
Gly Tyr Gln Ile Pro Lys Gly Trp Asn Val Ile Tyr Ser Ile Cys Asp
385                 390                 395                 400

ACT CAT GAT GTG GCA GAG ATC TTC ACC AAC AAG GAA GAA TTT AAT CCT          1248
Thr His Asp Val Ala Glu Ile Phe Thr Asn Lys Glu Glu Phe Asn Pro
            405                 410                 415

GAC CGA TTC AGT GCT CCT CAC CCA GAG GAT GCA TCC AGG TTC AGC TTC          1296
Asp Arg Phe Ser Ala Pro His Pro Glu Asp Ala Ser Arg Phe Ser Phe
            420                 425                 430

ATT CCA TTT GGA GGA GGC CTT AGG AGC TGT GTA GGC AAA GAA TTT GCA          1344
Ile Pro Phe Gly Gly Gly Leu Arg Ser Cys Val Gly Lys Glu Phe Ala
            435                 440                 445

AAA ATT CTT CTC AAA ATA TTT ACA GTG GAG CTG GCC AGG CAT TGT GAC          1392
Lys Ile Leu Leu Lys Ile Phe Thr Val Glu Leu Ala Arg His Cys Asp
450                 455                 460

TGG CAG CTT CTA AAT GGA CCT CCT ACA ATG AAA ACC AGT CCC ACC GTG          1440
Trp Gln Leu Leu Asn Gly Pro Pro Thr Met Lys Thr Ser Pro Thr Val
465                 470                 475                 480

TAT CCT GTG GAC AAT CTC CCT GCA AGA TTC ACC CAT TTC CAT GGG GAA          1488
Tyr Pro Val Asp Asn Leu Pro Ala Arg Phe Thr His Phe His Gly Glu
            485                 490                 495
```

-continued

```
ATC TGA                                                              1494
Ile
```

(2) INFORMATION FOR SEQ ID NO: 6

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO: 6

```
Pro Phe Gly Gly Gly Pro Arg Leu Cys Pro Gly Tyr Glu Leu Ala Arg
 1               5                  10                  15
Val Ala Leu Ser
         20
```

(2) INFORMATION FOR SEQ ID NO: 7

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO: 7

```
Pro Phe Ser Gly Gly Ala Arg Asn Cys Ile Gly Lys Gln Phe Ala Met
 1               5                  10                  15
Ser Glu Met Lys
         20
```

(2) INFORMATION FOR SEQ ID NO: 8

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO: 8

```
Pro Phe Ser Gly Gly Ala Arg Asn Cys Ile Gly Lys Gln Phe Ala Met
 1               5                  10                  15
Asn Glu Leu Lys
         20
```

(2) INFORMATION FOR SEQ ID NO: 9

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO: 9

```
Pro Phe Gly Thr Gly Pro Arg Asn Cys Ile Gly Met Arg Phe Ala Ile
 1               5                  10                  15
Met Asn Met Lys
         20
```

(2) INFORMATION FOR SEQ ID NO: 10

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO: 10

Pro Phe Ser Gly Gly Ser Arg Asn Cys Ile Gly Lys Gln Phe Ala Met
1               5                   10                  15

Asn Glu Leu Lys
        20

(2) INFORMATION FOR SEQ ID NO: 11

(i) SEQUENCE CHARACTERISTICS:
        (A) LENGTH: 351 base pairs
        (B) TYPE: nucleic acid
        (C) STRANDEDNESS: single
        (D) TOPOLOGY: linear (xi) SEQUENCE DESCRIPTION: SEQ ID NO: 11

GAACTCCTCT TTGGAGGACA CGAAACCACG GCCAGTGCAG CCACATCTCT GATCACTTAC      60

CTGGGGCTCT ACCCACATGT TCTCCAGAAA GTGCGAGAAG AGCTGAAGAG TAAGGGTTTA     120

CTTTGCAAGA GCAATCAAGA CAACAAGTTG GACATGGAAA TTTTGGAACA ACTTAAATAA     180

ATCGGGTGTG TTATTAAGGA GACCCTTCGA CTGAATCCCC CAGTTCCAGG AGGGTTTCGG     240

GTTGCTCTGA AGACTTTTGA ATTAAATGGA TACCAGATTC CCAAGGGCTG GAATGTTATC     300

TACAGTATCT GTGATACTCA TGATGTGGCA GAGATCTTCA CCAACAAGGA A              351

(2) INFORMATION FOR SEQ ID NO: 12

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 12

TTTTTTTTTT TTGG                                                        14

(2) INFORMATION FOR SEQ ID NO: 13

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 13

TTTTTTTTTT TTGA                                                        14

(2) INFORMATION FOR SEQ ID NO: 14

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 14

TTTTTTTTTT TTGT                                                        14

(2) INFORMATION FOR SEQ ID NO: 15

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 15

TTTTTTTTTT TTGC                                             14

(2) INFORMATION FOR SEQ ID NO: 16

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 16

TTTTTTTTTT TTAG                                             14

(2) INFORMATION FOR SEQ ID NO: 17

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 17

TTTTTTTTTT TTAA                                             14

(2) INFORMATION FOR SEQ ID NO: 18

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 18

TTTTTTTTTT TTAT                                             14

(2) INFORMATION FOR SEQ ID NO: 19

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 19

TTTTTTTTTT TTAC                                             14

(2) INFORMATION FOR SEQ ID NO: 20

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 20

TTTTTTTTTT TTCG                                             14

(2) INFORMATION FOR SEQ ID NO: 21

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 21

TTTTTTTTTT TTCA                                                                                      14

(2) INFORMATION FOR SEQ ID NO: 22

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 22

TTTTTTTTTT TTCT                                                                                      14

(2) INFORMATION FOR SEQ ID NO: 23

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 23

TTTTTTTTTT TTCC                                                                                      14

(2) INFORMATION FOR SEQ ID NO: 24

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 24

AAGCGACCGA                                                                                           10

(2) INFORMATION FOR SEQ ID NO: 25

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 25

TGTTCGCCAG                                                                                           10

(2) INFORMATION FOR SEQ ID NO: 26

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 26

TGCCAGTGGA                                                                                           10

(2) INFORMATION FOR SEQ ID NO: 27

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 27

(2) INFORMATION FOR SEQ ID NO: 28

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 28

```
CCTAGCGTTG                                                      10
```

(2) INFORMATION FOR SEQ ID NO: 29

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 29

```
GTAGCGGCCG CTGCCAGTGG A                                         21
```

(2) INFORMATION FOR SEQ ID NO: 30

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO: 30

```
GTAGCGGCCG CT                                                   12
```

(2) INFORMATION FOR SEQ ID NO: 31

(i) SEQUENCE CHARACTERISTICS:
        (A) LENGTH: 1725 base pairs
        (B) TYPE: nucleic acid
        (C) STRANDEDNESS: single
        (D) TOPOLOGY: linear (xi) SEQUENCE DESCRIPTION: SEQ ID NO: 31

```
GCACGAGGGA GGCTGAAGCG TGCC ATG GGG CTC CCG GCG CTG CTG GCC AGT     51
                          Met Gly Leu Pro Ala Leu Leu Ala Ser
                           1               5

GCG CTC TGC ACC TTC GTG CTG CCG CTG CTG CTC TTC CTG GCG GCG CTC    99
Ala Leu Cys Thr Phe Val Leu Pro Leu Leu Leu Phe Leu Ala Ala Leu
 10              15                  20                  25

AAG CTC TGG GAC CTG TAC TGT GTG AGC AGC CGC GAT CGC AGC TGC GCC   147
Lys Leu Trp Asp Leu Tyr Cys Val Ser Ser Arg Asp Arg Ser Cys Ala
                 30                  35                  40

CTC CCC TTG CCC CCC GGT ACC ATG GGC TTC CCA TTC TTT GGG GAA ACA   195
Leu Pro Leu Pro Pro Gly Thr Met Gly Phe Pro Phe Phe Gly Glu Thr
             45                  50                  55

TTG CAG ATG GTG CTT CAG CGG AGG AAG TTT CTG CAG ATG AAG CGC AGG   243
Leu Gln Met Val Leu Gln Arg Arg Lys Phe Leu Gln Met Lys Arg Arg
         60                  65                  70

AAA TAC GGC TTC ATC TAC AAG ACG CAT CTG TTT GGG CGG CCC ACG GTG   291
Lys Tyr Gly Phe Ile Tyr Lys Thr His Leu Phe Gly Arg Pro Thr Val
     75                  80                  85

CGG GTG ATG GGC GCG GAT AAT GTG CGG CGC ATC TTG CTG GGA GAG CAC   339
Arg Val Met Gly Ala Asp Asn Val Arg Arg Ile Leu Leu Gly Glu His
```

-continued

```
        90              95              100             105
CGG TTG GTG TCG GTG CAC TGG CCC GCG TCG GTG CGC ACC ATC CTG GGC        387
Arg Leu Val Ser Val His Trp Pro Ala Ser Val Arg Thr Ile Leu Gly
            110             115             120

GCT GGC TGC CTC TCC AAC CTG CAC GAT TCC TCG CAC AAG CAG CGA AAG        435
Ala Gly Cys Leu Ser Asn Leu His Asp Ser Ser His Lys Gln Arg Lys
            125             130             135

AAG GTG ATT ATG CAG GCC TTC AGC CGC GAG GCA CTC CAG TGC TAC GTG        483
Lys Val Ile Met Gln Ala Phe Ser Arg Glu Ala Leu Gln Cys Tyr Val
            140             145             150

CTC GTG ATC GCT GAG GAA GTC AGC AGT TGT CTG GAG CAG TGG CTA AGC        531
Leu Val Ile Ala Glu Glu Val Ser Ser Cys Leu Glu Gln Trp Leu Ser
    155             160             165

TGC GGC GAG CGC GGC CTC CTG GTC TAC CCC GAG GTG AAG CGC CTC ATG        579
Cys Gly Glu Arg Gly Leu Leu Val Tyr Pro Glu Val Lys Arg Leu Met
170             175             180             185

TTC CGC ATC GCC ATG CGC ATC CTG CTG GGC TGC GAG CCG GGT CCA GCG        627
Phe Arg Ile Ala Met Arg Ile Leu Leu Gly Cys Glu Pro Gly Pro Ala
                190             195             200

GGC GGC GGG GAG GAC GAG CAA CAG CTC GTG GAG GCT TTC GAG GAG ATG        675
Gly Gly Gly Glu Asp Glu Gln Gln Leu Val Glu Ala Phe Glu Glu Met
            205             210             215

ACC CGC AAT CTC TTC TCT CTT CCC ATT GAC GTG CCC TTT AGC GGC CTG        723
Thr Arg Asn Leu Phe Ser Leu Pro Ile Asp Val Pro Phe Ser Gly Leu
            220             225             230

TAC CGG GGC GTG AAG GCG CGG AAC CTT ATA CAC GCG CGC ATC GAG GAG        771
Tyr Arg Gly Val Lys Ala Arg Asn Leu Ile His Ala Arg Ile Glu Glu
    235             240             245

AAC ATT CGC GCC AAG ATC CGC CGG CTT CAG GCT ACA GAG CCG GAT GGG        819
Asn Ile Arg Ala Lys Ile Arg Arg Leu Gln Ala Thr Glu Pro Asp Gly
250             255             260             265

GGT TGC AAG GAC GCG CTG CAG CTC CTG ATT GAG CAC TCG TGG GAG AGG        867
Gly Cys Lys Asp Ala Leu Gln Leu Leu Ile Glu His Ser Trp Glu Arg
                270             275             280

GGA GAG AGG CTG GAT ATG CAG GCA CTA AAA CAA TCG TCA ACA GAG CTC        915
Gly Glu Arg Leu Asp Met Gln Ala Leu Lys Gln Ser Ser Thr Glu Leu
            285             290             295

CTC TTT GGT GGT CAT GAA ACT ACA GCC AGT GCT GCG ACA TCA CTG ATC        963
Leu Phe Gly Gly His Glu Thr Thr Ala Ser Ala Ala Thr Ser Leu Ile
            300             305             310

ACT TAC CTA GGA CTC TAC CCA CAT GTC CTC CAG AAA GTT CGA GAA GAG       1011
Thr Tyr Leu Gly Leu Tyr Pro His Val Leu Gln Lys Val Arg Glu Glu
    315             320             325

ATA AAG AGC AAG GGC TTA CTT TGC AAG AGC AAT CAA GAC AAC AAG TTA       1059
Ile Lys Ser Lys Gly Leu Leu Cys Lys Ser Asn Gln Asp Asn Lys Leu
330             335             340             345

GAC ATG GAA ACT TTG GAA CAG CTT AAA TAC ATT GGG TGT GTC ATT AAG       1107
Asp Met Glu Thr Leu Glu Gln Leu Lys Tyr Ile Gly Cys Val Ile Lys
                350             355             360

GAG ACC CTG CGA TTG AAT CCT CCG GTT CCA GGA GGG TTT CGG GTT GCT       1155
Glu Thr Leu Arg Leu Asn Pro Pro Val Pro Gly Gly Phe Arg Val Ala
            365             370             375

CTG AAG ACT TTT GAG CTG AAT GGA TAC CAG ATC CCC AAG GGC TGG AAT       1203
Leu Lys Thr Phe Glu Leu Asn Gly Tyr Gln Ile Pro Lys Gly Trp Asn
            380             385             390

GTT ATT TAC AGT ATC TGT GAC ACC CAC GAT GTG GCA GAT ATC TTC ACT       1251
Val Ile Tyr Ser Ile Cys Asp Thr His Asp Val Ala Asp Ile Phe Thr
    395             400             405

AAC AAG GAG GAA TTT AAT CCC GAC CGC TTT ATA GTG CCT CAT CCA GAG       1299
```

-continued

```
Asn Lys Glu Glu Phe Asn Pro Asp Arg Phe Ile Val Pro His Pro Glu
410                 415                 420                 425

GAT GCT TCC CGG TTC AGC TTC ATT CCA TTT GGA GGA GGC CTT CGG AGC      1347
Asp Ala Ser Arg Phe Ser Phe Ile Pro Phe Gly Gly Gly Leu Arg Ser
                430                 435                 440

TGT GTA GGC AAA GAG TTT GCA AAA ATT CTT CTT AAG ATA TTT ACA GTG      1395
Cys Val Gly Lys Glu Phe Ala Lys Ile Leu Leu Lys Ile Phe Thr Val
                445                 450                 455

GAG CTG GCT AGG CAC TGT GAT TGG CAG CTT CTA AAT GGA CCT CCT ACA      1443
Glu Leu Ala Arg His Cys Asp Trp Gln Leu Leu Asn Gly Pro Pro Thr
                460                 465                 470

ATG AAG ACA AGC CCC ACT GTG TAC CCT GTG GAC AAT CTC CCT GCA AGA      1491
Met Lys Thr Ser Pro Thr Val Tyr Pro Val Asp Asn Leu Pro Ala Arg
475                 480                 485

TTC ACC TAC TTC CAG GGA GAT ATC TGATAGCTAT TCAATTCTT                 1535
Phe Thr Tyr Phe Gln Gly Asp Ile
490                 495

GGACTTATTT GAAGTGTATA TTGGTTTTTT TTAAAAATAG TGTCATGTTG ACTTTATTTA    1595

ATTTCTAAAT GTATAGTATG ATATTTATGT GTCTCTACTA CAGTCCCGTG GTCTTTAAAT    1655

ATTAAAATAA TGAATTTGTA TGATTTCCCA ATAAAGTAAA ATTAAAAAGT GAAAAAAAA     1715

AAAAAAAAAA                                                           1725

(2) INFORMATION FOR SEQ ID NO: 32

(i) SEQUENCE CHARACTERISTICS:
        (A) LENGTH: 497 amino acids
        (B) TYPE: amino acid
        (C) STRANDEDNESS: single
        (D) TOPOLOGY: linear (xi) SEQUENCE DESCRIPTION: SEQ ID NO: 32

Met Gly Leu Pro Ala Leu Leu Ala Ser Ala Leu Cys Thr Phe Val Leu
1               5                   10                  15

Pro Leu Leu Leu Phe Leu Ala Ala Leu Lys Leu Trp Asp Leu Tyr Cys
                20                  25                  30

Val Ser Ser Arg Asp Arg Ser Cys Ala Leu Pro Leu Pro Pro Gly Thr
            35                  40                  45

Met Gly Phe Pro Phe Phe Gly Glu Thr Leu Gln Met Val Leu Gln Arg
50                  55                  60

Arg Lys Phe Leu Gln Met Lys Arg Lys Tyr Gly Phe Ile Tyr Lys
65                  70                  75                  80

Thr His Leu Phe Gly Arg Pro Thr Val Arg Val Met Gly Ala Asp Asn
                85                  90                  95

Val Arg Ile Leu Leu Gly Glu His Arg Leu Val Ser Val His Trp
            100                 105                 110

Pro Ala Ser Val Arg Thr Ile Leu Gly Ala Gly Cys Leu Ser Asn Leu
            115                 120                 125

His Asp Ser Ser His Lys Gln Arg Lys Lys Val Ile Met Gln Ala Phe
            130                 135                 140

Ser Arg Glu Ala Leu Gln Cys Tyr Val Leu Val Ile Ala Glu Glu Val
145                 150                 155                 160

Ser Ser Cys Leu Glu Gln Trp Leu Ser Cys Gly Glu Arg Gly Leu Leu
                165                 170                 175

Val Tyr Pro Glu Val Lys Arg Leu Met Phe Arg Ile Ala Met Arg Ile
            180                 185                 190

Leu Leu Gly Cys Glu Pro Gly Pro Ala Gly Gly Gly Glu Asp Glu Gln
```

```
                195                 200                 205
Gln Leu Val Glu Ala Phe Glu Glu Met Thr Arg Asn Leu Phe Ser Leu
    210                 215                 220

Pro Ile Asp Val Pro Phe Ser Gly Leu Tyr Arg Gly Val Lys Ala Arg
225                 230                 235                 240

Asn Leu Ile His Ala Arg Ile Glu Glu Asn Ile Arg Ala Lys Ile Arg
                245                 250                 255

Arg Leu Gln Ala Thr Glu Pro Asp Gly Gly Cys Lys Asp Ala Leu Gln
            260                 265                 270

Leu Leu Ile Glu His Ser Trp Glu Arg Gly Glu Arg Leu Asp Met Gln
        275                 280                 285

Ala Leu Lys Gln Ser Ser Thr Glu Leu Leu Phe Gly Gly His Glu Thr
    290                 295                 300

Thr Ala Ser Ala Ala Thr Ser Leu Ile Thr Tyr Leu Gly Leu Tyr Pro
305                 310                 315                 320

His Val Leu Gln Lys Val Arg Glu Glu Ile Lys Ser Lys Gly Leu Leu
                325                 330                 335

Cys Lys Ser Asn Gln Asp Asn Lys Leu Asp Met Glu Thr Leu Glu Gln
            340                 345                 350

Leu Lys Tyr Ile Gly Cys Val Ile Lys Glu Thr Leu Arg Leu Asn Pro
        355                 360                 365

Pro Val Pro Gly Gly Phe Arg Val Ala Leu Lys Thr Phe Glu Leu Asn
370                 375                 380

Gly Tyr Gln Ile Pro Lys Gly Trp Asn Val Ile Tyr Ser Ile Cys Asp
385                 390                 395                 400

Thr His Asp Val Ala Asp Ile Phe Thr Asn Lys Glu Glu Phe Asn Pro
                405                 410                 415

Asp Arg Phe Ile Val Pro His Pro Glu Asp Ala Ser Arg Phe Ser Phe
            420                 425                 430

Ile Pro Phe Gly Gly Gly Leu Arg Ser Cys Val Gly Lys Glu Phe Ala
        435                 440                 445

Lys Ile Leu Leu Lys Ile Phe Thr Val Glu Leu Ala Arg His Cys Asp
450                 455                 460

Trp Gln Leu Leu Asn Gly Pro Pro Thr Met Lys Thr Ser Pro Thr Val
465                 470                 475                 480

Tyr Pro Val Asp Asn Leu Pro Ala Arg Phe Thr Tyr Phe Gln Gly Asp
                485                 490                 495

Ile
```

(2) INFORMATION FOR SEQ ID NO: 33

(i) SEQUENCE CHARACTERISTICS:
        (A) LENGTH: 273 base pairs
        (B) TYPE: nucleic acid
        (C) STRANDEDNESS: single
        (D) TOPOLOGY: linear
    (xi) SEQUENCE DESCRIPTION: SEQ ID NO: 33

```
CGCACCCCAG GAGGCGCGCT CGGAGGGAAG CCGCCACCGC CGCCGCCTCT GCCTCGGCGC      60

GGAACAAACG GTTAAAGATT TTGGGCCASC GCCTCCGCGG GGGGAGGAGC CAGGGGCCCC     120

AATCCCGCAA TTAAAGATGA ACTTTGGGTG AACTAATTGT CTGACCAAGG TAACGTGGGC     180

AGCAACCTGG GCCGCCTATA AAGCGGCAGC GCCGTGGGGT TTGAAGCGCT GGCGGCGGCG     240

GCAGGTGGCG CGGGAGGTCG CGGCGCGCCA TGG                                  273
```

-continued (2) INFORMATION FOR SEQ ID NO: 34

(i) SEQUENCE CHARACTERISTICS:
       (A) LENGTH: 274 base pairs
       (B) TYPE: nucleic acid
       (C) STRANDEDNESS: single
       (D) TOPOLOGY: linear (xi) SEQUENCE DESCRIPTION: SEQ ID NO: 34

```
CGCACCCCCA GGAGGCGCGC TCAGAGGGAA GCCGCCAGTG CGCCGCCTCT GCCTCGGCGC      60

GGAACAAACG GTTAAAGATT TTTTTGGGCA GCGCCTCGAG GGGGGAGGAG CCAGGGGCCC     120

GATCCGCAAT TAAAGATGAA CTTTGGGTGA ACTAATTTGT CTGACCAAGG TAACGTGGGC     180

AGTAACCTGG GCGGCCTTAT AAAGAGGGCG CGCGGCGGGG TTCGGAGCTA GGGAGGCGGC     240

GGCAGGTGGC GCGGGAGGCT GAAGCGTGCC ATGG                                274
```

(2) INFORMATION FOR SEQ ID NO: 35

(i) SEQUENCE CHARACTERISTICS:
       (A) LENGTH: 319 base pairs
       (B) TYPE: nucleic acid
       (C) STRANDEDNESS: single
       (D) TOPOLOGY: linear (xi) SEQUENCE DESCRIPTION: SEQ ID NO: 35

```
TCGGGGAAT TAACACCTTT TCAAAGTGAA ATCTCAGGAT TGTCTGCCTT CTACAGGAGG       60

TGGTATTAAA ATGCGCCTAT AACAAATGGT TGAGAGTTTG GAGCCGCTTC TGCCCTGTGG     120

GCGGGGCGAG ATGACACCAC AATTAAAGAT GAACTTTGGG TGAACTAATT TATCTGAGGA     180

AGTTAACAGG AGGAGACCTG CGCGCAATGG ATATATAAGG GCGCGCAGGC GAGGACGCCC     240

TCAGTTTGTG CGTAAAGACG CGTCTCCTCT CCAGAAGCTT GTTTTTCGTT TTGGCGATCA     300

GTTGCGCGCT TCAACATGG                                                 319
```

(2) INFORMATION FOR SEQ ID NO: 36

(i) SEQUENCE CHARACTERISTICS:
       (A) LENGTH: 2677 base pairs
       (B) TYPE: nucleic acid
       (C) STRANDEDNESS: single
       (D) TOPOLOGY: linear (xi) SEQUENCE DESCRIPTION: SEQ ID NO: 36

```
GATCCCAGAT CTGCCTATTG CGCCCGATGC CCCGAGGCTC TCTCTTGGAC TCTGGCCCTG      60

AGTTCTTCTG CGCGATCCTT CGGAGACGTC TGGAGGCCTG CTTTATGCAT CTCTCTTGGA    120

CCTCAGTTTC CCCACACGTG GGAGGAGGCA GCTGGACGAT TCCTGAAAGG ACTTTCCCTT    180

GCTTCCTCAT CACGTGGAAG AGAGCCCACC CGGCACCTGG AAATGGAAAG CCAGTGAAGG    240

CTGCTTTGGG CCGGGGCAKC GGGTGGGACC GGGCGGAGG GATTCCAAAG AGACCGCCGG     300

GAAGGCTAGA GCTTGGAATT CCGGCTCCTC GGAGTCCTGG CCCTCCCCCA CCGCCGCCTC    360

GGAGCTCAGC ACACCTTGGA TGGGGAGGC GGGCAGCTCC TAGCCCCGCA CCCCAGGAGG     420

CGCGCTCGGA GGGAAGCCGC CACCGCCGCC GCCTCTGCCT CGGCGCGGAA CAAACGGTTA    480

AAGATTTTGG GCCASCGCCT CCGCGGGGGG AGGAGCCAGG GGCCCAATC CCGCAATTAA     540

AGATGAACTT TGGGTGAACT AATTGTCTGA CCAAGGTAAC GTGGGCAGCA ACCTGGGCCG    600

CCTATAAAGC GGCAGCGCCG TGGGGTTTGA AGCGCTGGCG GCGGCGGCAG GTGGCGCGGG    660

AGGTCGCGGC GCGCCATGGG GCTCCCGGCG CTGCTGGCCA GTGCGCTCTG CACCTTCGTG    720

CTGCCGCTGC TGCTCTTCCT GGCTGCGATC AAGCTCTGGG ACCTGTACTG CGTGAGCGGC    780
```

```
CGCGACCGCA GTTGTGCCCT CCCATTGCCC CCCGGGACTA TSGGSTTCCC CTTCTTTGGG      840

GAAACCTTGC AGATGNTACT NCAGGTAAGG GAGGGTGGGG CGGGACAGGC TGCTTCCCCG      900

GAGCCCGGCG CGGCTCTGGG CTTCTGCTGA AGTCGGGGTA GGCGCCCCCG GGAGGCATGC      960

TATTGCGGCT AGGAGCAGGG CTGGCGGGAG CGCGGCGCTC CCCGGMKYMC SCTCAWGCSC     1020

RCWWKTMWCC TCCGCCTYMC TCCCAMAGCG GARSAARWKC YKGMRGATGA AGCGCAGGAA     1080

ATACGGCTTC ATCTACAAGA CGCATCTGTT CGGGCGGCCC ACCGTACGGG TGATGGGCGC     1140

GGACAATGTG CGGCGCATCT TGCTCGGAGA GCACCGGCTG GTGTCGGTCC ACTGGCCAGC     1200

GTCGGTGCGC ACCATTCTGG GATCTGGCTG CCTCTCTAAC CTGCACGACT CCTCGCACAA     1260

GCAGCGCAAG AAGGTGGGGG CAGGAGGCGA CGGCTGGACA GGGAGGGGGA CCCCATTTAT     1320

GAGCGGAATT CCGGCTGATG GATGCTAGGC GCGGGCTAGC AGCTTGAGGT GGGCTAGGAC     1380

CCTCTGCCAG CTCCAGGTTA GCTTTCCCAG CTCGGAGAGT GCCATGTGTC TGGCAGGACT     1440

GGGGGTGTCT GGAAGGGGAC GGCGGTAGAC GAGAGGGGCG GATGGAGGCT TTTAACGCTG     1500

TCCCCTCCTC GGGACTCAGG TGATTATGCG GGCCTTCAGC CGCGAGGCAC TCGAATGCTA     1560

CGTGCCGGTG ATCACCGAGG AAGTGGGCAG CAGCCTGGAG CAGTGGCTGA GCTGCGGCGA     1620

GCGCGGCCTC CTGGTCTACC CCGAGGTGAA GCGCCTCATG TTCCGAATCG CCATGCGCAT     1680

CCTACTGGGC TGCGAACCCC AACTGGCGGG CGACGGGGAC TCCGAGCAGC AGCTTGTGGA     1740

GGCCTTCGAG GAAATGACCC GCAATCTCTT CTCGCTGCCC ATCGACGTGC CCTTCAGCGG     1800

GCTGTACCGG GTAAGGGCGG CAAACGGGCT GCGGACTAGG GGCGCGGGAC CTGGGCGTCT     1860

GCTCACCGCC GCGCGCTCTC TGCGCTCAGG GCATGAAGGC GCGGAACCTC ATTCACGCGC     1920

GCATCGAGCA GAACATTCGC GCCAAGATCT GCGGGCTGCG GCATCCGAG GCGGGCCAGG     1980

GCTGCAAAGA CGCGCTGCAG CTGTTGATCG AGCACTCGTG GGAGAGGGGA GAGCGGCTGG     2040

ACATGCAGGT GAGTAGCAGC TTCAGACCAG GCACTGCGGA GTTTGGTCCC CTGGCTTTCC     2100

AAGGCGCTGT TCCTGGGGCC CCCAAAGCGC GCGCCTGGGG CCCAGCTTTC TGGAGTGGGC     2160

GGCCGGCTCA GACTACAGCT ATGGAATCCC GAAGGAAGGC TGAGACACCC GGTCAGGAGA     2220

GCTGCGGAAG GGGCTGCGGM GGAAACTGGG AGCATCCCCT AGCCTTTAMC AGGTTTCAAA     2280

GGGAAAGTTG GAATTTGCAA AAATGTTAAT AAAGAACCTT GCGATTTTAA TAAAACTAAG     2340

ACTTTAACTC AGGAGTTTCC GGTAGRGCGG GGTCGTACTC GCCTTACTGC TCCAGCTGAA     2400

CTAAAGGGAC GTTGCATTTT GTTTAAAGAT ATTGCTTTCC TTGACTTTCT GTCAGCAAAA     2460

CATTTAGCCC TTCTAGTCTT CCCTCCAGAA CTCTCAGTTC GATTCTGAGT AATCCTTCTG     2520

TCAAACCGCA GGCAGACTTG TGAGAATGTG GGTCTCACTC TATTCTTAGG CACTAAAGCA     2580

ATCTTCAACC GAACTCCTCT TTGGAGGACA CGAAACCACG GCCAGTGCAG CCACATCTCT     2640

GATCACTTAC CTGGGCTCT ACCCACATGT TCTCCAG                              2677
```

(2) INFORMATION FOR SEQ ID NO: 37

(i) SEQUENCE CHARACTERISTICS:
        (A) LENGTH: 683 base pairs
        (B) TYPE: nucleic acid
        (C) STRANDEDNESS: single
        (D) TOPOLOGY: linear (xi) SEQUENCE DESCRIPTION: SEQ ID NO: 37

```
GATCCAGGTT GCTGAAACAT ATCTCCATAT AGGGCAGAAC AATTATCAAA AGCATAAGAA       60

TTGCAGCCAC AGCATAGGGA AGAAAGAGGA GTTTTTAAAC CACAACAAAA GGGAGAAAGA      120
```

```
AGAGAATTTT AACTTACATT TAATTCAAAA GTCTTCAGAG CAACCCGAAA CCCTCCTGGA      180

ACTGGGGGAT TCAGTCGAAG GGTCTCCTTA ATAACACACC CGATGTATYT AAGTTGTTCC      240

AAAATTTCCA TGTCCAACTT GTTGTCTTGA TTGCTCTTGC AAAGTAAACC CTAYCAAAAY      300

AGTCATACAG AGGTGAACAG TYATTTTGTG CTCCAATTAA AATCAGCCCA GCAGACGTAA      360

ACAGGGCTTA AGTGGAGACT AAACCCAAAG GGCCCCATGA TGGGAGAGAC TGGGAGGGGG      420

AAACAGCAGC TAATGGCCAT TTGCCTGCCC AAATCCACTA TCTATTTACA ATCCCAGGAG      480

AATGCTGCTC ACCAGTTAGA AGGACCAAGT TTCTCCCCAC GCCCCCCCAC CCCACACTCA      540

CCACCACCAC CCACACTAAT CAGCTATTCA CACTATGTAT GCCCTTGGAC ACACCAATTC      600

AAGAAAAGTG GAACCTATCT GAGAATCTCC ACGGTTCACA AAAGGTGGA GGAGGGGTAG       660

GAATACAAGG TCAAACCCTG CCC                                              683

(2) INFORMATION FOR SEQ ID NO: 38

(i) SEQUENCE CHARACTERISTICS:
        (A) LENGTH: 4164 base pairs
        (B) TYPE: nucleic acid
        (C) STRANDEDNESS: single
        (D) TOPOLOGY: linear (xi) SEQUENCE DESCRIPTION: SEQ ID NO: 38

TCGCGAGGAG CGACCACGGC TTGAAGAGGG GTAGACGAGA CCAGATGCTC CCCGGCGCCC       60

CCTCATGCGG GTTGCGGTCT CTCTCCTCCA CCTCCCTCTC AGCGGAGGAA GTTTCTGCAG      120

ATGAAGCGCA GGAAATACGG CTTCATCTAC AAGACGCATC TGTTTGGGCG GCCCACGGTG      180

CGGGTGATGG GCGCGGATAA TGTGCGGCGC ATCTTGCTGG GAGAGCACCG GTTGGTGTCG      240

GTGCACTGGC CCGCGTCGGT GCGCACCATC CTGGGCGCTG GCTGCCTCTC CAACCTGCAC      300

GATTCCTCGC ACAAGCAGCG AAAGAAGGTG AGGGTGAGCT GGCAACTCCT TGGCTGGCAG      360

GGAGACCTCA TCCTATGGCT TGGTTCAGGC AAAATAGAAT GCGGGGCGAG GGCTAGTCCT      420

ATGTGGTGGG GACCAGGACC CTCTCTATCT GAGATCCACT TTAGCTTTTC TGCTAGCACG      480

TGGGTTAGTC CTGGGGGGGA CTGAAATTCT TGAAAGGGTA CTCGGAAAGG CGAAGGGGGG      540

GGGGCTGAGG GAAAGTAGAG GATTGTAACA CTCTCTGCTC CTGGGGGGTG CTCAGGTGAT      600

TATGCAGGCC TTCAGCCGCG AGGCACTCCA GTGCTACGTG CCCGTGATCG CTGAGGAAGT      660

CAGCAGTTGT CTGGAGCAGT GGCTAAGCTG CGGCGAGCGC GGCCTCCTGG TCTACCCCGA      720

GGTGAAGCGC CTCATGTTCC GCATCGCCAT GCGCATCCTG CTGGGCTGCG AGCCGGGTCC      780

AGCGGGCGGC GGGGAGGACG AGCAGCAGCT CGTGGAGGCT TTCGAGGAGA TGACCCGCAA      840

TCTCTTCTCT CTTCCCATTG ACGTGCCCTT TAGCGGCCTG TACCGGGTAA GGGCGGTTTG      900

CGGAGTCGGA GTAGGGGAAC GCAAGCTCGG GCATCCGCTC ACCGCCACGC TCTCTCCGCG      960

CTCAGGGCGT GAAGGCGCGG AACCTTATAC ACGCGCGCAT CGAGGAGAAC ATTCGCGCCA     1020

AGATCCGCCG GCTTCAGGCT ACAGAGCCGG ATGGGGGTTG CAAGGACGCG CTGCAGCTCC     1080

TGATTGAGCA CTCGTGGGAG AGGGGAGAGA GGCTGGATAT GCAGGTGAGA AGCAATTTCA     1140

AAAGGTGCCA AGGGCCGGGG AGTGCCTCTG ACTTTCCAGA CACACTTTCT GGGGTCTCCA     1200

AAGCCCTGTC AAGGCCCCAG CTACTTCCAA GTGGGCGGCG ATGCTAGGTC TAGAGCTTTT     1260

CAACCTGTGG GTCGTGACCC CTTCACGGAG CCAAACAACC CTTTCAGAAG GGTCGCCTAA     1320

GAGCATCTGC ATATCCGATA TTTACATCAA GAAACATAAC AGTAGCAAAA TTACCGTTAT     1380

GAAGTAGCAA CAAAGATAAT TTATCGTTGG GGGGTCACCA CAACACGAGG AACCGTATTA     1440
```

```
AAGGGTGGCA TTGGTCTAGA GAGCTGTGGA AGGGGGTGGC TGAGCAATGG GGAAGATCCC    1500

AAAGTTCAAA GGGCAAGGCT CATCTACAAA GGTTAAAGCG GAAGAGCAGG ATTAAGGGAG    1560

TTTTGCGTTT TTGTTTGTGG TCTTTGACTT TCTATGAACA AAACGGATTT TACCCTTGAA    1620

GTCTTCCGTG CAATATTCTC AGGTCAGGTC TTTGTAACAG TGCTATAAAC TGCACTCAGA    1680

TCTGTATAAA CTTCCGTTTT TATCCTTAGG CACTAAAACA ATCGTCAACA GAGCTCCTCT    1740

TTGGTGGTCA TGAAACTACA GCCAGTGCTG CGACGTCACT GATCACTTAC CTAGGACTCT    1800

ACCCACATGT CCTCCAGAAA GTTCGAGAAG AGATAAAGAG CAAGGTAGGA TGATTCTAGA    1860

GGTTCCCCAT TTGCCTAGGA CATTCCTCTA TTAACCACCA CCACCACCCC CACTGTATAT    1920

AAGTTTGCTC GATACACCCA GTACTATGAC AGTGAAGATC TGAGAGCTAG GTGGACTGT    1980

GGGGGAGAGA CTCCACCTCG TGAATTTAAA AAGGCAGTTG TTTGTACTGG GCTCTCTCTT    2040

GGGCAGAATT TGACCCTCTC CTCCTCCTCC TCCTCCTCCT CCTCTTCCTC CTCCACCACC    2100

ACCACCATCA CCACCTTTTA TAGAGCAAGG TTCTCCTTTC CCTGACCAAG AACATGAATA    2160

ATGTGATTAG AGCCAATAGC TGATCAGGGT CGCAGTGTTG GTGAGGGCTC AGGGTATGAC    2220

CCTTTATATA CCTGATAAGC AACATTGTCT GGATAATGGG TTTAGGCTGA GGAAGTGTGG    2280

AAAGGAAGGC CATCAGGCCA TCAGCTCTTT CCCTTTTATC CTCTCCCATC CAGACGCCTT    2340

CAGGTTTAGT TAACAGGTGA GTCCTGCTGG GCTGACTTTT TTTTTGGAGT GCCCAGGGAT    2400

CCATCACTCA CTTTTTTATC TGTTTCCATA GGGCTTACTT TGCAAGAGCA ATCAAGACAA    2460

CAAGTTAGAC ATGGAAACTT TGGCACAGCT TAAATACACT GGGTGTGTCA TTAAGGAGAC    2520

CCTGCGATTG AATCCTCCGG TTCCAGGAGG GTTTCGGGTT GCTCTGAAGA CTTTTGAGCT    2580

GAATGTGAGT GCACCTCCTG TCCCCCACCC CCAGCCCTCG TCCACGTCCA CTCTGCTATG    2640

CTGTTGAGCA TCAGCTGCCC AGAGCAGTGG CTCACTGCCC TTGACAGTGT CCTGCCTCCT    2700

ATGGTACTGG GAACCAATTT GCTCTCCTCT CTTAATGCCA TCCATGCTAG TAATGACTTT    2760

TTGTTGTTGC AAGCTCAGGG CCGGGATTGT CAATTCTTAG GATTTTTTTT TTTTTTTAAA    2820

CAGGGATACC AGATCCCCAA GGGCTGGAAT GTTATTTACA GTATCTGTGA CACCCACGAT    2880

GTGGCAGATA TCTTCACTAA CAAGGAGGAA TTTAATCCCG ACCGCTTTAT AGTGCCTCAT    2940

CCAGAGGATG CTTCCCGGTT CAGCTTCATT CCATTTGGAG GAGGCCTTCG GAGCTGTGTA    3000

GGCAAAGAGT TTGCAAAAAT TCTTCTTAAG ATATTTACAG TGGAGCTGGC TAGGCACTGT    3060

GATTGGCAGC TTCTAAATGG ACCTCCTACA ATGAAGACAA GCCCCACTGT GTACCCTGYG    3120

GACAATCTCC CTGCAAGATT TACCCACTTC CAGGGAGATA TCTGATAGCT ATTTCAATTC    3180

TTGGACTTAT TTGAAGTGTA TATTGTTTTT TTTAAAATAG TGTCATGTTG ACTTTATTTA    3240

ATTTCTAAAT GTATAGTATG ATATTTATGT GTCTCTACTA CAGTCCCGTG GTCTTAAATA    3300

TTAAAATAAT GAATTTGTAT GATTTCCCAA TAAAGTAAAA TTAAAAAGTG CTTCTCTTGC    3360

TTTTTAAGAT TCTTGTTGGC AAGCTGCCCA TGGTGGTACA TTGCTGTAAT ACTAGGACTT    3420

GGAAGGTGGA GGCAAGAAGA GCAGGCATTC AAGGCTAGCC TGGGCTACAG AAATCCTGTC    3480

TTAAACAAAC ACTACAACAA AAAGTCCTGT TAGGGAATCT GACTGGCTCA GTGTTTGTAC    3540

TTTGTGTATT TAAATGATT TAGAGTGAAA CCATAGGTCT CTCCCCCATG TCAGAAAATA    3600

TATATTATTA TGTGTATGCT GATCCAAAGT ATCTTTGTAA CTTTTTCTAA GGTCATTGAG    3660

ACTTCATATT TTGAAATTGT ATGGAGGCTA GTTATATTAC ATTATTTATT TATTTATTTA    3720

TTTACATTTT TATGGTGCTG GGATTGGAT CGAAGGCTTC ACACCTCTAG GGCAAGCCCT    3780
```

```
TTGTCATTAA GGCGCTGCCT CTCCCTTTCA GCCCAACGTT AATTCTAGAT TCTTTTTCTT    3840

TGGTGCTTTT GGGAGGTAAA CCTGGGATGC TGCAGTTATT TGGTGGTGGT CGTTGGTTTT    3900

ACTCTAGAGA GAAGGCAACT TTGGGAAGGC AACACTGCTG CTGGTGAGTC GGGAAGCATC    3960

ATCCCAGAGC AACGGGGTCA GCATAGCTAA CATTTTAAAT CAGCATAATG AATCCCTGTC    4020

ATATGGAGGA GGCAGAACTC CTCTTTGAAG TTGATATTTT AGATAAGACA GAGCCAGCCC    4080

CTCTGGTTAT GGACAGTTCT TACCCAAAAT GAAACAGAGA AGAAAACCAC TGGTGTGTCA    4140

CCTTTCCTTA GAAGTGCTTC AGGA                                          4164

(2) INFORMATION FOR SEQ ID NO: 39

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ix) FEATURE:
        (D) OTHER INFORMATION: Each N can represent any nucleotide
            and there can be 0 to 5 N (xi) SEQUENCE DESCRIPTION: SEQ ID NO: 39

TGAACTNNNNNTGAACT                                                   17

(2) INFORMATION FOR SEQ ID NO: 40

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 40

TCTGASSAAG KTAAC                                                    15

(2) INFORMATION FOR SEQ ID NO: 41

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 41

CAATTAAAGA                                                          10

(2) INFORMATION FOR SEQ ID NO: 42

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 42

CAATTAAAGA TGAACTTTGG GTGAACTAAT T                                  31

(2) INFORMATION FOR SEQ ID NO: 43

(i) SEQUENCE CHARACTERISTICS:
        (A) LENGTH: 15 base pairs
        (B) TYPE: nucleic acid
        (C) STRANDEDNESS: single
        (D) TOPOLOGY: linear
```

-continued (xi) SEQUENCE DESCRIPTION: SEQ ID NO: 43

GTAGCACGGA TGGTG                                                                                   15

RETINOID METABOLIZING PROTEIN

This application is a divisional application of U.S. patent application Ser. No. 08/882,184, filed Jun. 25, 1997, now U.S. Pat. No. 6,306,624, which application is a continuation-in-part application of No. PCT/CA97/00440 filed on Jun. 23, 1997 through the Canadian Intellectual Property Office as Receiving Office and designating the United States, and a continuation-in-part application of U.S. patent application Ser. No. 08/724,466, filed Oct. 1, 1996, now U.S. Pat. No. 6,063,606 which application is a continuation-in-part application of U.S. patent application Ser. No. 08/667,546, filed Jun. 21, 1996, abandoned, the specifications of which applications are incorporated herein by reference.

BACKGROUND OF THE INVENTION

Vitamin A metabolism gives rise to several active forms of retinoic acid (RA) which are involved in regulating gene expression during development, regeneration, and in the growth and differentiation of epithelial tissues [Maden, 1992; Chambon, 1995; Mangelsdorf, 1995; Gudas, 1994; Lotan, 1995; Morriss-Kay, 1996]; has been linked apoptosis, or programmed cell death in a number of cell types; and to have anticarcinogenic and antitumoral properties [Lotan, 1996].

Early studies of retinol deficiency indicated a correlation between vitamin A depletion and a higher incidence of cancer and increased susceptability to chemical carcinogenesis [Chytil, 1984]. Several animal models have been used to demonstrate the effectiveness of retinoids in supressing carcinogenesis in a variety of tissues including skin, mammary epithelia, oral cavity, aerodigestive tract, liver, bladder and prostate [Moon, 1994]. These studies have led to the preventative use of retinoids to treat premalignant lesions including actinic keratosis and oral leukoplakia, as well as in the prevention of secondary tumours of the head and neck and the recurrence of non-small cell lung carcinomas, and basal cell carcinomas [Hong, 1994; Lippman, 1995]. RA itself has been found to be useful therapeutically, notably in the treatment of cancers, including acute promyelocytic leukemia (APL), tumors of the head and neck, and skin cancer, as well as in the treatment of skin disorders such as the premalignancy associated actinic keratoses, acne, psoriasis and ichthyosis. There is evidence that the effectiveness of RA as an anti-tumour agent is at least partially due to induction of cellular differentiation and/or inhibition of proliferation [Lotan, 1996]. Studies over the past several years indicate that a high proportion of patients with acute promyelocytic leukemia (APL) achieve complete remission after a short period of treatment with all-trans RA. Unfortunately, this high rate of remission is in most cases brief. Following relapse, patients are clinically resistant to further treatment with RA [Warrell, 1994; Warrell, et al., 1994; Chomienne, 1996; Muindi, 1992]. The nature of this resistance is unknown. Interestingly, leukemic cells taken from patents exhibiting clinical resistance to RA have been shown to be sensitive to the differentiating action of RA when grown in vitro (Muindi, 1992; Muindi, 1994). This suggests that pharmacokinetic mechanisms may account for the acquired resistance to RA. This possibility is supported by studies showing that peak plasma concentrations of RA were much higher in patients after initial administration than in patents treated following relapse. This decrease in peak plasma RA concentration was accompanied by a 10-fold increase in urinary 4-oxo-retinoic acid concentration. In addition, ketoconazole, a broad spectrum inhibitor of cytochrome P450 function was shown to modulate RA pharmacokinetics in vivo [Muindi, 1992; Muindi, 1994]. It is therefore likely that RA increases the rate of its own metabolism which in turn results in the inability to sustain effective therapeutic doses of RA. Therapeutic administration of RA can result in a variety of undesirable side effects and it is therefore important to establish and maintain the minimal requisite doses of RA in treatment. For example, RA treatments during pregnancy can lead to severe teratogenic effects on the fetus. Adverse reactions to RA treatment also include headache, nausea, chelitis, facial dermatitis, conjunctivitis, and dryness of nasal mucosa. Prolonged exposure to RA can cause major elevations in serum triglycerides and can lead to severe abnormalities of liver function, including hepatomegaly, cirrhosis and portal hypertension.

RA metabolism may also account for the lack of response of certain tumors to RA treatment. For example, recent studies have shown that cytochrome P450 inhibitors that block RA metabolism, resulting in increased tissue levels of RA, may be useful therapeutic agents in the treatment of prostate cancer [Wouters, 1992; De Coster, 1996]. Thus RA metabolizing cytochrome P450s may be useful targets for the treatment of a number of different types of cancer.

The classical view of vitamin A metabolism holds that all trans-RA, the most active metabolite is derived from conversion of retinol to retinaldehyde to RA through two oxidation steps and that RA is further metabolized to the polar derivatives 4-OH RA and 4-oxo RA [Blaner, 1994; Napoli, 1995; Formelli, 1996; Napoli, 1996]. It is unknown whether the 4-oxo- and 4-OH- metabolites are simply intermediates in the RA catabolic pathway or whether they can also have specific activities which differ from those of all-trans RA and 9-cis RA. Pijnappel et al. [Pijnappel, 1993] have shown that, in Xenopus, 4-oxo-RA can efficiently modulate positional specification in early embryos and exhibits a more potent ability to regulate Hoxb-9 and Hoxb-4 gene expression than all-trans RA. 4-oxo-RA has been found to bind to retinoic acid receptor-$\beta$ (RAR-$\beta$) with affinity comparable to all-trans RA [Pijnappel, 1993] but poorly to RAR-$\gamma$ [Reddy, 1992], suggesting that this metabolite exhibits some receptor selectivity. 4-oxo-RA also binds to cellular retinoic acid binding protein (CRABP) but with an affinity slightly lower than that of all-trans RA [Fiorella, 1993]. Takatsuka et al. [Takatsuka, 1996] have shown that growth inhibitory effects of RA correlate with RA metabolic activity but it is unknown whether there is a causal relationship between production of RA metabolites and growth inhibition. The asymmetric distribution of these metabolites in developing embryos suggests that they may be preferentially sequestered or generated by tissue specific isomerases [Creech Kraft, 1994]. The normal balance of these metabolites is dependent upon rate of formation from metabolic precursors, retinol and retinaldehyde [Leo, 1989], and rate of catabolism. Little is presently known about the enzymes involved in this metabolic scheme, in particular the catabolism of RA.

The catabolism of RA is thought to be initiated by hydroxylation either at the C4-, or C18-position of the $\beta$-ionone ring of RA [Napoli, 1996]. The C4- hydroxylation step is mediated by cytochrome P450 activity, as judged by the ability of broad spectrum P450 inhibitors such as ketocoazole and liarazole to block 4-hydroxylation [Williams, 1987, Van Wauwe, 1988; Van Wauwe, 1990, Van Wauwe, 1992, Wouters, 1992]. In certain tissues, including testis, skin and lung and in numerous cell lines, such as NIH3T3 fibroblasts, HL 60 myelomonocytic leukemic cells, F9 and P19 murine embryonal carcinoma cell lines and MCF7, RA metabolism can be induced by RA pretreatment [Frolik, 1979, Roberts, 1979a and b; Duel, 1992; Wouters, 1992]. Studies involving targetted disruption of RAR genes in F9 cells suggest that RARE and RAR-γ isoforms may play a role in regulating the enzymes responsible for this increased metabolism [Boylan, 1995].

The glucuronidation of RA is a significant metabolic step in the inactivation of RA [Blaner, 1994; Formelli, 1996]. The elimination of RA may require oxidation to 4-oxo, followed by conjugation to form the 4-oxo all-trans RA glucuronide. This is supported by studies in both primates and humans showing that the 4-oxo RA glucuronide is the only retinoid conjugate found in urine [Muindi, 1992; Muindi, 1994]. The fact that following RA therapy, 4-oxo RA is not present or barely detectable in serum, suggests that oxidation may be the rate limiting step in this process.

It has recently been shown that 4-oxoretinol (4-oxo-ROL) can have greater biological activity than retinol. The 4-oxo-ROL is inducible by RA in F9 and P19 mouse teratocarcinoma cells [Blumberg et al., 1995; Achkar et al., 1996].

It is known that zebrafish fins regenerate through an RA sensitive process which utilizes many gene regulatory pathways involved in early vertebrate development [White, 1994; Akimenko, 1995a & b].

As far as the inventors are aware, cytochrome P450s involved in the metabolism of RA in extrahepatic tissues remain uncharacterized at the molecular level.

SUMMARY OF THE INVENTION

The present inventors are the first to identify, clone and sequence a gene (cDNA) encoding a retinoic acid-inducible, retinoic acid-metabolizing protein, including a cDNA which is RA-inducible in humans. The protein has been found to be expressed in epithelia.

A cDNA has been isolated from zebra fish and sequenced. A protein encoded by the cDNA has been expressed and shown to have the ability to hydroxylate retinoic acid at the 4 position of the β-ionone ring of retinoic acid. The protein has been found to be inducible in epithelial cells exposed to retinoic acid.

A human cDNA encoding a protein with similar functionality has also been isolated and sequenced.

A cDNA has also been isolated from mouse and sequenced.

Homology between sequences from the three species, be they nucleic acids encoding the protein, or the amino acid sequences of the proteins, has been found to be relatively high and all three proteins contain a heme-binding motif characteristic of the group of proteins known as cytochrome P450s. The overall homology between the amino acid sequences of these newly obtained proteins and known cytochrome P450s is less than 30%. Notwithstanding this relatively low overall homology, a higher degree of homology has been observed in the heme binding region for certain other P450s. For example, homology between the approximately 20 amino acids defining respective heme binding regions of the new zebrafish protein and CYP4503A12 is about 50% and between the new zebrafish protein and hCYTFAOH is 65%. The homology between the home binding region itself of a protein of the present invention and another P450 could well be 70%, 75%, 80%, 85%, 90%, 95% or even 100%.

A first aspect of the present invention is thus a purified protein having the ability to oxidize a retinoid, and having an amino acid sequence which is at least about 30% conserved in relation to the amino acid sequence identified as SEQ ID NO:2 or identified as SEQ ID NO:4 or identified as SEQ ID NO:32, or a functionally equivalent homolog thereof. The amino acid sequence identified as SEQ ID NO:2 is of the protein, termed here "zP450RAI", obtained from zebrafish. The amino acid sequence of the human protein is identified as SEQ ID NO:4 and the protein is referred to herein as "hP450RAI". The sequence of the mouse protein is identified as SEQ ID NO:32 and the protein is referred to herein as mP450RAI.

Such a protein which is at least about 35% conserved in relation to the amino acid sequence identified as SEQ ID NO:2 (zebrafish) or identified as SEQ ID NO:4 (human) or identified as SEQ ID NO:32 (mouse), or a functionally equivalent homolog thereof, also forms part of the invention disclosed herein. Likewise, the degree of sequence conservation of a protein could be 40%, 45%, 50%, 55%, 60%, 65%, 70%, 75%, 80%, 85%, 90%, 95% or of course 100% of either SEQ ID NO:2 or SEQ ID NO:4 or SEQ ID NO:32 or a functionally equivalent homolog thereof, variants being possible so long as the ability of the native protein to oxidize a retinoid is retained. Also within the scope of the invention is any such protein which has the ability to hydroxylate retinoic acid at the 4 position of the β-ionone ring. Of course, conservatively substituted variants of proteins disclosed are within the scope of the present invention.

A retinoid oxidized by a protein of the present invention may be a retinoic acid or a retinol and the protein may have the ability to oxidize the carbon occupying the 4-position of the β-ionone ring of the retinoid. In particular all-trans retinoids may be metabolized by proteins of the present invention.

In the context of this specification, the term "conserved" describes similarity between sequences. The degree of conservation between two sequences can be determined by optimally aligning the sequences for comparison, as is commonly known in the art, and comparing a position in the first sequence with a corresponding position in the second sequence. When the compared positions are occupied by the same nucleotide or amino acid, as the case may be, the two sequences are conserved at that position. The degree of conservation between two sequences is often expressed, as it is here, as a percentage representing the ratio of the number of matching positions in the two sequences to the total number of positions compared.

The generic term "retinoids" means a group of compounds which includes retinoic acid, vitamin A (retinol) and a series of natural and synthetic derivatives that can exert profound effects on development and differentiation in a wide variety of systems. For purposes of this disclosure "retinoid" is also intended to encompass an equivalent thereof having the same functional characteristics which may be produced, for example, by computational chemistry.

In another aspect, the present invention is an isolated nucleic acid molecule encoding a protein of the present invention.

The present invention thus includes an isolated nucleic acid molecule encoding a protein having an amino acid sequence which is at least about 30% conserved in relation to the amino acid sequence identified as SEQ ID NO:2 or identified as SEQ ID NO:4 or identified as SEQ ID NO:32, or a functionally equivalent homolog thereof, for example, or a nucleic acid strand capable of hybridizing with the nucleic acid molecule under stringent hybridization conditions. Of course, the degree of conservation of the protein which the nucleic acid encodes can be higher, that is, 35%, 40%, 45%, 50%, 55%, 60%, 65%, 70%, 75%, 80%, 85%, 90%, 95% or more.

Particularly, the invention is an isolated nucleic acid molecule encoding a protein having the ability to oxidize a retinoid at the carbon occupying the 4-position of the β-ionone ring of the retinoid ring, and more particularly, having all-trans retinoic acid 4-hydroxylase activity. For the purposes of this invention, the term "isolated" refers to a nucleic acid that is substantially free of other cellular material or culture medium when produced by recombinant DNA techniques, or chemical precursors or other chemicals when produced by chemical synthesis.

Cellular expression of preferred proteins of the present invention, preferred embodiments being described in more detail below, can for certain types of cells be induced by exposure of the cells to a retinoid, particularly, retinoic acid. A protein of the present invention, when described as being a "retinoic acid inducible protein", is a protein normally encoded by DNA of a cell and whose expression by that cell can be induced by exposure of the cell to retinoic acid. It will be appreciated that not every cell, even if it contains DNA encoding such a protein, possesses all the attributes necessary to express the protein on exposure to RA.

Nucleotide sequences possessing promoter activity associated with the proteins have also been isolated and identified by the inventors. The human nucleotide sequence having promoter activity is identified as SEQ ID NO:33. The murine nucleotide sequence having promoter activity is identified as SEQ ID NO:34. The zebrafish nucleotide sequence having promoter activity is identified as SEQ ID NO:35.

In fact, the invention includes genomic sequences for the human (SEQ ID Nos:36 and 37) and mouse (SEQ ID NO:38).

In another respect, the present invention is thus a microbial cell containing and expressing heterologous DNA encoding a retinoic acid inducible protein having all-trans retinoic acid 4-hydroxylase activity.

The sequence of a nucleic acid molecule of the present invention can correspond to a part of a human genome or of a fish genome or of a mouse genome, or vary therefrom due to the degeneracy of the genetic code. More particularly, a nucleic acid molecule of the present invention having the sequence identified as SEQ ID NO:3 (zP450RAI) or SEQ ID NO:5 (hP450RAD, or SEQ ID NO:31 (mP450RAI), or the sequence can be one which varies from one of these sequences due to the degeneracy of the genetic code, or it can be a nucleic acid strand capable of hybridizing with at least one of these nucleic acid molecules under high or low stringency hybridization conditions.

"Stringent hybridization conditions" takes on its common meaning to a person skilled in the art here. Appropriate stringency conditions which promote nucleic acid hybridization, for example, 6× sodium chloride/sodium citrate (SSC) at about 45° C. are known to those skilled in the art. The following examples are found in Current Protocols in Molecular Biology, John Wiley & Sons, NY (1989), 6.3.1–6.3.6: For 50 ml of a first suitable hybridization solution, mix together 24 ml formamide, 12 ml 20×SSC, 0.5 ml 2 M Tris-HCl pH 7.6, 0.5 ml 100× Denhardt's solution, 2.5 ml deionized $H_2O$, 10 ml 50% dextran sulfate, and 0.5 ml 10% SDS. A second suitable hybridization solution can be 1% crystalline (fraction V), 1 mM EDTA, 0.5 M $Na_2HPO_4$ pH 7.2, 7% SDS. The salt concentration the wash step can be selected from a low stringency of about 2×SCC at 50° C. to a high stringency of about 0.2×SSC at 50° C. Both of these wash solutions may contain 0.1% SDS. In addition, the temperature in the wash step can be increased from low stringency conditions at room temperature, about 22° C., to high stringency conditions, at about 65° C. The cited reference gives more detail, but appropriate wash stringency depends on degree of homology and length of probe. If homology is 100%, a high temperature (65° C. to 75° C.) may be used. If homology is low, lower wash temperatures must be used. However, if the probe is very short (<100 bp), lower temperatures must be used even with 100% homology. In general, one starts washing at low temperatures (37° C. to 40° C.), and raises the temperature by 3–5° C. intervals until background is low enough not to be a major factor in autoradiography.

Another aspect of this invention is isolated mRNA transcribed from DNA having a sequence encoding a protein of the present invention.

In another aspect, the present invention is isolated DNA having a sequence according to a nucleotide sequence described above operatively linked in a recombinant cloning vector. In the context of this invention, the two-part term "operatively linked" means both that the regulatory sequence contains sufficient element(s) to allow expression of the nucleic acid in question and that the nucleic acid is linked to the regulatory sequence appropriately. For example, the nucleic acid of the invention is in the appropriate orientation and in phase with an initiation codon. The present invention thus includes a stably transfected cell line which expresses a protein having the ability to hydroxylate retinoic acid at the 4 position of the β-ionone ring of retinoic acid. The invention includes a culture of cells transformed with a recombinant DNA molecule having a nucleic acid sequence which encodes a protein having the ability to hydroxylate retinoic acid at the 4 position of the β-ionone ring of retinoic acid.

Another aspect of the present invention is a host cell that has been engineered genetically to produce a protein of the invention described above, the cell having incorporated expressibly therein heterologous DNA encoding said protein. The cell may be selected such that production of the protein is inducible by exposing the cell to a retinoid, preferably, retinoic acid. The cell can be eukaryotic.

The present invention also includes a process for producing an above-described protein of the invention. Such a process includes:
preparing a DNA fragment containing a nucleotide sequence which encodes the protein;
incorporating the DNA fragment into an expression vector to obtain a recombinant DNA molecule which contains the DNA fragment and is capable of undergoing replication;
transforming a host cell with the recombinant DNA molecule to produce a transformant which can express the protein;
culturing the transformant to produce the protein; and
recovering the protein from resulting cultured mixture.

The present invention includes an antibody to a protein of the invention. Here, the term "antibody" is intended to include a Fab fragment and it can be a monoclonal antibody. The antibody can be specifically raised to the amino acid sequence identified as SEQ ID NO:4, i.e., hP450RAI.

The present invention includes a purified protein for use in metabolizing retinoic acid in an organism or cell in need of such metabolizing. Likewise, the invention includes a method for metabolizing retinoic acid in an organism or cell in need of retinoic acid metabolizing wherein the method includes administering a protein of the invention as described above.

The invention includes a method for inhibiting retinoic acid hydroxylation in an organism in need of such inhibition, comprising introducing into cells of the organism an effective amount of an antisense RNA or oligonucleotide substantially complementary to at least a portion of the sequence identified as SEQ ID NO:5. The organism can be human and/or the organism can be in need of treatment against a cancerous disease or a disease selected from the group consisting of cancer, actinic keratosis, oral leukoplakia, a secondary tumor of the head and/or neck, a non-small cell lung carcinoma, a basal cell carcinoma, acute promyelocytic leukemia, skin cancer, and a premalignancy associated actinic keratosis, acne, psoriasis and/or ichthyosis. Such a method can include use of at least one delivery vehicle or technique selected from the set of viral vectors, microinjection, electroporation, coprecipitaton, liposomes, aerosol delivery and lavage. The portion of the sequence may be 5 bases in length, between 5 and 50 bases in length, 5 and 30 bases in length between 10 and 20 bases in length, or another suitable length may be found. The organism may be a human patient and the method can include treating the patient against a cancerous disease.

The invention also includes a method of inhibiting retinoic acid hydroxylation in an organism in need of such inhibition by administering to the organism an effective amount of an antibody, such antibodies being described above. A particularly useful antibody for the treatment of a human would be an antibody to the protein having the amino acid sequence identified as SEQ ID NO:4, or a portion thereof. It would be advantageous to adapt such an antibody for administration to a human by "humanizing" the antibody, as is understood by those skilled in the art [Hozumi, 1993].

The invention includes a method for producing a desired protein, comprising providing a cell which can produce an endogenous protein in response to exposure to a retinoid; incorporating into DNA of the cell a DNA sequence encoding the desired protein at or near a site which is normally occupied by a DNA sequence encoding the endogenous protein; and exposing the cell to the retinoid so as to induce production of the desired protein.

In another embodiment, the present invention is a kit for determining the presence of a protein having the ability to oxidize a retinoid, and having an amino acid sequence which is at least about 30% conserved in relation to the amino acid sequence identified as SEQ ID NO:2 or identified as SEQ ID NO:32, or more likely for determining the presence of a protein (or peptide fragment thereof) having an amino acid sequence identified as SEQ ID NO:4, the human protein. The kit includes an antibody to the protein linked to a reporter system wherein the reporter system produces a detectable response when a predetermined amount of the protein and the antibody are bound together.

In another aspect, the present invention is a kit for determining the presence of a nucleic acid encoding a protein of invention, or having the sequence identified as SEQ ID NO:3 or SEQ ID NO:5 or SEQ ID NO:31, or which varies from the sequence due to the degeneracy of the genetic code, or a nucleic acid strand capable of hybridizing with at least one said nucleic acid under stringent hybridization conditions. The kit includes a nucleic add molecule capable of hybridizing with at least a portion of a said nucleic acid or nucleic acid strand under stringent conditions in which the nucleic acid molecule is linked to a reporter system wherein the reporter system produces a detectable response when a predetermined amount of the nucleic acid or nucleic acid strand and nucleic acid molecule are hybridized with each other. The molecule can be 5 bases in length or longer; between 5 and 50 bases in length, between 5 and 30 or 40 bases in length, or between 10 and 20 bases in length. Of course it might be possible to find a more suitable base length.

The present invention includes an isolated DNA molecule having a nucleotide sequence selected from the group consisting of:
(a) SEQ ID NO:33;
(b) SEQ ID NO:34;
(c) SEQ ID NO:35; and
(d) a fragment of (a), (b) or (c),
wherein the DNA molecule possesses promoter activity.

in a more particular aspect, the invention includes a DNA molecule of one of the indicated sequences in which the DNA molecule includes the sequence TGAACTNNNNNTGAACT, where "N" can be any nucleotide and there can be 0 to 5 N (SEQ ID NO:39), wherein x has a value of up to 5. This sequence is conserved in all three of the nucleotide sequences identified as having promoter activity, particularly where x is 5. Even more particularly, the invention includes such a DNA molecule in which the sequence TCTGASSAAGKTAAC (SEQ ID NO:40) occurs downstream from the sequence TGAACTNNNNNTGAACT, where "N" can be any nucleotide and there can be 0 to 5 N (SEQ ID NO:39). Even more particularly, the sequence includes the sequence AATT between the sequence TGAACTNNNNNTGAACT, where "N" can be any nucleotide and there can be 0 to 5 N (SEQ ID NO:39) and the sequence TCTGASSAAGKTAAC (SEQ ID NO:40), the AATT having been found immediately downstream of the sequence TGAACTNNNNNTGAACT, where "N" can be any nucleotide and there can be 0 to 5 N (SEQ ID NO:39). It has been observed that there can be up to six nucleotides between the sequence TGAACTNNNNNTGAACT, where "N" can be any nucleotide and there can be 0 to 5 N (SEQ ID NO:39) and the sequence TCTGASSAAGKTAAC (SEQ ID NO:40). There can also be the sequence CAATTAAAGA (SEQ ID NO:41) upstream of the sequence TGAACTNNNNNTGAACT, where "N" can be any nucleotide and there can be 0 to 5 N (SEQ ID NO:39). In a particular aspect, the nucleotide sequence having promoter activity includes the sequence CAATTAAGATGAACTTTGGGTGAACTAATT (SEQ ID NO:42) and the sequence TATAA. Particularly, the sequence TATAA is downstream of the sequence TGAACTNNNNNTGAACT, where "N" can be any nucleotide and there can be 0 to 5 N (SEQ ID NO:39), and more particularly, the sequence TATAA is downstream of the sequence TCTGASSAAGKTAAC (SEQ ID NO:40) and it can be spaced up to about 55 nucleotides downstream from the sequence TGAACTNNNNNTGAACT, where "N" can be any nucleotide and there can be 0 to 5 N (SEQ ID NO:39).

The invention includes a recombinant DNA having such a DNA sequence having promoter activity. The recombinant DNA can also include one or more structural genes. The structural gene(s) can encode cytochrome P450 protein(s). The invention includes an expression plasmid including such recombinant DNA and an isolated cell containing the recombinant DNA. The cell is usually eukaryotic.

The invention includes a process for the production of recombinant protein(s), including steps of culturing a cell according to the invention containing recombinant DNA and recovering the protein(s) produced. The protein(s) can be a cytochrome P450, but is not necessarily so. The protein(s) can be a fusion protein.

The invention further includes a method of screening drugs for their effect on activity of a retinoic acid inducible protein, comprising exposing a purified said protein to a said drug and determining the effect on the activity. The activity can be hydroxylation of a retinoic acid, particularly all-trans retinoic acid. In particular, the activity can be hydroxylation of a retinoic acid, particularly all trans-retinoic acid, at the 4 position of the β-ionone ring thereof.

The invention provides a method of screening drugs for their effect on activity of any protein having P450RAI activity of the present invention, particularly ascertaining the effect a potential drug has on the oxidation of retinoic acid, specifically all-trans retinoic acid.

In yet another aspect, the invention includes a method of screening drugs for their effect on expression of a gene wherein the gene is inducible by a retinoid, including the step of exposing a recombinant DNA described above to a potential drug and determining the effect on gene expression. This can include exposing the recombinant DNA in the presence of a said retinoid. The gene can be a reporter gene which does not metabolize retinoic acid. The method can include ascertaining the effect on transcription of the gene.

The invention includes a method of screening a drug for its effect on the metabolism of a retinoid by a cytochrome P450 encoded by a nucleotide sequence of the invention which is incorporated into an expression system so as to be under control of a nucleotide sequence having native promoter activity for a said cytochrome P450, comprising:
exposing the system to the drug in the presence of the retinoid so as to determine the effect of the drug on metabolism of the retinoid.

The retinoid can be retinoic acid and it can be all trans-retinoic acid.

The invention includes any drug identified according to such a method as having the effect of modulating, and preferably reducing, the activity of a said protein or as having the effect of modulating, and preferably reducing, gene expression.

The invention includes a method for inhibiting retinoic acid metabolism in an organism in need of such inhibition, comprising administering to the organism an effective amount of a drug identified according to a method of the invention.

BRIEF DESCRIPTION OF THE DRAWINGS

The file of this patent contains at least one drawing excuted in color. Copies of this patent with color drawings are provided to the Patent and Trademark Office with payment of the necessary fee.

FIG. 1 is a schematic representation of the steps used to isolate retinoid-regulated genes using differential display of mRNA.

FIG. 2(a) shows a polyacrylamide gel of PCR amplified mRNA in duplicate obtained using retinoic acid-treated fish (lanes 1 and 2) and dimethyl sulfoxide (DMSO-) treated control fish (lanes 3 and 4). The arrow indicates a PCR amplified band present in the RA-treated samples and not observed in the controls.

FIG. 2(b) shows the nucleotide sequence (SEQ ID NO:1) of the 337 base pair PCR product isolated from the band (arrow) of FIG. 2(a). The arrows indicate the nucleotide sequences where the upstream and downstream priming sites for differential display PCR amplification were located in the 3'-untranslated portion of zP450RAI.

FIG. 2(c) shows an amino acid sequence (SEQ ID NO:2) corresponding to cDNA (492 amino acid open reading frame). The boxed residues indicate the heme-binding motif characteristic of cytochrome P450s.

FIG. 2(d) shows amino acid sequence comparisons between zP450RAI and several other cytochrome P450s (SEQ ID Nos: 8,7,8,9,10) in the area of the conserved heme-binding motif found in the superfamily. The cysteine, designated 0 in the figure, which has been shown to be directly involved in heme-binding [Gotoh, 1989] is surrounded by several highly conserved amino acids.

FIGS. 4(a) and 4(b) are plots of cpm vs fraction number for cells incubated with 575 pM [11,12-$^3$H]RA for 4 hours and 24 hours, respectively, pSG5-zP450RAI COS-1 cells (—) and control cells ( - - - ). Metabolism of [11,12-$^3$H]RA to total aqueous soluble metabolites was measured using aliquots of the aqueous soluble extract subjected to β-scintillation counting. See insets of FIGS. 4(a) and (b). FIGS. 4(c) and 4(d) are plots of absorbance vs retention time for cells incubated with 1 μM RA for 4 and 24 hours, respectively. Peaks observed in zP450RAI transfected cell are shaded black. The region of the chromatogram from 4 to 6 min has been expanded (see insets of FIGS. 4(c) and (d)). In cells transfected with zP450RAI cDNA, the generation of peaks corresponding to 4-oxo RA and 4-OH RA was observed.

FIG. 9 shows the murine cRNA amino acid sequence (top row, SEQ ID NO:32) aligned with the human P450RAI amino acid sequence (middle row; SEQ ID NO:4) and the zebrafish cDNA amino acid sequence (bottom row. SEQ ID NO:2).

FIG. 10(a) shows elution profiles of lipid soluble extracts obtained from treated media of pSG5-hP450RAI transfected COS-1 cells and pSG5 transfected control cells. Plots of cpm vs fraction number for cells incubated with [11,12-$^3$H]RA for 24 hours of pSG5-hP450RAI COS1 cells (—) and control cells (—) are shown. FIG. 10(b) shows measurement of aliquots of the aqueous soluble extract subjected to β-scintillation counting taken to determine metabolism of [11,12-$^3$H]RA to total aqueous soluble metabolites. FIG. 10(c) shows plots of absorbance vs retention time for hP450RAI transfected cell (—) and control cells (—) cells incubated with 1 pM RA for 24 hours. The inset is the region around 10 minutes, expanded for clarity.

FIG. 12(a) shows elution profiles of lipid soluble extracts obtained from media of MCF10A cells exposed to RA and unexposed MCF10A control cells. Plots of cpm vs fraction number for cells incubated with [11,12-$^3$H]RA for 24 hours of RA-induced MCF10A cells (—) and control (—) are shown.

FIG. 12(b) shows elution profiles of lipid soluble extracts obtained from treated media of MCF7 cells exposed to RA and unexposed MCF7 control cells. Plots of cpm vs fraction number for cells incubated with [11,12-$^3$H]RA for 24 hours of RA-induced MCF7 cells (—) and control (—) are shown.

FIG. 12(c) shows the total aqueous soluble metabolites measured using aliquots of the aqueous soluble extracts of the cell lines described in FIGS. 12(a) and (b) subjected to β-scintillation counting. The first two bars are for unexposed MCF7 cells and MCF7 cells exposed to RA, respectively. The third and fourth bars are for unexposed MCF10A cells and MCF10A cells exposed to RA, respectively.

FIG. 13(a) shows elution profiles of lipid soluble extracts obtained from microsomal preparations after incubation with radiolabelled RA for ninety minutes, as described in Example 7. Plots of dpm vs fraction number for HeLa P microsomes (■,▲) and HeLa RAI microsomes (▼,♦).

FIG. 13(b) shows fractions 5 to 15 of FIG. 13(a) on a larger scale.

FIG. 15 shows promoter sequences of human, mouse and zebrafish P450RAI (SEQ ID NOs:33, 34, and 35, respectively). The boxed regions show highly conserved regions while the arrows indicate spaced apart consensus sequences of RAREs.

DESCRIPTION OF PREFERRED EMBODIMENTS

Figure 3A:
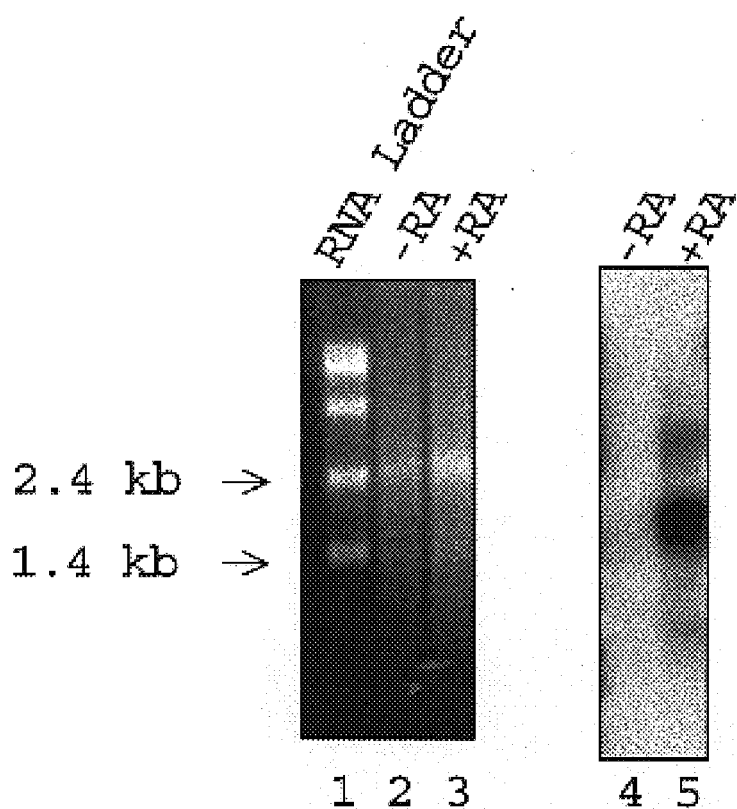
FIG. 3(a) shows Northern blot analysis of mRNAs obtained from regenerate tissue of RA-treated fish in lane 5, and controls (DMSO-treated fish) in lane 4, using a zP450RAI cDNA probe. Comparison to an RNA ladder (lane 1) shows the major zP450RAI transcript to be in the 1.4–2.4 kb range.

FIG. 1 outlines the steps used to isolate retinoid-regulated genes using differential display of mRNA. The cloned products isolated in step 6 of FIG. 1 were used for sequencing and screening of *Danio rerio* (*D. rerio*) cDNA libraries. P1, P2 and P3 correspond to fragments from RA induced mRNAs. P4 is a PCR product from a down-regulated mRNA. Details of procedures followed in determination of gene sequences described herein follow.

*Danio rerio* Stocks

*D. rerio* were kept at 28.5° C. in 40 L tanks with 25–30 fish per tank on a 14 hour light-10 hour dark cycle. Tap water was conditioned by the addition of 10 ml of Water Conditioner (Sera Aqutan) and 10 ml of 250 g/L Aquarium Salt (Nutra Fin) per 20 L 2–3 L of water was changed daily. Amputation of fins was carried out following anaesthetization of the fish in a solution of 0.2% ethyl-m-aminobenzoate methanesulfonic acid (ICN) in conditioned water. Retinoic acid treatment was performed by adding all-trans RA, to a final concentration of $10^{-6}$ M, directly into the tank water two days following amputation. Both control- and RA-treated fish were kept in the dark during the experiments.

Differential Display of mRNAs

Differential mRNA display was performed essentially as described by Liang and Pardee (1992) with appropriate modifications as described herein. Regenerating tissues were collected 3 days post-amputation (24 hours post-RA addition) and quick frozen in liquid nitrogen. Poly (A)+ RNA was isolated using the Micro Fast-Track kit. Duplicate independent reverse transcription reactions were performed on the isolated poly(A)+RNA from both the treated and untreated samples for each specific 3' poly-T primer used (5'-$T_{12}$VN-3'). The symbol "V" represents A or C or G and not T or U. Several combinations of the 3' poly-T primers given in the first column of Table 1 and the upstream primers given in the second column were utilized for PCR amplification. For each reaction 0.1 μg poly(A)+RNA was reverse transcribed in a 20 μl reaction volume containing 300U Superscript Reverse Transcriptase (Gibco/BRL), 1× Buffer, 20 μM each dGTP, dATP, dCTP and dTTP, 10 μM dithiothreitol (DTT) and 5 pmol of 5'-$T_{12}$VN-3' primer. The reactions were mixed and incubated at 35° C. for 60 minutes, followed by 5 minutes at 95° C. PCR amplification was performed in a Perkin Elmer Cetus PCR machine as follows: 1 μl cDNA synthesis reaction, 5U Taq DNA polymerase (Gibco/BRL), 1×PCR Buffer, 2 μM each dGTP, dATP, dCTP and dTTP, 10 μCi α-[$^{35}$S]dATP (redivue, Amersham) 1.2 mM $MgCl_2$, 0.5 μM upstream primer and 0.5 μM of the corresponding 5'-$T_{12}$VN-3' primer. PCR conditions were as follows: 1 cycle, 94° C. for 5 minutes; 40 cycles, 94° C. for 30 seconds, 42° C. for 1 minute, 72° C. for 30 seconds; followed by a final extension of 5 minutes at 72° C. 4 μl of the PCR reactions were loaded onto a 6% non-denaturing polyacrylamide gel and electrophoresed at 60 watts, 45° C. The gel was dried and exposed for 12 to 24 hours on Kodak XAR film at room temperature.

TABLE 1

Sequences of the downstream Poly (T) oligonucleotides for the differential display procedure.

| 3'-Poly(T) primers: | 5'-degenerate primers: |
|---|---|
| 5'-TTT TTT TTT TTT GG-3' | 5'-AAG CGA CCG A-3' |
| 5'-TTT TTT TTT TTT GA-3' | 5'-TGT TCG CCA G-3' |
| 5'-TTT TTT TTT TTT GT-3' | 5'-TGC CAG TGG A-3' |
| 5'-TTT TTT TTT TTT GC-3' | 5'-GGC TGC AAA C-3' |
| 5'-TTT TTT TTT TTT AG-3' | 5'-CCT AGC GTT G-3' |
| 5'-TTT TTT TTT TTT AA-3' | |
| 5'-TTT TTT TTT TTT AT-3' | |
| 5'-TTT TTT TTT TTT AC-3' | |
| 5'-TTT TTT TTT TTT CG-3' | |
| 5'-TTT TTT TTT TTT CA-3' | |
| 5'-TTT TTT TTT TTT CT-3' | |
| 5'-TTT TTT TTT TTT CC-3' | |

In Table 1, the sequences in the first column are identified as SEQ ID NOs: 12, 13, 14, 15, 16, 17, 18, 19, 20, 21, 22 and 23, respectively. The sequences in the second column are identified as SEQ ID NOs: 24, 25, 26, 27 and 28, respectively.

Gel Purification and Reamplification

Bands demonstrating reproducible differential amplifications (see FIG. 2a) were found for the upstream-downstream primer combination of 5'-TGCCAGTGGA-3'-poly-T primer, 5'-TTT TTT TTT TTT AG-3' (SEQ ID NOs: 26 and 16, respectively). These bands were excised from th gel by overlaying the X-ray film and cutting out the corresponding piece of dried gel and filter paper. The PCR product corresponding to a fragment of the protein described herein was isolated from the band in FIG. 2(a). Samples were placed in 100 μl of nuclease free water, incubated for 10 minutes at room temperature, then boiled for 15 minutes. The supernatant was recovered following a 15 minute centrifugation at 12,000×g.

in order to facilitate cloning of the PCR products, several changes were made to the reactions. Primers which included EagI restriction endonuclease sites were used in the reamplification. Based on results obtained in the differential display analysis, the upstream 5'-TGCCAGTGGA-3' (SEQ ID NO:26) primer was replaced by 5'-GTAGCGGCCGCTGCCAGTGGA-3' (SEQ ID NO: 29) and the downstream poly-T primer. 5'-TTT TTT TTT TTT AG-3' (SEQ ID NO:6), was replaced by 5'-GTAGCGGCCGCT$_{12}$-3' (SEQ ID NO:30). In addition, the reaction volume was increased to 40 μl, isotope was omitted and 20 as opposed to 40 cycles were performed. 6 μl aliquots of the PCR reactions were removed and the products were visualized by electrophoresis in a 1% agarose gel followed by ethidium bromide staining and UV illumination.

Cloning PCR Products

The reamplified products were purified by phenol/chloroform extraction followed by ethanol precipitation. The resulting DNA pellet was resuspended in 17 μl of sterile water and digested at 37° C. for 1 hour by the inclusion of 10U EagI (New England Biolabs), and 1×NEB 3 buffer. EagI restriction endonuclease was heat inactivated by incubation at 65° C. for 20 minutes. pBluescript SK+ vector was prepared by digestion with EagI, followed by dephosphorylation using calf intestinal alkaline phosphatase (CAP, Promega). Restriction digests were purified using the GeneClean II Kit (Bio 101) following electrophoresis in a 1% agarose gel. In a total ligation volume of 10 μl, 2 μl of digested PCR product, 1 μl digested SK+, 1U T4 DNA ligase (Gibco/BRL) and 1× buffer were incubated at 16° C. overnight. *E coli* bacterial strain JM109 was transformed with 1 μl of the ligation product using a BioRad Gene Pulser, then plated on LB+ampicillin plates and incubated overnight at 37° C.

Colony Selection

Individual colonies were transferred in duplicate to fresh LB plates and grown overnight at 37° C. Colonies were tranferred to nitrocellulose membrane and denatured in a solution of 1.5M NaCl, 0.5M NaOH for 5 minutes, neutralized in 1.5M NaCl, 0.5M Tris-HCl, pH 8.0 for 5 minutes, followed by two 5 minute washes in 2×SSC. Membranes were then UV cross-linked (Stratalinker UV Crosslinker, Stratagene). Prehybridization and hybridization were performed using Quickhyb (Stratagene) following the manufacturer's directions. Each colony lift was probed with the corresponding PCR product isolated during the gel reampilfication and purification step. α-[$^{32}$P]-dATP labelled probes were generated using the Prime-It Kit II (Stratagene). Subsequent to hybridization, filters were washed twice for 20 minutes in 2×SSC, 0.1% SDS solution at room temperature and exposed to Kodak X-omat autoradiography film overnight at −70° C. Positive colonies were selected from the duplicate plates, grown overnight in LB+ampicillin (100 μg/ml) and plasmid DNA isolated using the Qiaprep Spin Plasmid Kit (Qiagen).

Clones were sequenced using the T7 Sequencing Kit (Pharmacia Biotech). Sequence comparisons were generated using the GeneWorks software package (Intelligenetics).

Screening of a *D. rerio* cDNA Library

A random primed *D. rerio* 6–18 hour embryo cDNA library constructed in Uni-ZAP II (Stratagene) was produced. 4.5×10$^5$ independent pfu were screened using the random primed, α-[$^{32}$P]-dATP labelled 337 bp PCR fragment isolated by mRNA differential display as a probe. Filters were prehybridized for 1–4 hours at 42° C. in 50% formamide, 5×SSPE, 1× Denhardt's solution, 0.2 mg/ml denatured salmon sperm DNA. Hybridization was performed at 42° C. by adding denatured probe to the prehybridization solution. Filters were washed two times for 20 minutes in 2×SSC, 0.05% SDS at room temperature and exposed to Kodak XAR film overnight at −70° C. Positive plaques were picked into 500 μl SM buffer and subjected to additional rounds of rescreening until purified. Positive plaques were exposed to the in vivo excision protocol following the manufacturer's directions (Stratagene). pBluescript containing colonies were plated onto LB+amp plates and grown overnight at 37° C. Sequence data were generated using the T7 Sequencing Kit (Pharmacia) and analysed using the GeneWorks software package (Intelligenetics).

Whole Mount in situ Hybridization

RA- and DMSO-treated regenerates were isolated 72 hours post-amputation (24 hours post RA/DMSO addition), washed in PBS and prepared for whole mount in situ hybridization. In situ hybridizations were undertaken as previously described [White, 1994].

Northern Blot Analysis

Fish were allowed to regenerate their caudal fins for 72 hours. At 48 hours $10^{-6}$M all-trans RA in DMSO vehicle or DMSO alone was added directly to the tank water. mRNA was prepared using the Micro Fast-Track mRNA isolation kit (Onvitrogen, Calif.) according to the manufacturer's directions. 3.0–5.0 μg poly A+ RNA was electrophoresed, blotted and probed using a previously described method [White, 1994] with the full length zP450RAI cDNA obtained as described below. Ethidium bromide stained agarose gel showed that equivalent amounts of mRNA were used in the blotting experiments. See lanes 2 and 3 of FIG. 3(a).

HPLC Analysis

Figure 4:
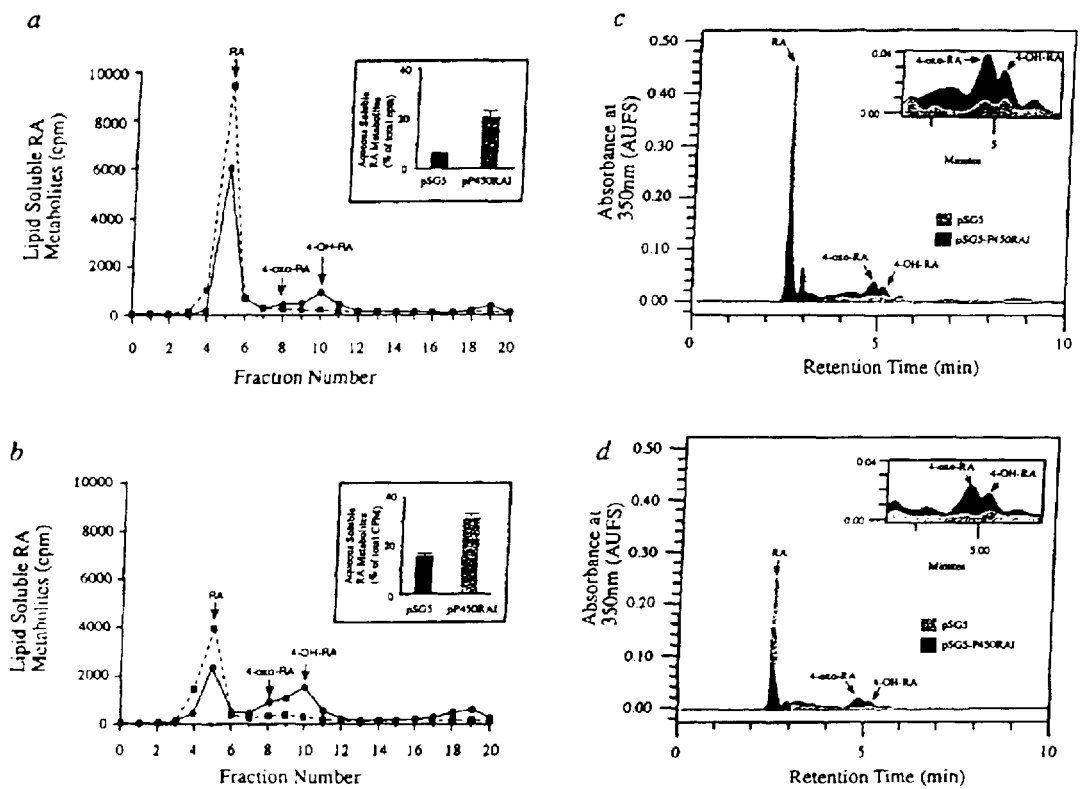
FIG. 4 shows elution profiles of lipid soluble extracts obtained from treated media of pSG5-zP450RAI transfected COS-1 cells and pSG5 transfected control cells.

Media from transfected cells incubated with 575 pM [11,12-$^3$H]RA (FIGS. 4(a) and 4(b)) or 1 μM RA (FIGS. 4(c) and 4(d)) for either 4 hrs (FIGS. 4(a) and 4(c)) or 24 hrs (FIGS. 4(b) and 4(d)) were acidified with 0.1% acetic acid. Lipid soluble metabolites were separated from aqueous soluble metabolites using a total lipid extraction of the medium [Bligh, 1957]. Metabolism of [11,12-$^3$H]RA to total aqueous soluble metabolites was measured using aliquots of the aqueous soluble extract subjected to β-scintillation counting (See the insets of FIGS. 4(a) and 4(b)). Lipid soluble extracts were evaporated to dryness under a stream of nitrogen and resuspended in 93.5/5/1/0.5 hexene/isopropanol/methanol/acetic acid (H/I/M/AA). Metabolites were separated by HPLC using a Zorbax-SIL (3μ, 8×0.62 cm) column eluted with a solvent system of 93.5/5/1/0.5 H/I/M/AA at a flow rate of 1 ml/min.

EXAMPLE 1

Characterization of a Novel Cytochrome P450

Transcripts present in fin tissue regenerating in the presence or absence of RA were compared using the differential display PCR technique developed by Liang and Pardee [Liang, 1992] (FIG. 2(a)). One of the differential display products which exhibited a dependence on the presence of RA for its expression, indicated by the arrow in FIG. 2(a), was isolated and sequenced. The sequence is identified as SEQ ID NO:1 and is also shown in FIG. 2(b). The amino acid sequence corresponding to the cDNA, termed here, "zP450RAI", is shown in FIG. 2(c) and identified as SEQ ID NO:2. BLAST search analyses revealed sequence homology between zP450RAI and multiple members of the cytochrome P450 superfamily. Alignments between zP450RAI cDNA deduced amino acid sequence and those of other cytochrome P450s indicated that zP450RAI exhibited less than 30% overall amino acid identity with members of previously defined subfamilies [Nelson, 1993]. zP450RAI contains many of the structural motifs which are common to cytochrome P450 family members, including the heme-binding domain located in the C-terminal portion of the protein. See FIG. 2(d). The P450RAI family has been designated "CYP26".

EXAMPLE 2

Cell Specific Induction of zP450RAI by All-trans RA

Northern blot analysis of mRNAs expressed in regenerate tissue isolated from control (dimethyl sulfoxide-treated) and RA-treated fish was performed with a full-length zP450RAI cDNA probe. zP450RAI transcripts were not detectable in regenerate tissue from control fish (FIG. 3(a), lane 4) but were very noticeably present in tissues isolated from fish exposed to RA for 24 hours (FIG. 3(a), lane 5).

Figure 3B:
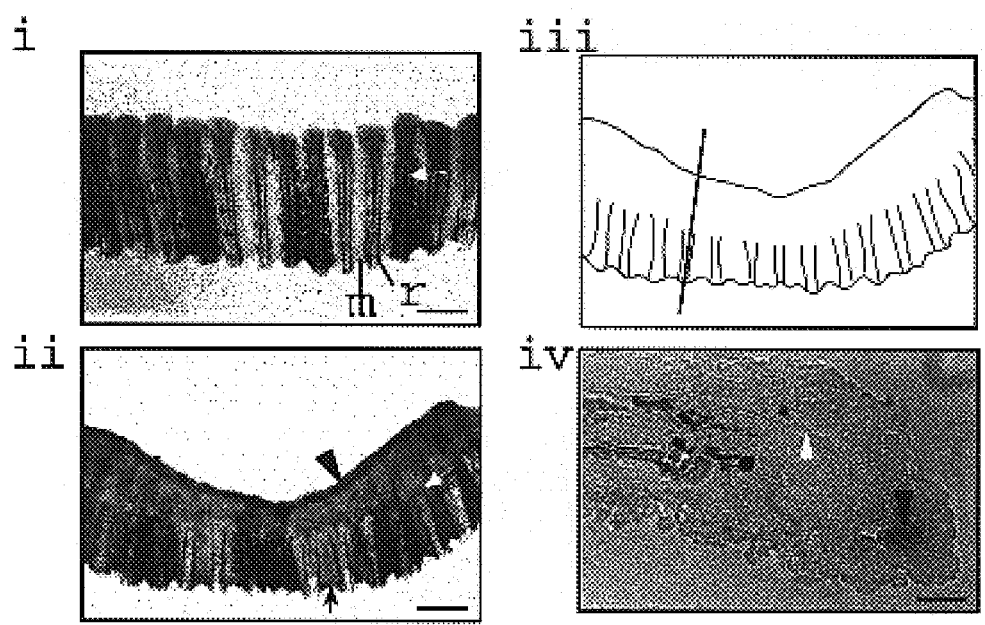
FIG. 3(b) shows localization of zP450RAI transcripts in regenerating caudal fin tissue 72 hours post-amputation by whole mount in situ hybrizaton. (i) zP450RAI transcripts were found to be undetectable in DMSO-treated regenerates. The original plane of amputation is indicated by the white line with arrowhead; m (soft mesenchyme) and r (bony rays) are labelled. (ii) in a sample obtained from an RA-treated fish, zP450RAI transcripts, indicated by the black arrowhead, were found to be localized to a band of cells extending across the distal tip of the regenerate. Lower levels of expression of zP450RAI were also evident in non-regenerate tissue at the proximal base of the isolated fin, as indicated by the black line with arrowhead. The plane of amputation is indicated by the white line with arrowhead as in FIG. 3(b)(i). (iii) A histological section taken through the plane is indicated by the line. (iv) A histological section of RA-treated fins post-hybridization is shown. Localized expression of zP450RAI was detected in a subset of epithelial cells (black arrowhead) which lie at the distal tip of the regenerate. Basement membrane separating the dense blastemae and the wound epithelium is indicated by the grey arrowhead.

Whole mount in situ hybridization was used to determine the cellular localization of zP450RAI expression in regenerating fin tissue. FIG. 3(b) shows regenerating fins from control and RA-treated fish. zP450RAI transcripts are not detectable in control fin tissue (FIG. 3(b)(i)). In regenerating tissue from RA-treated fish, zP450RAI transcripts were found to be abundant in a layer of epithelial cells extending across the distal edge of the wound epithelium as indicated by the black arrowhead in FIG. 3(b)(ii). Some low level staining was also observed in inter-ray tissue as indicated by the black line with arrowhead in FIG. 3(b)(ii). A histological section of an RA-treated fin, taken along the line shown in FIG. 3(b)(iii), is shown in FIG. 3(b)(iv). The section indicates that cells expressing zP450RAI are located deep within the epithelial layer at the distal tip of the blastemal mesenchyme. Whole mount in situ hybridization thus illustrates the usefulness of nucleic acid probes of the invention for the localization of cytochrome P450RAI mRNA in whole tissue.

EXAMPLE 3

Metabolism f All-trans RA by zP450RAI Transfected Cells

Retinoic acid as a substrate of zP450RAI was studied. The full-length zebrafish zP450RAI cDNA was cloned into the eukaryotic expression vector pSG5 [Green, 1988]. COS-1 cells were transiently transfected with either pSG5 or pSG5-zP450RAI and then incubated with either picomolar concentrations of [11,12-$^3$H]all-trans-RA or micromolar concentrations of non-radioactive all-trans-RA. COS-1 cells are an African green monkey kidney "fibroblast-like" cell line. zP450RAI expression in COS-1 cells promoted the rapid conversion of RA into both lipid and aqueous-soluble metabolites. See FIGS. 4(a) and 4(b). Fractions of total lipid extracts of transfected cells were initially separated by normal-phase HPLC on Zorbax-SIL. Comparison between extracts from pSG5 and pSG5-zP450RAI-transfected cells indicated that zP450RAI significantly increased RA metabolism. Incubation of zP450RAI-transfected cells with 575 pM [11,12-$^3$H]all-trans-RA for either 4 or 24 hours resulted in accumulation of RA metabolites, one of which co-migrated on a column with synthetic standards 4-OH-RA and 18-OH-RA, and a second slightly less polar metabolite which co-migrated with 4-oxo-RA standard (FIGS. 4(a) and 4(b)). Rechromatography of RA metabolites using other HPLC systems confirmed the identity of these two metabolites as 4-OH-RA and 4-oxo-RA (Table 2). It is possible that the aqueous-soluble radioactivity represents glucuronides of RA metabolites or glucuronides of RA itself. Rapid glucuronidation of 4- and 18-hydroxy-RA in mammalian cell extracts has been reported by others [Wouters, 1992; Takatsuka, 1996].

TABLE 2

Chromatographic properties of RA metabolites.

| Metabolite | Retention Time (min) | | |
|---|---|---|---|
| | Z-Sil[a] | Z-CN[b] | Z-ODS[c] |
| RA (std) | 2.57 | 4.47 | 19.92 |
| 4-oxo-RA (std) | 4.79 | 11.33 | 11.73 |
| 4-OH-RA (std) | 5.17 | 9.65 | 12.65 |
| 18-OH-RA (std) | 5.06 | 9.53 | 14.03 |
| Peak 1 (RA) | 2.57 | 4.48 | 19.73 |
| Peak 2 (4-oxo-RA) | 4.87 | 11.38 | 11.57 |
| Peak 3 (4-OH-RA) | 5.16 | 9.68 | 12.68 |

[a]HPLC conditions: Zorbax-SIL column eluted with 93.5/5/1/0.5 H/I/M/A.A. (1 ml/min)
[b]HPLC conditions: Zorbax-CN column eluted with 93.5/5/1/0.5 H/I/M/A.A (1 ml/min)
[c]HPLC conditions: Zorbax-ODS column eluted with a 20 min linear gradient with solvent containing 10 mM ammonium acetate which ranged from 55.45 to 5.95 $H_2O$/MeOH (2 ml/min).

A similar pattern of zP450RAI-dependent metabolism was also observed using a much higher RA concentration (1 μM). zP450RAI-transfected COS-1 cells incubated for 4 or 24 hours with 1 μM RA generated two closely-running peaks which were discernible in a 350nm HPLC trace shown in FIGS. 4(c) and 4(d), but which were essentially undetectable in control pSG5-transfected cells (See the insets of FIGS. 4(c) and 4(d)). These peaks co-migrated with those of 4-oxo-RA and 4-OH-RA standards, respectively. Diode array spectrophotometric detection of the zP450RAI-generated peaks showed that the spectral properties of the two metabolite peaks matched the standard retinoids [In hexane-based solvents: 4-OH-RA, $\lambda_{max}$=350 nm; 4-oxo-RA, $\lambda_{max}$=355 nm; in methanol-based solvents: 4-OH-RA, $\lambda_{max}$=340 nm; 4-oxo-RA, $\lambda_{max}$=360 nm].

The invention thus includes a retinoic acid metabolizing protein belonging to the family of cytochrome P450s, designated CYP26, and generation of the protein in zebrafish caudal fin wound epithelium being induced in response to RA treatment While RA metabolizing activity has previously been detected in epithelial tissues of several species [Frolik, 1979; Roberts, 1979; Wouters, 1992; Duell, 1992], an actual enzyme responsible for such activity has heretofore been unknown.

zP450RA) is up-regulated by RA treatment and apparently this up-regulation occurs in a specific set of cells in the wound epithelium of regenerating zebrafish caudal fins.

It might be of relevance to the regulation of the generation of this enzyme in vivo that experiments with F9 cells where RARs have been selectively ablated indicate that RAR-α and RAR-γ might have a role in the regulation of RA metabolism [Boylan, 1995]. The expression of both RAR-α and RAR-γ in the regenerating caudal fin is consistent with the suggestion that they may be involved in the regulation of P450RAI expression by RA [White, 1994].

EXAMPLE 4

Cloning of Human P450RAI

The amino acid sequence corresponding to the DNA of zebrafish P450RAI (zP450RAI) (SEQ ID NO:2) was used to search an express sequence tag (EST) database. A commercially available EST clone (SEQ ID NO:11) having a high degree of homology with a C-terminal portion of the zP450RAI (from Glu 292 to Phe 410 of SEQ ID NO:2) was purchased (Research Genetics, Huntsville, Ala.). The clone is reportedly from a human infant brain cDNA library (Bento Soares and M. Fatima Bonaldo) and is apparently otherwise unpublished. The purchased clone was sequenced using the T7 sequencing kit (Pharmacia) and sequence data was generated using the Geneworks Software Package Intelligenetics).

A cDNA library generated from an NT2 cell line treated with retinoic acid is commercially available (Stratagene, cat#939231) and this product was used for further studies. The cDNA library was probed with a nucleic acid having a sequence identified as SEQ ID NO:11. Eleven positively hybridizing clones were isolated and purified according to the manufacturers directions. Sequence data for these clones were generated using the T7 Sequencing Kit (Pharmacia) and analyzed using the Geneworks package (Intelligenetics). The human DNA sequence is identified as SEQ ID NO:5 and the corresponding polypeptide as SEQ ID NO:4.

EXAMPLE 5

Isolating Mouse P450RAI

It has been found by the present inventors (results not shown) that RA can induce mRNA transcripts which cross hybridize with a hP450RAI cDNA probe in either of the F9 and P19 mouse cell lines having 4-hydroxylase activity, as described by Blumberg et al. [Blumberg et al. 1995; Achkar et al., 1996].

A retinoic acid-treated P19 teratocarcinoma cDNA library in lambda Unizap XR (Stratagene) was screened using $^{32}$P-labelled full length human P450RAI as a probe. Nitrocellulose filters were hybridized overnight at 37° C. in a buffer containing 50% formamide, 1× Denhardt's, 5×SSPE, 0.1% SDS, and 100 μg/ml boiled salmon sperm DNA, and washed in 2×SSC, 0.1% SDS for 2×15 minutes at room temperature followed by 20 minutes at 37° C. From a total of 600,000 plaque forming units of phage, 72 positives were isolated. Of these, 18 were purified, as described above, and one was found to have a full-length cDNA insert 1.7 kb in length homologous to the full-length human clone previously isolated. The murine DNA sequence is identified as SEQ ID NO:31 and the corresponding polypeptide as SEQ ID NO:32. FIG. 9 shows aligned portions of the amino acid sequence of the mouse protein (SEQ ID NO:32) with those of the human protein (SEQ ID NO:4) and the zebrafish protein (SEQ ID NO:2).

EXAMPLE 6

Transient Tranfection Analysis

Figure 11C:
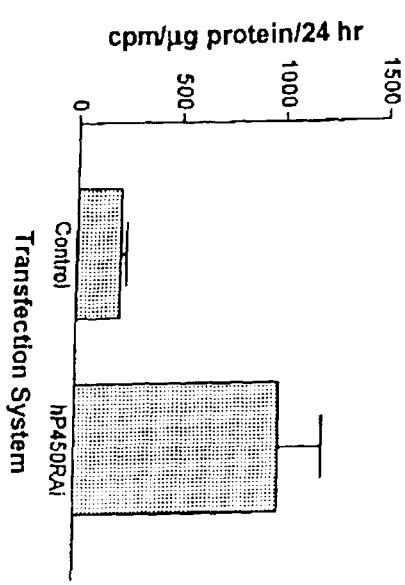
FIG. 11(c) shows formation of aqueous soluble metabolites of pSG5-hP450RAI transfected COS-1 cells and pSG5 transfected control cells.
Figure 11A:
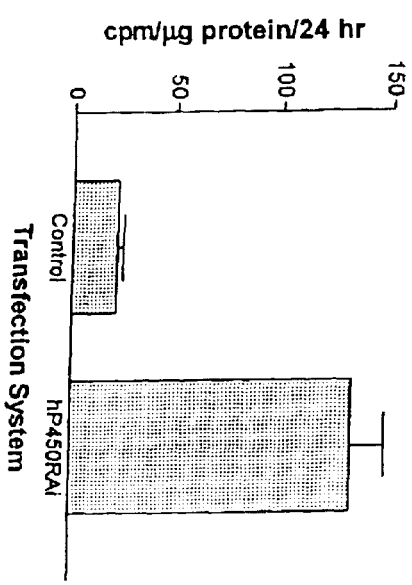
FIG. 11(a) shows 4-oxo-RA production of pSG5-hP450RAI transfected COS-1 cells and pSG5 transfected control cells.
Figure 11D:
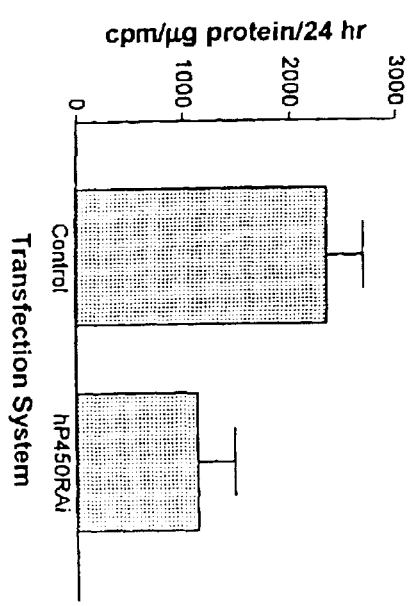
FIG. 11(d) shows unmetabolized RA of pSG5-hP450RAI transfected COS-1 cells and pSG5 transfected control cells.
Figure 11B:
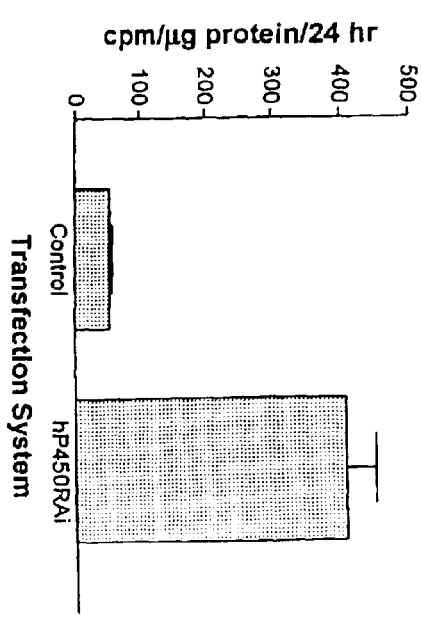
FIG. 11(b) shows 4-OH-RA production of pSG5-hP450RAI transfected COS-1 cells and pSG5 transfected control cells.

COS-1 cells were subcultured 20 hours prior to transfection which was carried out according to the standard DEAE-dextran method [Sambrook, 1989; Maniatis, 1982]. Cells were transfected with pE-AR (adrenodoxin expression vector, 1 μg/P100 plate) and pE-ADX (adrenodoxin reductase expression vector, 1 μg/P100 plate) together with 3 μg per plate of either pSG5 (control) or hP450RAI-pSG5 (experimental). [11,12-$^3$H]all-trans retinoic acid (60,000 cpm per plate) was added 24 hours after transfection. Analyses were carried out as described in Example 3 and results obtained are shown in FIGS. 10 and 11(a) to 11(d). As indicated in the Figures, hP450RAI expression in COS-1 cells promoted conversion of RA into 4-OH-RA and 4-oxo-RA. Total amounts of 4-oxo-RA and 4-OH-RA produced in the transfected cells in comparison to amounts produced in the control cells are shown in FIGS. 11(a) and (b), respectively. Overall, greater amounts of aqueous soluble metabolites were produced in the transfected cells (FIG. 11(c)) and greater amounts of unmetabolized RA were found in control cells (FIG. 11(d)).

Figure 5:
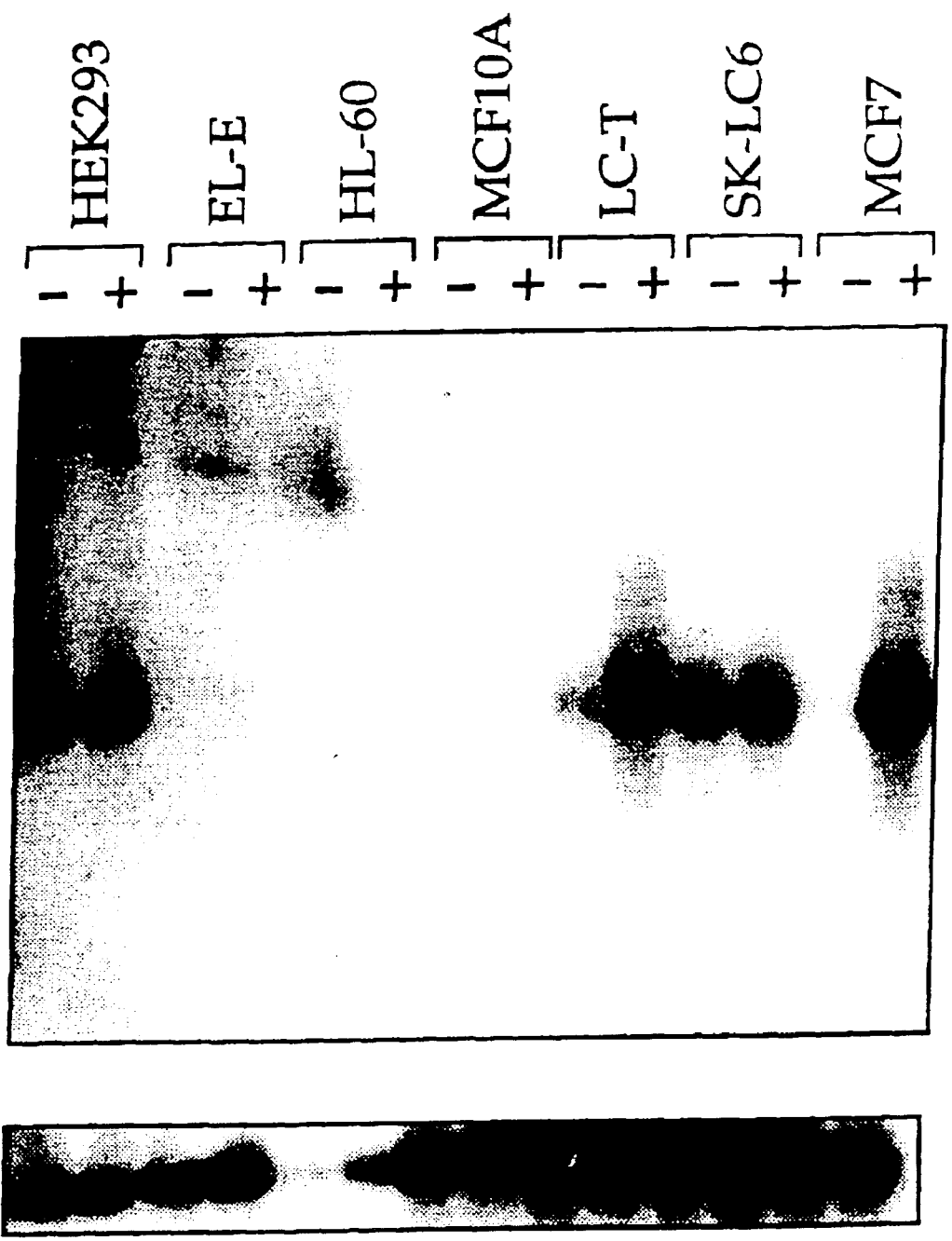
FIG. 5 shows results obtained with human cell lines probed with a α-[$^{32}$P]-dATP labeled probe having the sequence identified as SEQ ID NO:11: HEK293; EL-E; HL-60; MCF10A; LC-T; SK-LC6; and MCF7. (+) indicates pretreatment with $10^6$M RA and (−) indicates no RA pretreatment. The blot was also probed with hGAPDH to control for RNA loading of the gel, shown in the bottom panel.
Figure 6:
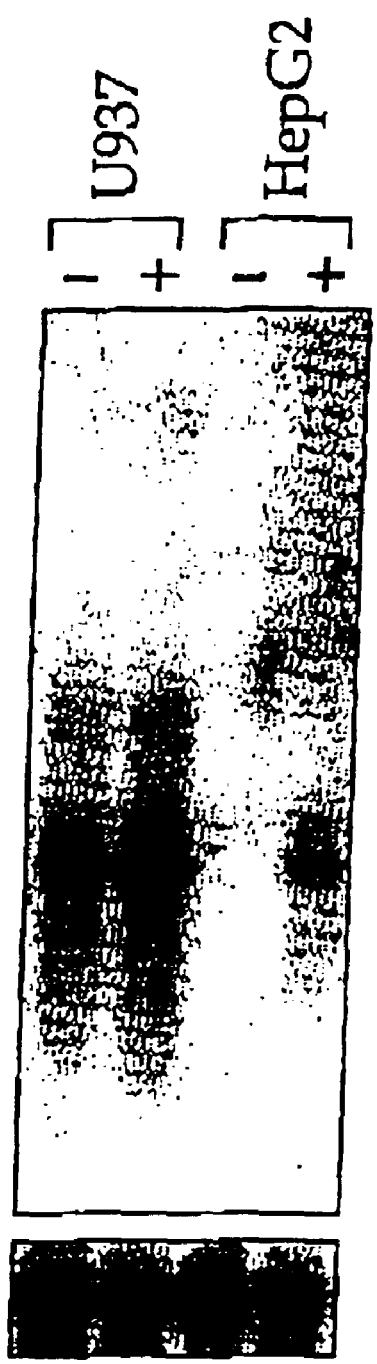
FIG. 6 is similar to FIG. 5 for the cell lines U937 and HepG2.
Figure 7:
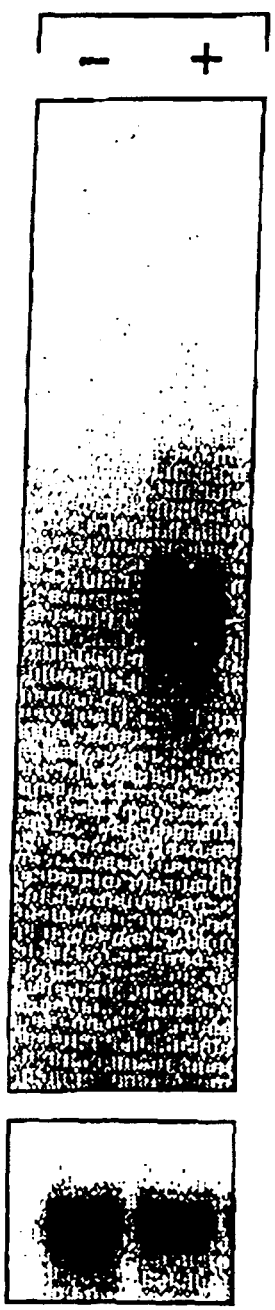
FIG. 7 is similar to FIG. 5 for the NT2 cell line.

The clone sequence (SEQ ID NO:11) was prepared as a $^{32}$[P]-dATP labeled probe to study the inducibility of hP450RAI by RA in several cell lines: HEK293; EL-E; HL-60; MCF10A; LC-T; SK-LC6; MCF7; U937; HepG2; NT2 (See FIGS. 5 to 7). As can be seen, a variety of expression patterns were observed. The SK-LC6 human lung (epithelial) line appeared to constitutively express corresponding mRNA. There was apparently some increase in expression in the HEK293 (human embryonic kidney), LC-T (human lung epithelial), HepG2 (human liver, epithelial in morphology), NT2 (pluripotent human embryonic carcinoma) and U937 (human monomyolocytes) cell lines in response to addition of RA. There was a large dependence on exposure to RA in the MCF7 (human breast carcinoma (epithelial)) cell line. Some cell lines showed no expression in the absence or presence of RA EL-E; HL-60 and MCF10A.

Figure 8:
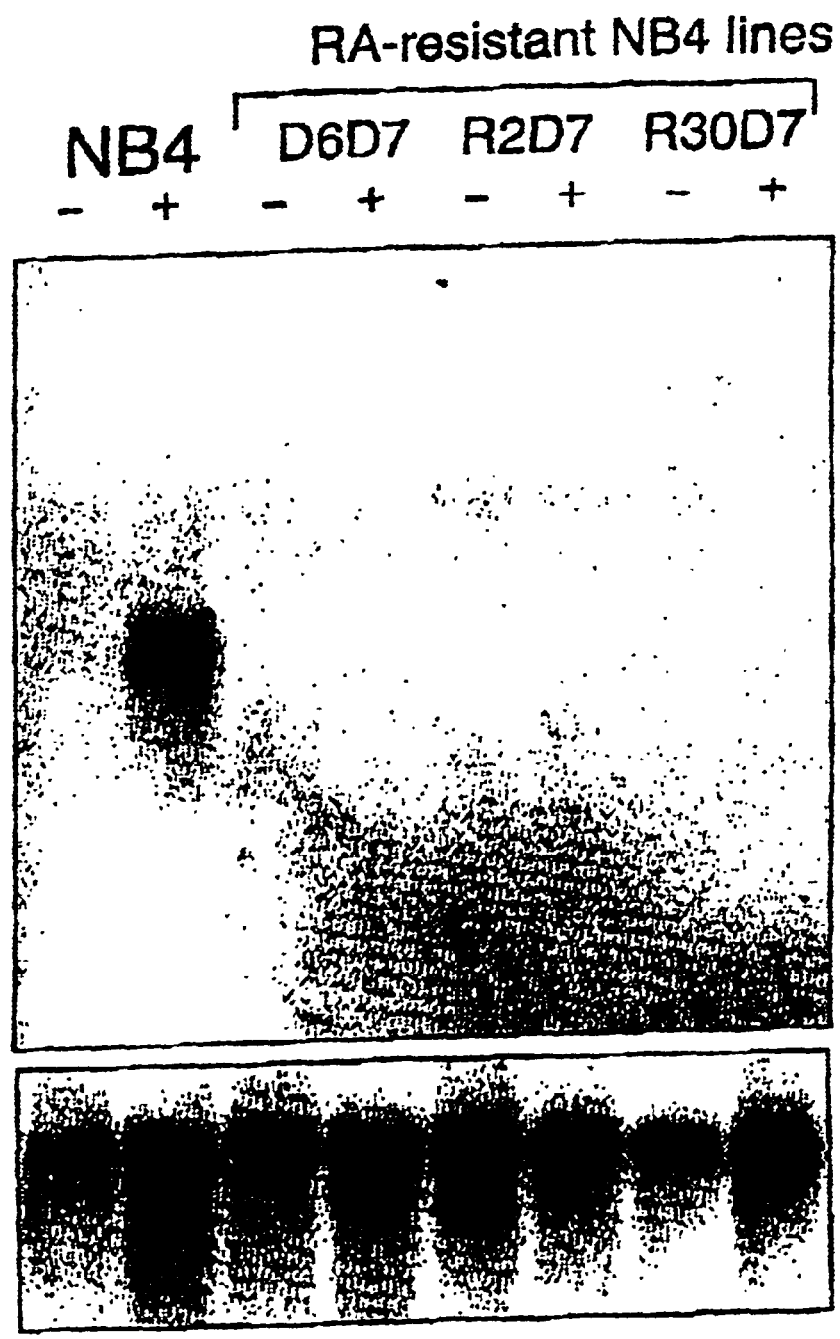
FIG. 8 is similar to FIG. 5 for a normal NB4 cell line (first two lanes) and three individually derived retinoic acid resistant NB4 derivative cell lines.

The $^{32}$[P]-dATP labeled probe was also used to study hP450RAI mRNA expression in a human acute promyelocytic leukemia cell line. Experiments were carried out using the NB4 cell line, isolated from a human acute promyelocytic leukemia patient, and three retinoic acid resistant cell lines were independently derived from NB4. Results are shown in FIG. 8. As can be seen, the normal cells expressed hP450RAI mRNA after treatment with $10^{-6}$M RA, while such expression appeared to be absent for the other cell lines both in the absence and presence of RA.

Analysis of metabolites of MCF10A and MCF7 cell lines exposed to RA was carried out, MCF10A cells having displayed no expression of mRNA and latter having displayed a large dependence of mRNA expression on exposure to RA. The results are shown in FIGS. 12(a) to 12(c). Consistent with the results shown in FIG. 5, the results shown in FIG. 12(a) indicate there was little difference in the lipid soluble activity profiles of the MCF10A cell line exposed to RA and the control. The last two bars of FIG. 12 (c) indicate that total aqueous soluble metabolites were about the same for both the induced and control MCF10A cells. As Indicated in FIG. 12(b), the MCF7 cell line exposed to RA had an elution profile which indicated significantly greater concentrations of 4-OH-RA and 4-oxo-RA than the same cell line not exposed to RA. FIG. 12(c) indicates that the amount of total aqueous soluble metabolites of the MCF7 cells exposed to RA was much greater than that for the control cells. Again, these results are consistent with those obtained in the Northern blot analysis shown in FIG. 5 for the MCF7 cell line.

EXAMPLE 7

Generation of a Stable Cell Line using Human P450RAI: HeLa Cells Expressing Sense Construct For expression in HeLa cells, the human cytochrome P450RAI cDNA (SEQ ID NO:5) was inserted into the XhoI-NotI sites of the multiple cloning site of the Epstein-Barr virus-based vector pCEBV7 [Wilson, 1995]. Stable transfection was performed via the calcium phosphate method [Sambrook, 1989]. Prior to the day of transfection, HeLa cells were seeded at 3.0×10$^6$ cells per 100 mm plate. Approximately 12 µg of DNA were transfected per plate and triplicate plates were employed for the transfection. Selection using hygromycin B began three days after the transfection and continued for approximately three weeks until the development of foci on the plates. The concentration of hygromycin B (100 µg/ml was chosen for selection of cells with high expression of the construct. A killing curve was determined prior to selection which showed that 50 µg/ml of hygromycin was sufficient to kill 50% of the cells in 4 days. Confirmation of the selected HeLa cells expressing the sense construct was determined by Northern blot analysis and probing with full length hP450RAI cDNA (data not shown).

Microsomes were prepared from HeLa cells transfected with the pCEBV7 alone (HeLa P) or from the HeLa cells expressing the P450RAI (HeLa RAI) and exposed to radiolabelled RA for ninety minutes. The results are shown in FIGS. 13(a) and 13(b), in which it can be seen that when microsomes prepared from these cells are incubated with RA, only those from HeLa RAI showed any conversion of retinoic acid to 4-hydroxy-retinoic acid or 4-oxo-retinoic acid.

EXAMPLE 8

Expressing a Fusion Protein Containing Human P450RAI

The cDNA of hP450RAI was inserted into the GST gene fusion vector, pGEX3X using the Sma1 site. The construct generated lacked 177 bp of the N-terminal portion of the hP450RAI cDNA, which encodes a hydrophobic region characteristic of a signal sequence. E. coil (JM109) cells were used for expression of vectors and construct. After screening for positive colonies expressing the construct in the proper orientation, expression of the fusion protein was carried out according to the manual provided by Pharmacia.

GST-hP450RAI fusion protein was generated via electroporation of E. coli (JM109) cells with the construct, followed by induction of gene expression. Expression of the fusion protein is under the control of the tac promoter which is inducible by the lactose analog, isopropylbeta-thiogalactoside (IPTG).

Cultures were grown overnight in LB-ampicillin broth. The following day, approximately 1:100 dilution factor of the overnight culture was transferred to a fresh tube containing LB-ampicillin broth. The culture was allowed to grow for three hours and induced with IPTG to a final concentration of 0.1 mM for an additional 2.5 hours. After induction, the culture was centrifuged at 7,700×g for 10 minutes at 4° C. to sediment the cells. The pellet was resuspended in a ratio of 50 µl of culture/ml of ice-cold 1×PBS. The cells were lysed with a sonicator at 30 second intervals while submerged in ice-water. Triton X-100 was added to the lysed cells to a final concentration of 1% and the mixture was incubated for 30 minutes at 4° C. to allow solubilization. The suspension was subjected to centrifugation at 12,000×g for 10 minutes at 4° C.

Binding of the GST portion of the fusion protein to glutathione beads was used to purify the protein. 2 ml of a 50% slurry of reduced glutathione beads equilibrated with 1×PBS were used per 100 ml of sonicate mixture from above. After the addition of the beads, the material was gently agitated for 30 minutes at room temperature to allow binding of the fusion protein to the beads. The suspension was centrifuged at 500×g for 5 minutes to separate glutathione beads with bound fusion protein from other cellular components. The glutathione beads were washed three times with cold PBS to remove non-specifically bound material.

Figure 14:
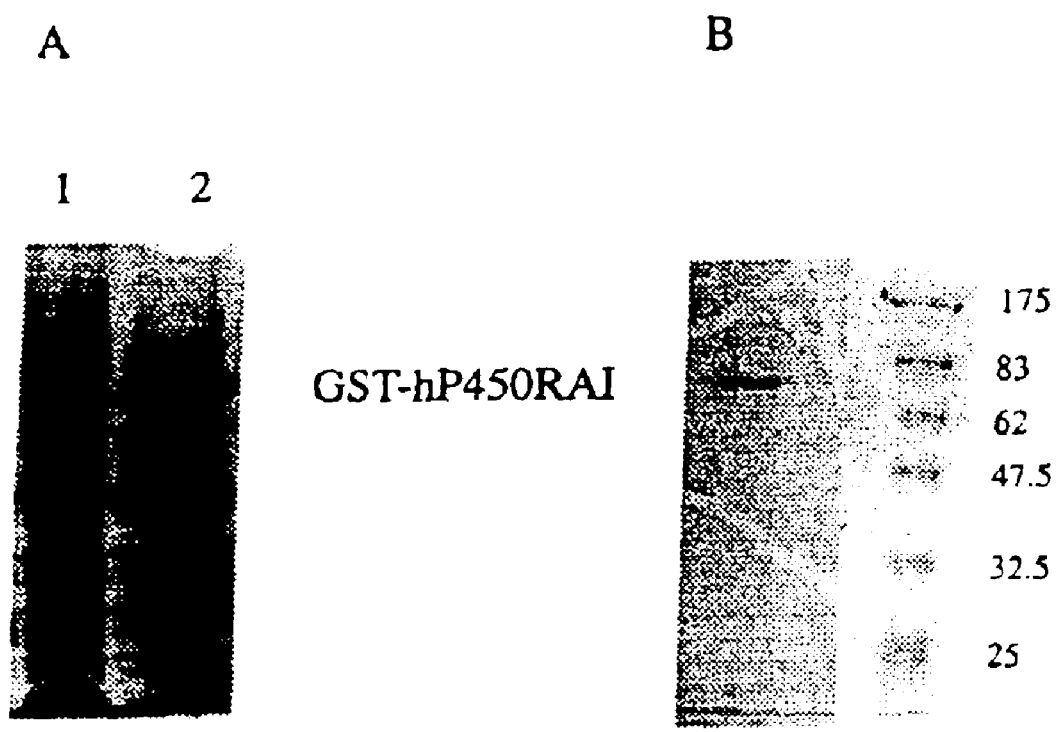
FIG. 14(a) shows SDS-PAGE of the GST-hP450RAI fusion protein. Lane 1 shows the whole cell lysate of *E. coli* expressing the plasmid containing the fusion protein, without induction. Lane 2 shows the whole cell lysate of *E. coli* expressing the plasmid containing the fusion protein after induction with 0.1 mM IPTG.
FIG. 14(b) shows SDS-PAGE of the purified GST-hP450RAI fusion protein after induction with 0.1 mM IPTG, with molecular weight markers at the right hand side indicating the fusion protein to have a molecular weight of about 75 kDa.

The fusion protein was eluted from the glutathione beads using an elution buffer containing reduced glutathione. Approximately 1.0 ml of glutathione elution buffer per 100 ml of sonicate suspension was used. The bound glutathione beads were allowed to mix at room temperature for 10 minutes to elute the fusion protein. Centrifugation of the eluted beads was performed at 500×g for 5 minutes. Both the elution and centrifugation were performed three times. FIGS. 14(a) and (b) show the results of SDS-PAGE of the GST-hP450RAI fusion protein.

It is generally possible to carry out some functional tests with the GST protein covalently attached to the protein of interest, but removal is preferred for the production of antibodies. The GST-hP450RAI fusion protein contains a site recognized by factor Xa. Treatment of the eluted fusion protein with factor Xa yields both the GST protein and hP450RAI protein. Alternatively, it is possible to cleave the fusion protein prior to its elution from the beads, but inadequate cleavage many occur. Approximately 10 µg of factor Xa/mg of fusion protein is used. The material is mixed gently and incubated for approximately 2–16 hours at room temperature. Completion of digestion is checked by gel eletrophoresis at various time points. To purify the protein of interest from the GST protein, binding of cleaved fusion protein suspension with glutathione beads is carried out, followed by centrifugation. The protein of interest remains in the supernatant.

The GST fusion protein can be assayed immunologically or biochemically. Biochemically, treatment of the GST fusion protein with the GST substrate, 1-chloro-2,4-dinitrobenzene (CDNB), indicates the amount of the fusion protein. The GST protein catalyzes the conjugation of CDNB with glutathione, resulting in a CDNB-glutathione product with a strong molar absorptivity at 340 nm. Immunologically, a Western blot of the fusion protein can be probed with an anti-GST antibody which can be readily detected using a secondary antibody such as an anti-goat IgG alkaline phosphatase conjugate, and the standard colorimetric reaction.

EXAMPLE 9

Mapping of Human P450RAI

A 1.3 kb cDNA of hP450RAI was mapped using a P-1 derived artificial chromosome (PAC) library. Mapping of the cDNA and genomic PAC clone was performed by fluorescence in situ hybridization [Lichter, 1990] to normal human lymphocyte chromosomes counterstained with propidium iodide and DAPI. Biotinylated probe was detected with avidin-fluorescein isothiocyanate (FITC). Images of metaphase preparations were captured by a thermoelectrically cooled charge coupled camera (Photometrics, Tucson, Ariz.). Separate Images of DAPI banded chromosomes [Heng, 1993] and FITC targeted chromosomes were obtained. Hybridization signals were acquired and merged using image analysis software and pseudo colored blue (DAPI) and yellow (FTIC) [Boyle, 1992] and overlaid electronically.

Positive hybridization signals were found to be localized to 10q23–24. The band assignment was determined by measuring the fractional chromosome length and by analyzing the banding pattern generated by the DAPI counterstained image.

EXAMPLE 10

Regulation of P450RAI Transcription—Cloning of P450RAI Promoters

Cloning of Zebrafish P450RAI promoter. An adult zebrafish genomic library (1.0×10⁶ pfu) was screened with the full length cDNA corresponding to zP450RAI and positive plaques purified through secondary and tertiary screening. Lambda DNA corresponding to positive plaques was prepared, and the inserts from these clones were excised by restriction enzyme digestion with NotI and subcloned into the plasmid SK+ (Stratagene). Genomic clones were analyzed by restriction enzyme digestion using enzymes from the polylinker of SK+, followed by Southern blotting using an oligonucl otide (5'-GTAGCACGGATGGTG-3' (SEQ ID NO:43)) which hybridizes to the nucleotide sequence encoding the N-terminus of th zP450RAI cDNA to id ntify fragments of the genomic clones which encode the N-terminal region. A 772 base pair PstI fragment which hybridized with the oligonucleotide probe was purified, ligated into the vector SK+ and sequenced using the Core Facility for Protein/DNA Chemistry at Queen's University, Kingston, Canada. Sequence analysis identified this clone as containing the putative initial methionine followed by 129 base pairs of coding sequence, plus 651 nucleotides upstream (5'). Within this 772 base pair fragment, a 402 base pair HindIII fragment was found to contain the putative retinoic acid response element (RARE). This fragment was subcloned into the pGL3B luciferase vector, in both the forward and reverse orientations, (Promega) for transient transfection analyses.

Cloning Human P450RAI promoter. The full length hP450RAI cDNA was used as a probe to identify PAC (P1 artificial chromosome) clones which contain the hP450RAI gene. cDNA from hP450RAI was sent to Canadian Genome Analysis and Technology Program at the Hospital for Sick Children in Toronto, Ontario, Canada for screening of PAC libraries. 5 PAC clones were obtained from this screening, which were verified to contain the hP450RAI gene by restriction enzyme digestion and Southern blotting using the full length hP450RAI cDNA as a probe. One of these clones, 245C7, was found to hybridize to an N-terminal probe from hP450RAI. The probe used was an approximately 130 bp NotI fragment generated from the hP450RAI cDNA. Digestion and Southern blotting of clone 245C7 identified an approximately 3.5 Kb BamHI fragment which hybridized with the NotI fragment. This fragment was subcloned into the plasmid SK+ and sequence data generated at the Core Facility for Protein/DNA Chemistry at Queen's University, Kingston, Canada. Comparison of the sequence data generated with the hP450RAI cDNA identified this 3.5 Kb clone as containing the potential initial methionine and approximately 675 bp upstream (5').

Cloning of mouse P450RAI promoter. A clone of mouse P450RAI genomic DNA approximately 17 kb long was isolated from an SV129λDASH library and subcloned into SK. DNA prepared from this plasmid was digested with various restriction endonucleases, electrophoresed on an agarose gel, and Southern blotted onto nitrocellulose. The resulting blot was hybridized with a $^{32}$P-labelled 230 base pair probe from the N-terminal region of a mouse P450RAI cDNA clone. A SacI fragment approximately 520 base pairs in length was found to hybridize strongly to the probe. This fragment was subcloned into SK cleaved with SacI. Sequence analysis revealed the presence of a DR5-type RARE in the proximal promoter. Flanking this RARE were two BssHII sites 193 base pairs apart. This 193 base pair BssHII fragment was subcloned into the MluI site of pGL3B. Diagnostic restriction digests with XhoI were done to isolate clones with the BssHII fragments in both forward and reverse orientations. Within the 193 base pair fragment is also found the TATA box, 45 base pairs downstream of the RARE. Also included in the 193 base pair BssHII fragment is 83 base pairs of DNA upstream of the DR5 RARE.

The existence of retinoic acid response elements (RAREs), which bind retinoic acid receptors (RARs) and retinoid-x-receptors RXRs is known. The three promoters of P450RAIs from different species described above were thus examined for the presence of RAREs, which might indicate that the regulation of expression of P450RAI is at the transcriptional level. RAREs bind RARs in the form of a heterodimer and typically include a direct repeat of the consensus motif 5'-(A/G)G(T/G)TCA-3'. The repeated sequences can be separated by 1, 2 or 5 nucleotides. FIG. 15 shows the promoter sequences for the zebrafish, human and mouse P450RAI genes. There is a highly conserved motif, indicated by the arrows, which corresponds to a consensus retinoic acid response element known as a DR5, consisting of a direct repeat of a motif AGTTCA separated by 5 nucleotides. This motif in the P450RAI promoters extends over the sequence TGAACT (the complement of AGTTCA). There is also a highly conserved region extending on either side of the DR5, the entire region being boxed. The degree of conservation of this region of the promoter between all three species suggests that this region is important to the control of RA response and that RAR/RXRs are acting in conjunction or competition with other factors binding to this region whose identities are currently unknown. A portion of the conserved region corresponds to the sequence 5'-CAATTAAA-3' which corresponds very closely to a homeodomain binding motif, suggesting that homeobox proteins may facilitate or compete with RAR/RXR heterodimers in the regulation of P450RAI expression.

EXAMPLE 11

Transfection with Mouse P450RAI Promoter

A 195 basepair fragment of genomic DNA containing a portion of the putative promoter for mP450RAI was cloned into the luciferase vector. pGL3B (Promega). For analyses of promoter activity, HepG2 cells were transfected in 6-well dishes with 2 $\mu$g BssHI-pGL3B sense or antisense constructs, described in Example 10, using 5 $\mu$l lipofectAMINE reagent (Gibco, BRL).

On the first day, 48 hours prior to transfection, cells were replated into 6-well plates, with 2.5–3 mls Minimal Essential Medium (MEM) (Gibco, BRL)+ 10% Fetal Calf Serum (Gibco, BRL). On the third day, cells are generally about 50% confluent (HepG2). Before beginning transfection, the medium was replaced with fresh medium and the cells were allowed to grow while preparing DNA/lipofectamine mix. In individual wells of a 48 well plate were mixed 1–5 $\mu$g DNA in 100 $\mu$l optiMEM (Gibco, BRL) and 5 $\mu$l lipofectAMINE reagent in 100 $\mu$l optiMEM, by addition of the DNA/optiMEM to the lipofectAMINE/optiMEM with gentle mixing. This was left to sit 15 min to 1 hour at room temperature. To each well were added 800 $\mu$l optiMEM to obtain a final volume of 1 ml. The cells were washed 2 times in 1xPBS and once in optiMEM. The 1 ml DNA/lipofectamine/optiMEM mixture was added to the cells and incubated for 20 hours at 37° C.

The effects of retinoic acid on promoter activity were analyzed by cotransfecting with varying amounts (100 ng to 1 $\mu$g) of expression vectors including cDNA sequences encoding zebrafish retinoic acid receptor gamma (RAR-$\gamma$) and zebrafish retinoid x receptor alpha (RXR-$\alpha$). Comparisons were made between cells transfected with the control pGL3B vector, those with the sense construct and those with the antisense construct by incubating one set of the transfected cells with DMSO and the other set with $10^{-6}$M RA in DMSO.

On the fourth day, the medium was removed and replaced with fresh medium (+10% FBS). The RA or vehicle was added as required to the wells and mixed gently by swirling the plate. For a 6 well plate 3 $\mu$l of $10^{-3}$M RA in DMSO were added. Control wells received 3 $\mu$l DMSO. The plates were covered in foil and incubated for 24 hours at 37° C.

On the fifth day, cells were harvested by removing the medium and washing twice in 1xPBS. Then, on ice, 100 $\mu$l lysis buffer (1% Triton X-100, 25 mM glycylglycine, pH 7.8, 15 mM MgSO$_4$, 4 mM EGTA, 1 mM DTT (added fresh just before use)) were added, and the cells were scraped off the bottom of the dish and transferred to a 1.5 ml microcentrifuge tube, spun for 5 minutes at 12000xg, and the supernatant recovered.

Figure 16:
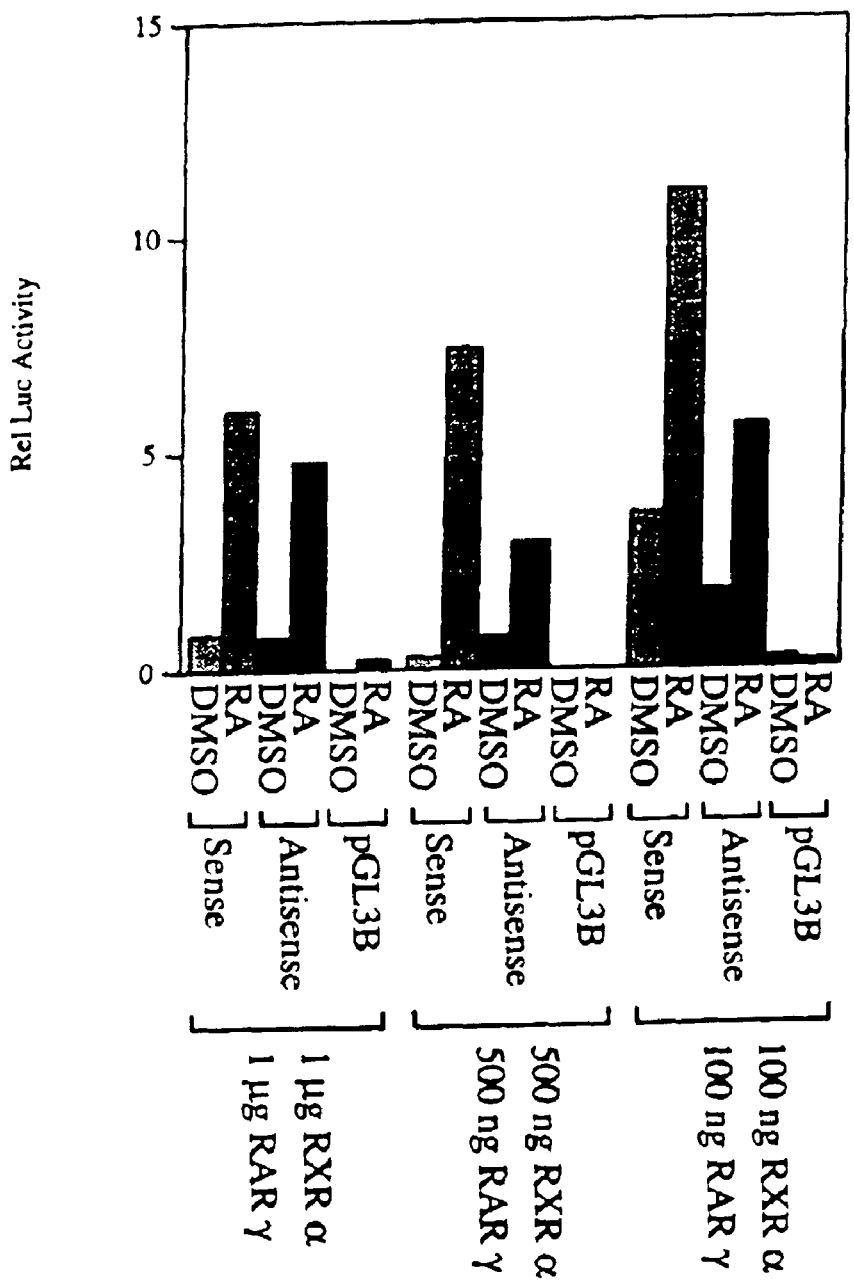
FIG. 16 shows relative luciferase activity induced in cells containing a luciferase vector into which was cloned a portion of the putative promoter for mP450RAI. Luciferase activity was measured in cell extract supernatants from cells transfected with 3 concentrations of expression vectors comprising cDNAs encoding RXRα and RARγ (100 ng, 500 ng, and 1 μg) along with a luciferase-based reporter gene including either the sense or antisence promoter sequence, or no promoter sequence, grown in presence and absence of RA.

To assay for luciferase activity, 20 $\mu$l supernatant from lysed, pelleted cells were transferred to a fresh tube. 80 $\mu$l luciferase assay buffer were added and a reading in millivolts in a luminometer was taken immediately. The luciferase assay buffer was 20 mM Tricine, 1.07 mM (MgC0$_3$)$_4$Mg(OH)$_2$*5H$_2$O, 2.67 mM MgSO$^4$, 0.1 mM EDTA, 33.3 mM DTT, 0.27 mM Coenzyme A, 0.47 mM Luciferin, 0.53 mM ATP. The results are shown in FIG. 16, in which it can be seen that enhanced luciferase activity was observed in the presence of RA, RXR$\alpha$ and RAR$\gamma$, for both orientations of the promoter sequence, although enhancement appears to be greater for the sense construct.

EXAMPLE 12

Inhibition of P450RAI Induction by 4-Hydroxyphenylretinamide

It has recently been reported that 4-hydroxyphenylretinamide (4-HPR) inhibits RA-induced RA catabolism by NB4 cells [Taimi, 1997]. It was suggested that 4-HPR may inhibit the cytochrome P450 enzyme(s) responsible for RA oxidation to competitively inhibit RA catabolism. However, any such enzymes were not identified, no explanation of the nature of 4-HPR inhibition of RA catabolism was provided, and no evidence of 4-HPR metabolism was observed.

Figure 17:
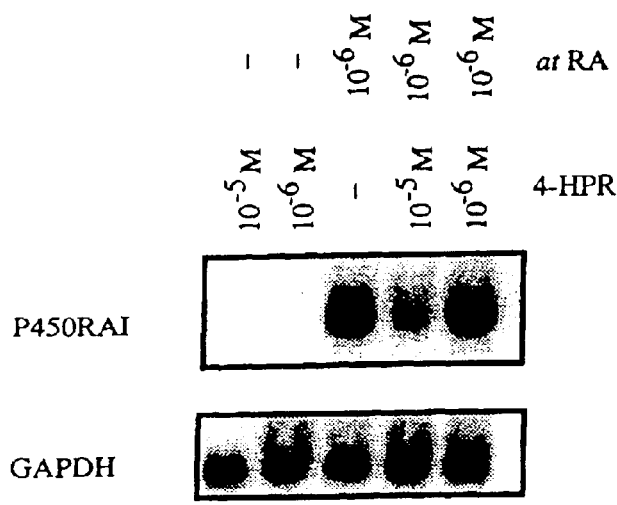
FIG. 17 shows inhibition of P450RAI mRNA in MCF7 cells by 4-hydroxy-phenylretinamide (4-HPR).

Experiments to determine the effect of 4-HPR on the induction of P450RAI were thus carried out. FIG. 17 illustrates the ability of the synthetic retinoid, 4-HPR to inhibit the induction of P450RAI by RA. MCF7 cells were grown in culture in minimal essential medium (MEM) (Gibco) supplemented with 10% fetal calf serum, insulin (0.01 mg/mL), MEM non-essential amino acids (as directed by the manufacturer—Gibco), sodium pyruvate (500 nM), L-glutamine (2 mM) gentamycin (10 $\mu$g/mL), penicillin (5 $\mu$g/mL), streptomycin (5 $\mu$g/mL), and fungizone (200 ng/mL). MCF7 cells cultured in parallel were treated for 12 hours with: 10 $\mu$M 4HPR; 1 $\mu$M 4HPR; 1 $\mu$M RA; 1 $\mu$M RA and 10 $\mu$M 4-HPR; or 1 $\mu$M RA and 1 $\mu$M 4-HPR. At the end of the 12 hour treatment, total RNA was extracted from the cells using TRIzol reagent (as outlined by the manufacturer—Gibco). P450RAI message in the total RNA preparations was analyzed by northern blot hybridization. The blot was reprobed with a probe corresponding to the GAPDH cDNA to control for equivalent loading of RNA in each lane of the blot The results indicate that 4-HPR treatment alone does not induce the P450RAI message. As expected, RA treatment of MCF7 cells results in a marked induction of P450RAI message following 12 hours of incubation. However, when cells are treated with RA in the presence of 10 $\mu$M 4-HPR, there is a noticeable suppression of P450RAI induction.

EXAMPLE 13

P450RAI Expression in the Presence of Retinoic Acid

Figure 18:
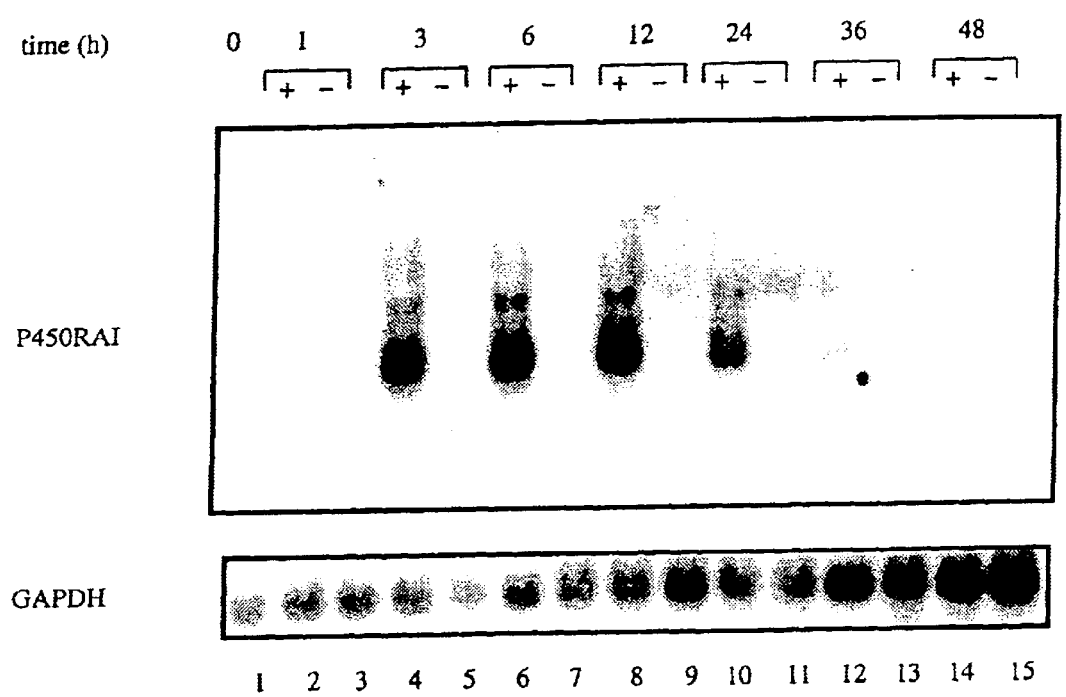
FIG. 18 shows expression of cytochrome P450RAI in MCF7 cells by northern blot analysis, over time, after administration of all-trans retinoic acid.

FIG. 18 shows a time course of expression of cytochrome p450RAI following treatment of MCF7 breast epithelium adenocarcinoma cells with 1 µM all-trans retinoic acid. In this northern blot analysis, total RNA was extracted at the indicated time points and transferred to nitrocellulose following electrophoresis in a 1% agarose, 0.66 M formaldehyde gel. The nitrocellulose was then probed with radioactively labelled human cytochrome p450RAI cDNA or GAPDH cDNA to control for equivalence of mRNA loading. This shows that after 3 hours of incubation with retinoic acid, the MCF7 cells express high levels of P450RAI message and following 12 hours of exposure, the message declines sharply, possibly indicating that the metabolic activity of induced P450RAI protein is reducing the concentration of active retinoic acid in the surrounding medium. This strongly suggests that the induction of P450RAI in MCF7 cells forms an autoregulatory negative feedback loop.

EXAMPLE 14

P450RAI Expression in the Presence of Retinoic Acid and Ketoconazole

Figure 19:
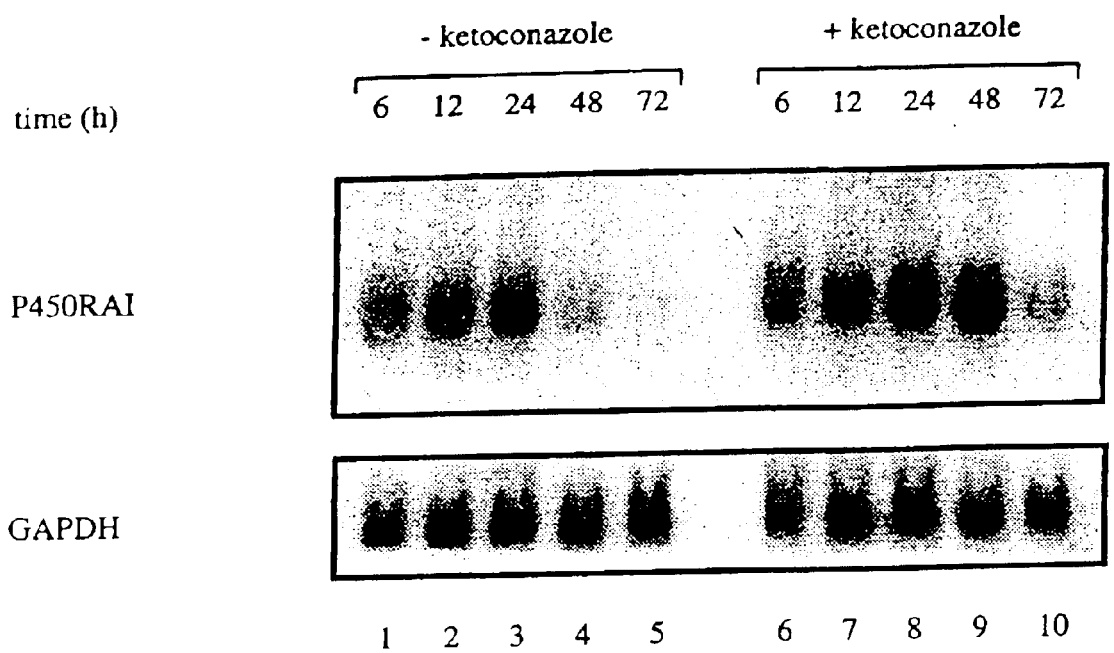
FIG. 19 shows expression of cytochrome P450RAI in MCF7 cells by northern blot analysis, over time, after administration of all-trans retinoic acid alone, and in the presence of all-trans retinoic acid and ketoconazole.

FIG. 19 shows a time course of P450RAI mRNA expression in MCF7 cells similar to that described in FIG. 18, except that the effect of the broad spectrum cytochrome p450 inhibitor ketoconazole on P450RAI expression was examined. In the absence of ketoconazole, lanes 1 to 5 in FIG. 19 a time course similar to that shown in FIG. 18 is shown. In cells which were exposed to 1 µM ketoconazole (replenished every 12 hours following initial treatment), cytochrome P450RAI message was detectable at high levels at 24 and 48 hour time points indicating that the breakdown of retinoic acid can be inhibited by a cytochrome P450 inhibitor and that P450RAI metabolism may be responsible for the sharp drop in P450RAI message in the absence of ketoconazole. The example illustrates a method of identifying P450RAI inhibitors.

EXAMPLE 15

P450RAI Expression in the Presence of Am580

Figure 20:
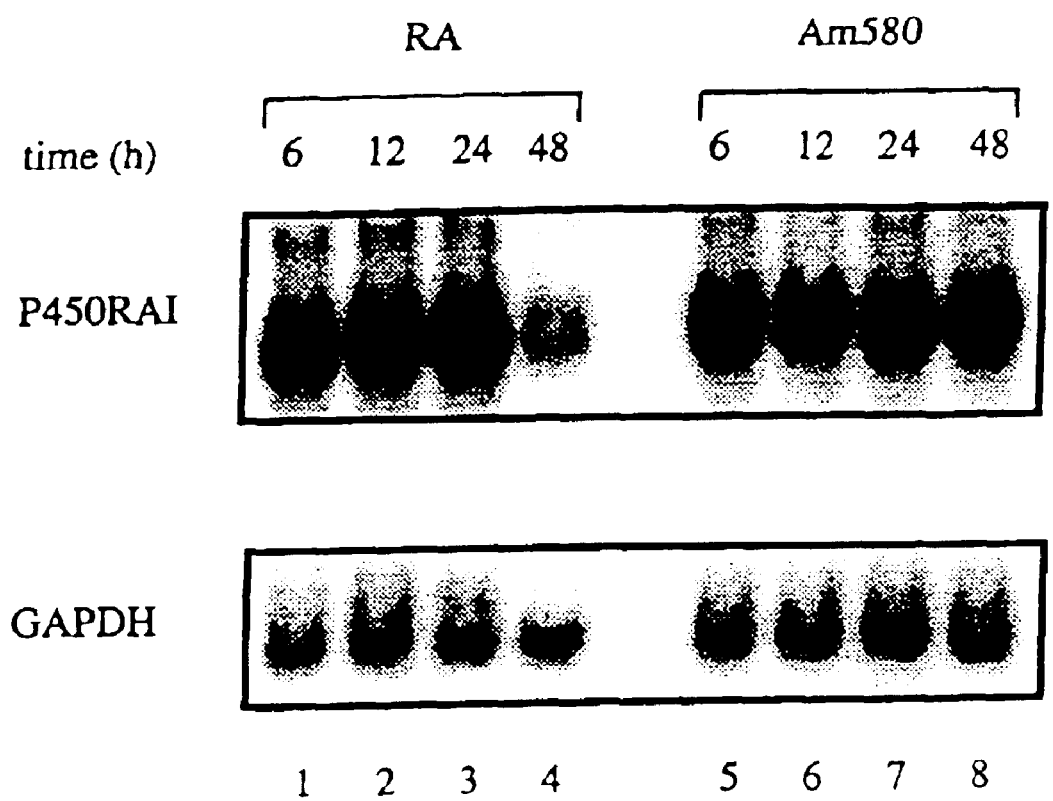
FIG. 20 shows expression of cytochrome P450RAI in MCF7 cells by northern blot analysis, over time, after administration of all-fans retinoic acid and after administration of Am580.

FIG. 20 shows a time course of P450RAI mRNA expression in MCF7 cells similar to that described in FIG. 18, except that a comparison was made between the retinobenzoic acid derivative Am580 and all-trans retinoic acid. Retinoic acid shows a typical time course of induction of P450RAI message, lanes 1 to 4, FIG. 20. Am580 induces P450RAI message to levels comparable to those observed following treatment with retinoic acid. Notably, whereas P450RAI message has declined sharply between 24 and 48 hours, for retinoic add treated cells, the levels of P450 RA in Am580 treated cells remains high at this time point. This indicates that the synthetic retinoid Am580 is resilient to metabolism in these cells and illustrates the utility of identifying such compounds for therapeutic use. For example, the resistance to retinoic acid treatment observed in acute promyelocytic leukemia due to increased retinoic acid metabolism [Warrell, 1994] might be circumvented by treatment with a metabolism-resistant retinoid. P450RAI protein may be a useful agent for screening for these types of compounds.

EXAMPLE 16

Monoclonal Antibodies to P450RAI

Monoclonal antibodies (Mab's) specific for P450RAI are useful, for example, for diagnostic purposes such as for determining P450RAI protein levels in the identification of normal and tumor tissues which metabolize RA. To produce these antibodies, purified P450RAI protein is prepared. The human P450RAI protein is produced in bacterial cells as a fusion protein with glutathione-Stransferase using the vector pGEX2 (Pharmacia). This permits purification of the fusion protein by GSH affinity chromatography. In another approach, P450RAI is expressed as a fusion protein with the bacterial maltose binding domain. The fusion protein is thus recovered from bacterial extracts by passing the extract over an amylose resin column followed by elution of the fusion protein with maltose. For this fusion construct, the vector pMalC2, commercially available from New England Biolabs, is used. This vector has been used in the past, for example, to overexpress nuclear receptor proteins which were recovered in high yields for functional studies and the production of receptor specific antisera [Ohno, 1993]. The preparation of a second fusion protein is also useful in the preliminary screening of MAb's.

The generation of hybridomas expressing monoclonal antibodies recognizing P450RAI protein is carried out as follows: BALB/c mice are injected intraperitoneally with protein/adjuvant three times at one-month intervals, followed by a final injection into the tail vein shortly prior to cell fusion. Spleen cells are harvested and fused with NS-1 myeloma cells (American Type Culture Collection, Rockville. Md.) using polyethylene glycol 4000 according to standard protocols [Kennett, 1979; Mirski, 1989]. The cell fusion process is carried out as described in more detail below.

The fused cells are plated into 96-well plates with peritoneal exudate cells and irradiated spleen cells from BALB/Ccmice as feeder layers and selection with hypoxanthine, aminopterin, and thymidine (HAT medium) is performed.

An EUSA assay is used as an initial screening procedure. 1–10 µg of purified P450RAI (cleaved from the fusion protein) in PBS is used to coat individual wells, and 50–100 µl per well of hybridome supernatants is incubated. Horseradish peroxidase-conjugated anti-mouse antibodies are used for the colorimetric assay.

As a secondary screening, breast epithelial carcinoma MCF-7 cells are used as a source of P450RAI determinant. As indicated above, untreated MCF-7 cells exhibit no detectable expression of P450RAI message and no detectable RA metabolizing activity, whereas there is a rapid and striking induction of both in cells treated with RA. Untreated MCF-7 cells thus serve as a negative control for background. MCF-7 cells are aliquotted into 96 well plates one day prior to assay. Cells are fixed and permeabilized with methanol. Hybridoma supernatants are added and fluorescein isothiocyanate (FITC)-conjugated anti-mouse antibodies are used for screening using a standard fluorescence microscope.

Positive hybridomas are cloned by limiting-dilution and grown to large-scale for freezing and antibody production. Various positive hybridomas are selected for usefulness in western blotting and immunohistochemistry, as well as for cross reactivity with P450RAI proteins from different species.

The selected MAb's are useful for monitoring the levels of expression of P450RAI protein following RA treatment in cell culture and in tissues. P450RAI protein expression may be a prognostic indicator for determining whether a particular tumor will respond to RA treatment. There is also a wide intersubject variability in baseline RA metabolism and there is evidence suggesting that subjects with a high rate of RA metabolism have a higher incidence of squamous or large cell cancers of the lung [Rigas, 1996]. Once useful antibodies are characterized, these antibodies are used to survey tumor tissue samples for P450RAI expression.

Protocol For Production of Mouse Hybridomas

Fusion. Feeder cells (spleen and peritoneal exudate cells) are plated. 24 to 48 hours before fusion, mouse myeloma cells are taken off drug (8-azaguanine 20 µg/ml) and counted to ensure that there are at least 50×10$^5$ cells. 2 g of PEG 4000 are autoclaved in a glass tube for 15 minutes and maintained at 60° C. for use or alternatively stored at room temperature and remelted in a 60° C. water bath when needed.

BALB/c mice are immunized as per desired schedule. The final injection is given intravenously in the tail vein. Fusion of immunized spleen cells is carried out 3 or 4 days after the intravenous injection. Spleen from each animal is collected separately; eye sera for ELISA if desired.

A single cell suspension is prepared using a Teflon pestle and decanting connective tissue. The suspension is washed 1× in serum-free medium. Each spleen has about 10×10$^5$ cells. The myeloma cells are collected, counted and wased in in serum-free medium.

The cells are then fused. A small beaker of water, and serum-free medium (37° C.) are prepared and the PEG melted at 50–60° C. The immunized spleen cells and myeloma cells are mixed in a 50 ml TC tube (recommended ratios vary from 1:1 to 2:1) and the cells are washed once with serum-free medium. The supernatant is carefully discarded. 2.4 ml pre-warmed serum-free medium is added immediately with pipette to the melted PEG and mixed, maintaining the temperature at 37° C. in beaker of warm water. The PEG should be light pink. If it is yellow, another aliquot should be used. 0.5–1.0 ml of PEG is added dropwise to the cell pellet over 1 minute with gentle rotation of the tube or gentle stirring to ensure mixing. The tip of the addition pipette is placed directly over the cell pellet. The tube is swirled gently in 37° C. water bath for 90 seconds with the blunt end of a 3 ml pipette Lip and 10 ml warm serum-free medium added slowly over 610 minutes while rotating tube gently to bring the volume up to 20–50 ml. The tube is maintained at 37° C. for at least 20 minutes to obtain cell fusion and then the cells are washed 2× with serum-free medium. The cells are centrifuged and gently resuspended in 100 ml of pro-warmed medium +10–20% FBS. 100 µl/well aliquotted in 96 well plates. Assuming one spleen fused with 100×10$^6$ cells myeloma fusion partner, about 10 plates are needed. On the following day, 100 µl medium is removed and 100 µl 2×HAT added. Feed with with 1×HAT medium for 1 to 3 weeks, then feed with HT medium (i.e., remove 1/2 HAT medium and replace with equal volume HT medium).

Preparation of Peritoneal Exudates and Spleen Feeder Cells.

A sacrificed mouse is sprayed with 70% alcohol, skin is nicked and torn apart, with care being taken not to cut the peritoneum. The peritoneum is lifted with forceps and a needle is introduced; 5 ml of serum-free medium is slowly injected. The abdomen is massaged and the fluid is slowly sucked up, collected in a sterile tube and kept on ice. The volume is brought up to 5 ml. The spleen is obtained and placed in a sterile tube containing serum-free medium. The spleen is gently mashed with a sterile Teflon pestle. Clumps are allowed to settle and the cells are decanted into a clean tube, care being taken to avoid including connective tissue, in order to minimize fibroblast growth. The sample is irradiated at 4500 R. Cells are washed once with serum-free medium, placed into 96-well plates [one spleen/10 plates (approximately 2–5×10$^5$ cells/well) and peritoneal exudate cell suspension (PECS) (<3×10$^3$ cells/well) in a total volume of 100 µl/well] and incubated at 37° C. until ready to be used. They can also be stored in sterile tube overnight at 4° C.

Discussion

It is possible to compare the zP450RAI, mP450RAI and hP450RAI sequences described above. Of the 492 amino acids of zP450RAI (SEQ ID NO:2), it is possible to align 334 amino adds with the 497 amino acids of hP450RAI (SEQ ID NO:4). See FIG. 9. On this basis, there is about 68% homology between the human and fish proteins. The degree of homology between the two amino acid sequences is slightly greater towards the C-terminus than in the N-terminal region. It also appears as though nucleic acid sequences encoding the conserved sequence Met-Lys-Arg-Gln-Lys (amino acid numbers 70 to 74 of zP450RAI) can be used as a probe to obtain corresponding proteins from cDNA libraries of other species. The amino acid identity between the human and mouse P450RAI sequences is greater than 93%.

As shown above, RA-induced expression of a protein by the cells described herein involves a regulatory sequence which is located upstream of the coding sequence of DNA that it controls. As it occurs in nature, the protein is P450RAI, whether in cells of the zebrafish, human, mouse or other organism. Such a cell can be modified by incorporating DNA encoding a different protein into the region of the gene which encodes P450RAI, as exemplified above with DNA encoding luciferase. An aspect of the present invention is thus a regulatory DNA sequence, responsive to the presence of RA, operably linked to a protein-encoding sequence and incorporated into a conventional genetically engineered protein-producing cell. Production of the desired protein can be induced by exposure of the cell to RA.

Antisense nucleic acids or oligonucleotides (RNA or preferably DNA) that inhibit cellular RA-induced P450RAI production can be used to inhibit metabolism of RA by P450RAI [Monia, 1996]. Antisense oligonucleotides, typically 15 to 20 bases long, bind to the sense mRNA or pre mRNA region coding for the protein of interest, which can inhibit translation of the bound mRNA to protein. The cDNA sequence encoding hP450RAI can thus be used to design a series of oligonucleotides which together span a large portion, or even the entire cDNA sequence. These oligonucleotides can be tested to determine which provides the greatest inhibitory effect on the expression of the protein [Stewart, 1996]. This can be done by exposing cells to the various oligonucleotides and measuring subsequent changes in hP450RAI activity or by using antibodies to screen for inhibition of P450RAI synthesis. The most suitable mRNA target sites include 5'- and 3'-untranslated regions as well as the initiation codon. Other regions might be found to be more or less effective. Alternatively, an antisense nucleic acid or oligonucleotide may bind to P450RAI DNA coding or regulatory sequences.

Rather than reducing RA metabolism by inhibiting P450RAI gene expression at the nucleic acid level, activity of the P450RAI protein may be directly inhibited by binding to an agent, such as, for example, a suitable small molecule or a monoclonal antibody.

The present invention thus includes a method of screening drugs for their effect on activity of a retinoic acid inducible protein. The method includes exposing the protein to a prospective inhibitor drug and determining the effect on protein activity. The measured activity might be hydroxylation of a retinoid, particularly all-trans retinoic acid, or hydroxylation of a retinoic acid, particularly all-trans retinoic add, at the 4 position of the β-ionone ring thereof. For screening drugs for use in humans, hP450RAI itself is particularly useful for testing the effectiveness of such drugs. Prospective drugs could also be tested for inhibition of the activity of other P450 cytochromes, which are desired not to be inhibited. In this way, drugs which selectively inhibit hP450RAI over other P450s could be identified.

Another system for screening for potential inhibitors of a P450RAI protein includes a stably transfected cell line having incorporated therein DNA of a reporter gene (e.g., β-galactosidase, firefly luciferase, or the like) and of the P450RAI, in which expression of both genes is inducible by exposure of the cells to RA. Expression of the reporter gene provides a measure of the induction of the expression system and therefore provides an indication of the amount of RA present Exposure of the cells to RA leads to RA metabolism and, with time, such metabolism leads to a decrease in the degree of induction which is indicated by the reporter protein. Exposure of the cells to RA in the presence of an agent that inhibits P450RAI metabolism of RA results in decreased RA metabolism, whereas exposure of the cells to RA in the presence of an agent that does not inhibit P450RAI metabolism of RA has no effect on RA metabolism. A comparison of expression of the reporter gene in the presence of RA alone and in the presence of both RA and a potential inhibitory drug thus gives a measure of the effectiveness of the drug in inhibiting metabolism of RA by the P450RAI protein.

One system for screening for potential inhibitors of a P450RAI protein includes a cell line in which the endogenous P450RAI gene is not present or not functional or not expressed. In this cell line, a cytochrome P450RAI expression vector and an RA-inducible reporter gene are incorporated such that exposure of the cell line to RA results in metabolism of RA by the expressed P450RAI protein and a degree of induction of the reporter gene based on remaining active RA. The addition of an inhibitor of P450RA) will decrease the rate of metabolism/degradation of RA and therefore increase the activation/induction of the RA sensitive reporter gene.

Given the high degree of conservation of the promoter regions of the mouse, human and zebrafish P450RAI promoter regions, it is likely that RA regulates P450RAI expression through a transcriptional mechanism involving the RARE conserved in the promoters of all three species. This is supported by studies which show the rapid and RA-dependent expression of P450RAI in a number of cell lines. Since P450RAI message is induced so strongly a reporter gene may be a useful indicator of RA activity n vivo as well as in vitro. Thus, the P450RAI promoter linked to a reporter gene provides a tool for screening retinoids or other compounds which have the ability to block or inhibit P450RAI induction. For example, the P450RAI reporter gene could be stably or transiently introduced into a cell line such that when the cells are exposed to a certain level of retinoid or other agent, the concentration will be reflected in reporter gene activity. Such transfection assays can be carried out in a manner similar to those described by Petkovich et al., for example [Petkovich, 1987; Ohno, 1994].

The invention thus provides a system for screening potential inhibitors of RA catabolism by a P450RAI protein. The system includes a transfected cell line having incorporated therein DNA of a reporter gene, for example the luciferase gene exemplified above, in which expression of the reporter gene is inducible by exposure of the cells to RA. In this system, the P450RAI gene is omitted, that is the reporter gene is under the control of the native promoter for the P450RAI gene. Expression of the reporter gene provides a measure of the induction of the expression system and therefore provides an indication of the amount of mRNA produced in response to exposure of the cells to RA. Exposure of the cells to RA in the presence of an agent that inhibits induction of the expression system indicates that the agent is a potential inhibitor of RA catabolism, i.e., provides a measure of the effectiveness of the agent as a drug in inhibiting the expression of P450RAI gene and thus metabolism of RA.

There is the possibility that cellular retinoic acid-binding protein (CRABP) [Adamson, 1993] is involved in binding of a retinoid substrate to a P450RAI protein of the present invention. The effect of the presence of CRABP, derivatives, synthetic fragments or analogs thereof could thus be determined according to screening methods of the present invention; effectiveness of such agents in enhancing RA metabolism can also be determined.

It will of course be understood, without the intention of being limited thereby, that a variety of substitutions of amino acids is possible while preserving the structure responsible for retinoid metabolizing activity of the proteins disclosed herein. Conservative substitutions are described in the patent literature, as for example, in U.S. Pat. No. 5,264,558. It is thus expected, for example, that interchange among non-polar aliphatic neutral amino acids, glycine, alanine, proline, valine and isoleucine, would be possible. Likewise, substitutions among the polar aliphatic neutral amino acids, serine, threonine, methionine, asparagine and glutamine could possibly be made. Substitutions among the charged acidic amino acids, aspartic acid and glutamic acid, could probably be made, as could substitutions among the charged basic amino acids, lysine and arginine. Substitutions among the aromatic amino acids, including phenylalanine, histidine, tryptophan and tyrosine would also likely be possible. These sorts of substitutions and interchanges are well known to those skilled in the art. Other substitutions might well be possible. Of course, it would also be expected that the greater the percentage of homology, i.e., sequence similarity, of a variant protein with a naturally occuring protein, the greater the retention of metabolic activity. Of course, as protein variants having the activity of P450RAI as described herein are intended to be within the scope of this invention, so are nucleic acids encoding such variants.

A further advantage may be obtained through chimeric forms of the protein, as known in the art. A DNA sequence encoding the entire protein, or a portion of the protein, could thus be linked, for example, with a sequence coding for the C-terminal portion of E. coli β-galactosidase to produce a fusion protein. GST-CYPRAI fusion proteins are described in the above examples. An expression system for human respiratory syncytial virus glycoproteins F and G is described in U.S. Pat. No. 5,288,630 issued Feb. 22, 1994 and references cited therein, for example.

A recombinant expression vector of the invention can be a plasmid, as described above. The recombinant expression vector of the invention further can be a virus, or portion thereof, which allows for expression of a nucleic acid introduced into the viral nucleic acid. For example, replication defective retroviruses, adenoviruses and adeno-associated viruses can be used.

The invention provides a recombinant expression vector comprising a DNA molecule of the invention cloned into the expression vector in an antisense orientation. That is, the DNA molecule is operatively linked to a regulatory sequence in a manner which allows for expression, by transcription of the DNA molecule, of an RNA molecule which is antisense to the nucleotide sequence of SEQ ID NO:3, SEQ ID NO:5, SEQ ID NO:31. Regulatory sequences operatively linked to the antisense nucleic acid can be chosen which direct the continuous expression of the antisense RNA molecule in a variety of cell types, for instance a viral promoter and/or enhancer, or other regulatory sequences can be chosen which direct tissue or cell type specific expression of antisense RNA.

The recombinant expression vectors of the invention can be used to make a transformant host cell including the recombinant expression vector. The term "transformant host cell" is intended to include procaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride coprecipitation, DEAE-dextran-mediated transfection, lipofection, electroporation or microinjection. Suitable methods for transforming and transfecting host cells are known [Sambrook, 1989].

The number of host cells transformed with a recombinant expression vector of the invention by techniques such as those described above will depend upon the type of recombinant expression vector used and the type of transformation technique used. Plasmid vectors introduced into mammalian cells are integrated into host cell DNA at only a low frequency. In order to identify these integrants, a gene that contains a selectable marker (e.g. resistance to antibiotics) is generally introduced into the host cells along with the gene of interest. Preferred selectable markers include those which confer resistance to certain drugs, such as G418 and hygromycin. Selectable markers can be introduced on a separate plasmid from the nucleic acid of interest or, preferably, are introduced on the same plasmid. Host cells transformed with one or more recombinant expression vectors containing a nucleic acid of the invention and a gene for a selectable marker can be identified by selecting for cells using the selectable marker. For example, if the selectable marker encodes a gene conferring neomycin resistance (such as pRc/CMV), transformant cells can be selected with G418. Cells that have incorporated the selectable marker gene will survive, while the other cells die.

Certain nucleic acids of the invention encode proteins which "have biological activity of a cytochrome P450RAI". The biological activity of a cytochrome P450RAI is the ability to oxidize a retinoid. Such activity can be tested for as described above.

The invention provides purified proteins having biological activity of P450RAI. The terms "isolated" and "purified" each refer to a protein substantially free of cellular material or culture medium when produced by recombinant DNA techniques, or chemical precursors or other chemicals when chemically synthesized. In certain preferred embodiments, the protein having biological activity of P450RAI comprises an amino acid sequence identified as SEQ ID NO:2 or SEQ ID NO:4 or SEQ ID NO:32. Alternatively, preferred proteins encoded by a nucleic add comprising the nucleotide sequence identified as SEQ ID NO:3 or SEQ ID NO:5 or SEQ ID NO:31, as defined above, are encompassed by the invention. Furthermore, proteins having biological activity of P450RAI that are encoded by nucleic acids which hybridize under stringent conditions, as discussed above, to a nucleic acid comprising a nucleotide sequence identified as SEQ ID NO:3 or SEQ ID NO:5 or SEQ ID NO:31 are encompassed by the invention. P450RAIs of the invention can be obtained by expression in a suitable host cell using techniques known in the art. Suitable host cells include prokaryotic or eukaryotic organisms or cell lines, for example, yeast, E. coli, insect cells and COS 1 cells. The recombinant expression vectors of the invention, described above, can be used to express a protein having P450RAI activity in a host cell in order to isolate the protein. The invention provides a method of preparing an purified protein of the invention comprising introducing into a host cell a recombinant nucleic acid encoding the protein, allowing the protein to be expressed in the host cell and isolating and purifying the protein. Preferably, the recombinant nucleic acid is a recombinant expression vector. Proteins can be isolated from a host cell expressing the protein and purified according to standard procedures of the art, including ammonium sulfate precipitation, column chromatography (e.g. ion exchange, gel filtration, affinity chromatography, etc.), electrophoresis, and ultimately, crystallization [see generally, "Enzyme Purification and Related Techniques", *Methods in Enzymology*, 22, 233–577 (1971)].

Alternatively, the protein or parts thereof can be prepared by chemical synthesis using techniques well known in the chemistry of proteins such as solid phase synthesis [Merrifield, 1964], or synthesis in homogeneous solution [Houbenwcyl, 1987].

The protein of the invention, or portions thereof, can be used to prepare antibodies specific for the proteins. Antibodies can be prepared which bind to a distinct epitope in an unconserved region of a particular protein. An unconserved region of the protein is one which does not have substantial sequence homology to other proteins, for example other members of the P450 family of cytochromes. Conventional methods can be used to prepare the antibodies. For example, by using a peptide of a P450RAI protein, polyclonal antisera or monoclonal antibodies can be made using standard methods. As demonstrated in Example 16, a mammal, (e.g. a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant The progress of immunization can be monitored by detection of antibody titers in plasma or serum. Standard EUSA or other immunoassay can be used to assess the levels of antibodies. Following immunization, antisera can be obtained and, if desired, polyclonal antibodies isolated from the sera.

To produce monoclonal antibodies, antibody producing calls (lymphocytes) can be harvested from an immunized animal and fused with myeloma cells by standard somatic cell fusion procedures, thus immortalizing these cells and yielding hybridoma cells. Such techniques are well known in the art. For example, the hybridoma technique originally developed by Kohler and Milstein [Kohler, 1975] as well as other techniques such as the human B-cell hybridoma technique [Kozbor, 1983], the EBV-hybridoma technique to produce human monoclonal antibodies [Cole, 1985], and screening of combinatorial antibody libraries [Huse, 1989]. Hybridoma cells can be screened immunochemically for production of antibodies specifically reactive with the peptide, and monoclonal antibodies isolated.

The term antibody as used herein is intended to include fragments thereof which are also specifically reactive with a protein having the biological activity of P450RAI, or a peptide fragment thereof. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments.

It is also known in the art to make chimeric antibody molecules with human constant regions. See, for example, Morrison et al., Takeda et al., Cabilly et al., Boss et al., Tanaguchi et al., Teng et al. [Morrison, 1985; Takeda, 1985; Cabilly; Boss; Tanaguchi; Teng, 1982], European Patent Publication 0173494, United Kingdom Patent GB 2177096B, PCT Publication WO92/06193 and EP 0239400. It is expected that such chimeric antibodies would be less immunogenic in a human subject than the corresponding non-chimeric antibody.

Another method of generating specific antibodies, or antibody fragments, reactive against protein having the biological activity of a P450RAI, or a peptide fragment thereof, is to screen expression libraries encoding immunoglobulin genes, or portions thereof, expressed in bacteria, with peptides produced from the nucleic acid molecules of the present invention. For example, complete Fab fragments, VH regions and FV regions can be expressed in bacteria using phage expression libraries. See for example Ward et al., Huse et al., and McCafferty et al. [Ward, 1989; Huse, 1989; McCafferty, 1990]. Screening such libraries with, for example, a P450RAI peptide can identify immunoglobulin fragments reactive with P450RAI. Alternatively, the SCID-hu mouse developed by Genpharm can be used to produce antibodies, or fragments thereof.

The polyclonal, monoclonal or chimeric monoclonal antibodies can be used to detect the proteins of the invention, portions thereof or closely related isoforms in various biological materials, for example they can be used in an ELISA, radioimmunoassay or histochemical tests. Thus, the antibodies can be used to quantify the amount of a P450RAI protein of the invention, portions thereof or closely related isoforms in a sample in order to determine the role of P450RAI proteins in particular cellular events or pathological states. Using methods described herein before, polyclonal, monoclonal antibodies, or chimeric monoclonal antibodies can be raised to nonconserved regions of P450RAI and used to distinguish a particular P450RAI from other proteins.

The polyclonal or monoclonal antibodies can be coupled to a detectable substance or reporter system. The term "coupled" is used to mean that the detectable substance is physically linked to the antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; and examples of suitable radioactive material include $^{125}$I; $^{131}$I, $^{35}$S and $^3$H. In a preferred embodiment, the reporter system allows quantitation of the amount of protein (antigen) present Such an antibody-linked reporter system could be used in a method for determining whether a fluid or tissue sample of a subject contains a deficient amount or an excessive amount of the protein. Given a normal threshold concentration of such a protein for a given type of subject, test kits could thus be developed.

The present invention allows the skilled artisan to prepare bispecific antibodies and tetrameric antibody complexes. Bispecific antibodies can be prepared by forming hybrid hybridomas [Staerz, 1986a & b].

The present invention includes three types of compounds related to retinoids: those that inhibit enzymatic activity of P450RAI, thereby inhibiting metabolism of RA; those retinoids that evade metabolism by P450RAI, for example Am580, shown above; and those compounds that repress induction of P450RAI gene expression, for example 4-HPR, as shown above.

Compositions of the invention are administered to subjects in a biologically compatible form suitable for pharmaceutical administration in vivo. By "biologically compatible from suitable for administration in vivo" is meant a form of the composition to be administered In which any toxic effects are outweighed by the therapeutic effects of the composition. The term "subject" is intended to include living organisms in which a desired therapeutic response can be elicited, e.g. mammals. Examples of subjects include human, dogs, cats, mice, rats and transgenic species thereof. Administration of a therapeutically active amount of the therapeutic compositions of the present invention is defined as an amount effective, at dosages and for periods of time necessary to achieve the desired result. For example, a therapeutically active amount of a compound that inhibits catabolism of RA by a P450RAI protein may vary according to factors such as the disease state, age, sex, and weight of the individual, as well as target tissue and mode of delivery. Dosage regimes may be adjusted to provide the optimum therapeutic response. For example, several divided doses may be administered daily or the dose may be proportionally reduced as indicated by the exigencies of the therapeutic situation.

Compounds of the present invention, such as those that are found to inhibit metabolism of RA by P450RAI enzymes and that are useful as anticancer agents and in the treatment, amelioration, or prevention of skin disorders for which retinoic acid is useful, for example, may be used topically. In this regard they may be included in compositions for therapy in animals, including humans, for premalignant epithelial cell lesions, as a prophylaxis against tumor promotion in epithelial cells and treatment for dermatoses such as ichthyoses, follicular disorders, benign epithelial disorders, and other proliferative skin diseases, such as acne, psoriasis, eczema, atopic dermatitis, nonspecific dermatitis and the like.

Topical compositions are usually formulated with a pharmaceutically acceptable carrier in liquid, semisolid or solid form. A pharmaceutically acceptable carrier is a material that is nontoxic and generally inert and does not affect the functionality of the active ingredients adversely. Such materials are well known and include those materials sometimes referred to as diluents or vehicles (excipients) in the pharmaceutical formulation art The carrier may be organic or inorganic in nature. Examples of pharmaceutically acceptable carriers are water, gelatin, lactose, starch, mineral oil, cocoa butter, dextrose, sucrose, sorbitol, mannitol, gum, acacia, alginates, cellulose, talc, magnesium stearate, polyoxyethylene sorbitan monolaurate, and other commonly used pharmaceutical carriers. In addition to an active ingredient and carrier, the formulation may contain minor amounts of additives such as flavoring agents, coloring agents, thickening or gelling agents, emulsifiers, wetting agents, buffers, stabilizers, and preservatives such as antioxidants.

Certain compositions may be administered enterally. For oral administration, suitable forms are, for example, tablets, pills, syrups, suspensions, emulsions, solutions, powders and granules.

As anti-tumor agents or as part of an anti-tumor formulation, for example, compounds of the present invention can be used in a similar manner to retinoids used for treating various tumours, such as all-trans retinoic acid. The dose to be administered, whether a single dose, multiple does or daily dose, will of course vary with the particular compound employed because of the varying potency of the active ingredient, the chosen route of administration, the size of the recipient, the type of tumor, and the nature of the patent's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. An oncologist skilled in the art of cancer treatment will be able to ascertain without undue experimentation, appropriate protocols for the effective administration of the compounds of this present invention.

Nucleic acids which encode proteins having biological activity of a P450RAI protein can be used to generate either transgenic animals or knock out animals which, in turn, are useful in the development and screening of therapeutically useful reagents. A transgenic animal (e.g., a mouse) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, a human P450RAI cDNA, comprising the nucleotide sequence shown in SEQ ID NO:5, or an appropriate variant or subsequence thereof, can be used to generate transgenic animals that contain cells which express human P450RAI protein. Methods for generating transgenic animals, particularly animals such as mice, have become conventional in the art are described, for example, in U.S. Pat. Nos. 4,736,866 and 4,870,009. In a preferred embodiment, plasmids containing recombinant molecules of the invention are microinjected into mouse embryos. In particular, the plasmids are microinjected into the male pronuclei of fertilized one-cell mouse eggs; the injected eggs are transferred to pseudopregnant foster females; and, the eggs in the foster females are allowed to develop to term. [Hogan, 1986]. Alternatively, an embryonal stem cell line can be transfected with an expression vector comprising nucleic acid encoding a protein having P450RAI activity, and cells containing the nucleic acid can be used to form aggregation chimeras with embryos from a suitable recipient mouse strain. The chimeric embryos can then be implanted into a suitable pseudopregnant female mouse of the appropriate strain and the embryo brought to term. Progeny harboring the transfected DNA in their germ cells can be used to breed uniformly transgenic mice.

Typically, particular cells would be targeted for P450RAI transgene incorporation by use of tissue specific enhancers operatively linked to the P450RAI encoding gene. For example, promoters and/or enhancers which direct expression of a gene to which they are operatively linked preferentially in cardiac muscle cells can be used to create a transgenic animal which expresses a P450RAI protein preferentially in cardiac muscle tissue. Examples of suitable promoters and enhancers include those which regulate the expression of the genes for cardiac myosin and cardiac actin. Transgenic animals that include a copy of an P450RAI transgene introduced into the germ line of the animal at an embryonic stage can also be used to examine the effect of increased P450RAI expression in various tissues.

The pattern and extent of expression of a recombinant molecule of the invention in a transgenic mouse is facilitated by fusing a reporter gene to the recombinant molecule such that both genes are co-transcribed to form a polycistronic mRNA. The reporter gene can be introduced into the recombinant molecule using conventional methods such as those described in Sambrook et al., [Sambrook, 1989]. Efficient expression of both cistrons of the polycistronic mRNA encoding the protein of the invention and the reporter protein can be achieved by inclusion of a known internal translational initiation sequence such as that present in poliovirus mRNA. The reporter gene should be under the control of the regulatory sequence of the recombinant molecule of the invention and the pattern and extent of expression of the gene encoding a protein of the invention can accordingly be determined by assaying for the phenotype of the reporter gene. Preferably the reporter gene codes for a phenotype not displayed by the host cell and the phenotype can be assayed quantitatively. Examples of suitable reporter genes include lacZ (β-galactosidase), neo (neomycin phosphotransferase), CAT (chloramphenicol acetyltransferase) dhfr (dihydrofolate reductase), aphIV (hygromycin phosphotransferase), lux (luciferase), uidA (β-glucuronidase). Preferably, the reporter gene is lacZ which codes for β-galactosidase. β-galactosidase can be assayed using the lactose analogue X-gal (5-bromo-4-chloro-3-indolyl-D-galactopyranoside) which is broken down by β-galactosidase to a product that is blue in color [Old].

Although experimental animals used in the preferred embodiment disclosed are mice, the invention should not be limited thereto. It can be desirable to use other species such as, for example, rats, hamsters, rabbits and sheep.

The transgenic animals of the invention can be used to investigate the molecular basis of RA metabolism. The transgenic animals of the invention can also be used to test substances for the ability to prevent, slow or enhance RA metabolism. A transgenic animal can be treated with the substance in parallel with an untreated control transgenic animal.

Cells from the transgenic animals of the invention can be cultured using standard tissue culture techniques. In particular, cells carrying the recombinant molecule of the invention can be cultured and used to test substances for the ability to prevent, slow or enhance RA metabolism.

Additionally, the nonhuman homologues of genes encoding proteins having P450RAI activity can be used to construct a "knock out" animal which has a defective or altered P450RAI gene. For example, with established techniques, a portion of murine genomic P450RAI DNA (e.g., an exon), can be deleted or replaced with another gene, such as a gene encoding a selectable marker which can be used to monitor integration. The altered P450RAI DNA can then be transfected into an embryonal stem cell line. The altered P450RAI DNA will homologously recombine with the endogenous P450RAI gene in certain cells and clones containing the altered gene can be selected. Cells containing the altered gene are injected into a blastocyst of an animal, such as a mouse, to form aggregation chimeras as described for transgenic animals. Chimeric embryos are implanted as described above. Transmission of the altered gene into the germline of a resultant animal can be confirmed using standard techniques and the animal can be used to breed animals having an altered P450RAI gene in every cell [Lemoine, 1996]. Accordingly, a knockout animal can be made which cannot express a functional P450RAI protein. Such a knockout animal can be used, for example, to test the effectiveness of an agent in the absence of a P450RAI protein.

The antisense nucleic acids and oligonucleotides of the invention are useful for inhibiting expression of nucleic adds (e.g. mRNAs) encoding proteins having P450RAI activity. Since proteins having P450RAI activity are associated with metabolism of agents which can act on the cell, e.g., RA, decreasing expression of such proteins can increase sensitivity of the cell to such agents. Antisense nucleic acids can be introduced into a drug resistant cell in culture to inhibit P450RAI expression. One or more antisense nucleic acids, such as oligonucleotides, can be added to cells in culture media, typically, for example, at 200 μg/ml.

The antisense nucleic acids of the invention, or oligonucleotides thereof, can thus be used in gene therapy to correct or prevent retinoic acid or other retinoid resistance in a subject For example, antisense sequences can be used to render retinoic acid or other retinoid resistant malignant cells sensitive to chemotherapeutic agents. Administration of antisense nucleic acids to a subject may be most effective when the antisense nucleic acid is contained in a recombinant expression vector which allows for continuous production of antisense RNA. Recombinant molecules comprising an antisense nucleic acid or oligonucleotide thereof, can be directly introduced into tissues, including lung tissue in vivo, using delivery vehicles such as liposomes, retroviral vectors, adenoviral vectors and DNA virus vectors. A delivery vehicle can be chosen which can be targeted to a cell of interest in the subject (e.g. a retinoid resistant tumor cell). Antisense nucleic acids can also be introduced into isolated cells, such as those of the haematopoietic system, ex vivo using viral vectors or physical techniques such as microinjection and electroporation or chemical methods such as coprecipitation and incorporation of DNA into liposomes, and such cells can be returned to the donor. Recombinant molecules can be delivered in the form of an aerosol or by lavage.

Accordingly, the invention provides a method for inhibiting retinoic add or other retinoid resistance of a resistant cell by introducing into the resistant cell a nucleic acid which is antisense to a nucleic acid which encodes the protein identified as SEQ ID NO:2, SEQ ID NO:32, or particularly, the in case of human cells SEQ ID NO:4.

The nucleic acids of the invention can further be used to design ribozymes which are capable of cleaving a single-stranded nucleic acid encoding a protein having P450RAI activity, such as an mRNA. A catalytic RNA (ribozyme) having ribonuclease activity can be designed which has specificity for a P450RAI-encoding mRNA based upon the sequence of a nucleic acid of the invention. For example, a derivative of a Tetrahymena L-19IVS RNA can be constructed in which the base sequence of the active site is complementary to the base sequence to be cleaved in a P450RAI-encoding mRNA. [Cech a and b]. Alternatively, a nucleic acid of the invention could be used to select a catalytic RNA having a specific ribonuclease activity from a pool of RNA molecules [Bartel, 1993].

The isolated nucleic acids and antisense nucleic acids of the invention can be used to construct recombinant expression vectors as described previously. These recombinant expression vectors are then useful for making transformant host cells containing the recombinant expression vectors, for expressing protein encoded by the nucleic acids of the invention, and for isolating proteins of the invention as described previously. The isolated nucleic acids and antisense nucleic acids of the invention can also be used to construct transgenic and knockout animals as described previously.

The isolated proteins of the invention are useful for making antibodies reactive against proteins having P450RAI activity, as described previously. Alternatively, the antibodies of the invention can be used to isolate a protein of the invention by standard immunoaffinity techniques. Furthermore, the antibodies of the invention, including bispecific antibodies are useful for diagnostic purposes.

Molecules which bind to a protein comprising an amino acid sequence shown in SEQ ID NO:4 can also be used in a method for killing a cell which expresses the protein, wherein the cell takes up the molecule. Preferably, the cell is a tumor cell. Destruction of such cells can be accomplished by labeling the molecule with a substance having toxic or therapeutic activity. The term "substance having toxic or therapeutic activity" as used herein is intended to include molecules whose action can destroy a cell, such as a radioactive isotope, a toxin (e.g. diphtheria toxin or ricin), or a chemotherapeutic drug, as well as cells whose action can destroy a cell, such as a cytotoxic cell. The molecule binding to the P450RAI can be directly coupled to a substance having a toxic or therapeutic activity or may be indirectly linked to the substance. In one example, the toxicity of the molecule taken up by the cell is activated by P450RAI protein.

The invention also provides a diagnostic kit for identifying tumor cells comprising a molecule which binds to a protein comprising an amino acid sequence shown in SEQ ID NO:4, for example, for incubation with a sample of tumor cells; means for detecting the molecule bound to the protein, unreacted protein or unbound molecule; means for determining the amount of protein in the sample; and means for comparing the amount of protein in the sample with a standard. Preferably, the molecule is a monoclonal antibody. In some embodiments of the invention, the detectability of the molecule which binds to P450RAI is activated by said binding (e.g., change in fluorescence spectrum, loss of radioisotopic label). The diagnostic kit can also contain an instruction manual for use of the kit.

The invention further provides a diagnostic kit for identifying tumor cells comprising a nucleotide probe complementary to the sequence, or an oligonucleotide fragment thereof, shown in SEQ ID NO:3, for example, for hybridization with mRNA from a sample of tumor cells; means for detecting the nucleotide probe bound to mRNA in the sample with a standard. The diagnostic kit can also contain an instruction manual for use of the kit.

Those skilled in the art will know, or be able to ascertain using no more than routine experimentation, many equivalents to the specific embodiments of the invention described herein. Such equivalents are intended to be encompassed by the following claims.

References

Particulars of references cited above are given below. All of the listed references are incorporated herein by reference.

Adamson, P. C., Boylan, J. F., Balls, F. M., Murphy, R. F., Godwin, K. A., Gudas, L. J. and Poplack, D. G. (1993). Time course of induction of metabolism of all-trans retinoic acid and the up-regulation of cellular retinoic acid-binding protein. Cancer Research 53, 472–476.

Achkar, C. C., Derguini, F., Blumberg, B., Langston, A., Arthur, A. L., Speck, J., Evans, R. M., Bolado, Jr., J. Nakanishi, K. and Buck, J. (1996) 4-Oxoreinol, a new natural ligand and transactivator of the retinoic acid receptors. Proc. Natl. Acad. Sci. USA 93, 4879–84.

Akimenko, M. A. and Ekker, M. (1995a). Anterior duplication of the Sonic hedgehog expression pattern in the pectoral fin buds of zebrafish treated with retinoic acid. Developmental Biology 170, 243–7.

Akimenko, M. A., Johnson, S. L., Westerfield, M. and Ekker, M. (1995b). Differential induction of four msx homeobox genes during fin development and regeneration in zebrafish. Development 121, 347–57.

Akiyoshi-Shibata, M., Sakaki, T., Ohyama, Y., Noshiro, M., Okuda, K. and Yabusaki, Y. (1994). Further oxidation of hydroxycalcidiol by calcidiol 24-hydroxylase. A study with the mature enzyme expressed in *Escherichia coli*. European Journal of Biochemistry 224, 335–43.

Bartel, D. and Szostak, J. W. (1993). Science 261, 1411–1418.

Blaner, W. (1994). Retinol and retinoic acid metabolism. In: The Retinoids. (M. Sporn, Roberts, A and Goodman, D. S., Editors) Raven Press, inc.: New York.

Bligh, E. G. and Dyer, W. J. (1957). A rapid method of total lipid extraction and purification. Canadian Journal of Biochemistry 37, 911–917.

Blumberg, B., Bolado, Jr., J., Derguini, F., Craig, A. G., Moreno, T. A., Chakravarti, D., Heyman, R. A., Buck, J. and Evans, R. M. (1996) Novel retinoic acid receptor ligands in Xenopus embryos. Proc. Natl. Acad. Sci. USA 93, 4873–78.

Boss et al., U.S. Pat. No. 4,816,397.

Boylan, J. F., Lufkin, T., Achkar, C. C., Taneha, R., Chambon, P. and Gudas, L. J. (1995). Targeted Disruption of Retinoic Acid Receptor a (RARa) and RARg Results in Receptor-Specific Alterations in Retinoic Acid-Mediated Differentiation and Retinoic Acid Metabolism. Mol. Cell Biol. 15, 843–851.

Boyle, A. L. et al. (1992). Genomics 12, 106–15.

Cabilly et al. U.S. Pat. No. 4,816,567.

Cech et al., (a) U.S. Pat. No. 4,987,071.

Cech et al., (b) U.S. Pat. No. 5,116,742.

Chambon, P. (1995). The molecular and genetic dissection of the retinoid signaling pathway. [Review]. Recent Progress in Hormone Research 50, 317–32.

Chen, K. S. and DeLuca, H. F. (1995). Cloning of the human 1 alpha,25-dihydroxyvitamin D-3 24-hydroxylase gene promoter and identification of two vitamin D-responsive elements. Biochimica et Biophysica Acta 1263, 1–9.

Chomienne, C., Fenaux and Degos, L. (1996). Retinoid differentiation therapy in promyelocytic leukemia. FASEB J. 1025–1030.

Chytil, F. (1984). Retinoic acid: Biochemistry, toxicology, pharmacology, and therapeutic use. Pharmacol. Rev. 36, 93–99.

Cole et al. (1985). Monoclonal Antibodies in Cancer Therapy. Allen R. Bliss, inc.

Costaridis, P., Horton, C., Zeitlinger, J., Holder, N. and Maden, M. (1996). Endogenous Retinoids in the Zebrafish Embryo and Adult. Developmental Dynamics 205, 41–51.

Creech Kraft, J., Schuh, T., Juchau, M. R. and Kimelman, D. (1994). Temporal distribution, localization and metabolism of all-trans retinol, didehydroretinol and all-trans retinal during Xenopus development Biochem. J. 301, 111–119.

De Coster, R., Wouters, W. and Bruynseels, J. (1996). P450-dependent enzymes as targets for prostate cancer therapy. J. Ster. Biochem. Mol. Biol. 56, 133–43.

Duell, E. A, Astrom, A., Griffiths, C. E., Chambon, P. and Voorhees, J. J. (1992). Human skin levels of retinoic acid and cytochrome p-450-derived 4-hydroxyretinoic acid after topical application of retinoic acid in vivo compared to concentrations required to stimulate retinoic acid receptor-mediated transcription in vitro. Journal of Clinical investigation 90, 1269–74.

Duell, E. A., Astrom, A., Kang, S., Griffiths, C. E. M. and Voorhees, J. (1994). All-trans, 9-cis and 13-cis retinoic acid each induce a cytochrome P450 4-retinoic add hydroxylase which causes all-trans but not 9-cis or 13-cis retinoic acid to self-metabolize. Society for investigative Dermatology Abstracts 102, 641.

Fiorella, P. D., Giguere, V. and Napoli, J. L. (1993). Expression of Cellular Retinoic Acid-binding Protein (Type II) in *Escherichia coli*. The Journal of Biological Chemistry 268, 21545–21552.

Formelli, F., Barua, A. and Olson, J. (1996). Bioactivities of N-(4-hydroxyphenyl) retinimide and retinoyl B-glucuronide. FASEB J. 10, 1014–1024.

Frolik, C. A, Roberts, A. B., Tavela, T. E., Roller, P. P., Newton, D. L. and Sporn, M. B. (1979). Isolation and identification of 4-hydroxy- and 4-oxoretinoic acid. In vitro metabolites of all-trans retinoic acid in hamster trachea and liver. Biochemistry 18, 2092–7.

Gotoh, O. and Fujii-Kuriyama, Y. (1989). Evolution, structure, and gene regulation of cytochrome P450.

Green, S., Issemenn, I. and Sheer, E. (1988). A versatile in vivo and in vitro eukaryotic expression vector for protein engineering. Nucleic Acids Research 16, 369–370.

Gudas, L, Sporn, M. and Roberts, A. (1994). Cellular biology and biochemistry of the retinoids. In: The Retinoids. (M. Sporn, Roberts, A. and Goodman, D. S., Editors) Raven Press, inc.: New York.

Heng, H. and Tsui, L.-C. (1993). Chromosome 102, 325–32.

Hogan, B. et al., (1986). A Laboratory Manual, Cold Spring Harbor, N.Y., Cold Spring Harbor Laboratory.

Hong, W. (1994). Retinoids and human cancer. In: The Retinoids. (M. Sporn, Roberts, A. and Goodman, D. S., Editors) Raven Press, inc.: New York.

Houbenwcyl, (1987). Methods of Organic Chemistry, ed. E. Wansch. Vol.15 I and II. Thieme, Stuttgart.

Hozumi, N and Sandhu, J. S. (1993). Recombinant antibody technology, its advent and advances. Cancer invest. 11, 714–723.

Huse et al., (1989). Science 246, 1275–1281.

Jones, B. B., Ohno, C. K, Allenby, G., Boffa, M., Levin, A. A., Grippo, J. F. and Petkovich, M. (1995). New Retinoid X Receptor Subtypes in Zebra Fish (*Danio rerio*) Differentially Modulate Transcription and Do Not Bind 9-cis Retinoic Acid. Mol. Cell Biol. 15, 5226–5234.

Kennett, R. (1979). Cell fusion. Methods Enzymol. 58, 345–359.

Kohler and Milstein. (1975). Nature 256, 495–497.

Kozbor et al. (1983). Immunol. Today 4, 72.

Lammer, E. J., Chen, D. T., Hoar, R. M., Agnish, N. D., Benke, P. J., Braun, J. T., Curry, C. J., Fernhoff, P. M., Grix, A J., Lott, I. T. et al. (1985). Retinoic acid embryopathy. New England Journal of Medicine 313, 837–41.

Lansdorp, U.S. Pat. No. 4,866,109.

Lemoine, N. R. and Cooper, D. N. (1996). Gene Therapy, Human Molecular Genetics Series, BIOS Scientific Publishers, Oxford, U.K.

Leo et al. (1989). Metabolism of retinol and retinoic acid by human liver cytochrome P450IIC8. Arch. Biochem. Biophys. 269, 305–312.

Liang, P. and Pardee, A. B. (1992). Differential display of eukaryotic messenger RNA by means of the polymerase chain reaction. Science 257, 967–71.

Lichter, P. et al. (1990). High Resolution Mapping of Chromosome 11 by in situ hybridization by cosmid clones. Science 247, 64–9.

Lippman, S. M., Heyman, R. A., Kurie, J. M., Benner, S. E. and Hong, W. K. (1995). Retinoids and chemoprevention:

clinical and basic studies. J. Cellular Biochem. Supplement 22,1–10.

Lotan, R. M. (1995). Squamous differentiation and retinoids. Cancer Treat. Res. 74, 43–72.

Lotan, R. (1996). Retinoids in Cancer Chemoprevention. Faseb J. 10, 1031–1039.

Maden, M. and Holder, N. (1992). Retinoic acid and development of the central nervous system. [Review]. Bioessays 14, 431–8.

Makin, G., Lohnes, D., Byford, V., Ray, R. and Jones, G. (1989). Target cell metabolism of 1,25-dihydroxyvitamin D3 to calcitroic add. Evidence for a pathway in kidney and bone involving 24-oxidation. Biochemical Journal 262, 173–80.

Maniatis et al. (1982) Molecular Cloning: A Laboratory Manual, Cold Spring Harbor Laboratory Press, Cold Spring Harbor, N.Y.

Mangelsdorf, D. J. and Evans, R. M. (1995). The RXR Heterodimers and Orphan Receptors. Cell 83, 841–850.

Merrifield, (1984). J. Am. Chem. Assoc. 85, 2149–2154.

McCafferty et al., (1990). Nature 348, 552–554.

Mirski, S. and Cole, S. P. C. (1989). Antigens associated with multidrug resistance in H69AR, a small cell lung cancer cell line. Cancer Res. 49, 5719–5724.

Monia, B. P., Johnston, J. F., Geiger, T., Muller, M. and Fabbro, D. (1996). Antitumor activity of a phosphorothioate antisense oligodeoxynuclieotide targeted against C-raf kinase. Nature Medicine 2, 668–75.

Moon, R. C., Mehta, R. G. and Rao, K. V. N. (1994). Retinoids and cancer in experimental animals. In: The Retinoids. (M. Sporn, Roberts, A. and Goodman, D. S., Editors) Raven Press, Inc.: New York.

Morriss-Kay, G. (1993). Retinoic acid and craniofacial development molecules and morphogenesis. [Review]. Bioessays 15, 9–15.

Morris-Kay, G. M. (1996). Embryonic development and pattern formation. FASEB J. 10, 961–968.

Morrison et al., (1985). Proc. Natl. Acad. Sci. USA 81, 6851.

Muindi, J. R. F., Frankel, S. R., Huselton, C., DeGrazia, F., Garland, W., Young, C. W. and Warrell, R. P., Jr. (1992). Clinical pharmacology of oral all-trans retinoic acid in patients with acute promyelocytic leukemia. Cancer Research 52, 2138–2142.

Muindi, J. R., Young, C. W. and Warrell, R. J. (1994a). Clinical pharmacology of all-trans retinoic acid. Leukemia 8, 1807–1812.

Muindi, J. R., Young, C. W. and Warrell, R. J. (1994b). Clinical pharmacology of all-trans retinoic acid. Leukemia 8, s16–s21.

Napoli, J. L., Boerman, M. H., Chai, X., Zhai, Y. and Fiorella, P. D. (1995). Enzymes and binding proteins affecting retinoic acid concentrations. J. Ster. Biochem. Mol. Biol. 53, 497–502.

Napoli, J. (1996). Retinoic add biosynthesis and metabolism. FASEB J. 10, 993–1001.

Nelson, D. R., Kamataki, T., Waxman, D. J., Guengerich, F. P., Estabrook, R. W., Feyereisen, R., Gonzalez, F. J., Coon, M. J., Gunsalus, i. C., Gotoh, O., Okuda, K. and Nebert, D. W. (1993). The P450 superfamily: update on new sequences, gene mapping, accession numbers, early trivial names of enzymes, and nomenclature. DNA & Cell Biology 12, 1–51.

Old, R. W. and Primrose, S. B., in: Principles of Gene Manipulation. An introduction to Genetic Engineering, 4th ad. Oxford University Press. 63–66.

Ohno, C. K. and Petkovich, M. (1993). FTZ-F1 beta, a novel member of the Drosophile nuclear receptor family. Mechanisms of Development 40, 13–24.

Ohno, C. K., Ueda, H. and Petkovich, M. (1994). The Drosophila nuclear receptors FTZ-F1 alpha and FTZ-F1 beta compete as monomers for binding to a site in the fushi tarazu gene. Mol. Cell Biol. 14, 3166–75.

Ohyama, Y., Ozono, K., Uchida, M., Shinki, T., Kato, S., Suda, T., Yamamoto, O., Noshiro, M. and Kato, Y. (1994). Identification of a vitamin D-responsive element in the 5'-flanking region of the rat 25-hydroxyvitamin D3 24-hydroxytase gene. Journal of Biological Chemistry 269, 10545–50.

Petkovich, M., Brand, N. J., Krust, A. and Chambon, P. (1987). A human retinoic acid receptor which belongs to the family of nuclear receptors. Nature 330, 444–50.

Pijnappel, W. W., Hendriks, H. F., Folkers, G. E., van den Brink, C., Dekker, E. J., Edelenbosch, C., van der Saag, P. and Durston, A. J. (1993). The retinoid ligand 4-oxo-retinoic acid is a highly active modulator of positional specification. Nature 366, 340–4.

Reddy, A. P., Chen, J., Zacharewski, T., Gronemeyer, H., Voorhees, J. J. and Fisher, G. J. (1992). Characterization and purification of human retinoic acid receptor-g1 overexpressed in the baculovirus-insect cell system. Biochem. J. 287, 833–840.

Rigas, J., Miller, V., Zhang, L. F., Kilmstra, D., Tong, W., Kris, M. and Warrell, R. (1996). Metabolic phenotypes of retinoic acid and the risk of lung cancer. Cancer Res. 56, 2692–2696.

Roberts, A. B., Nichols, M. D., Newton, D. L. and Sporn, M. B. (1979a). In vitro metabolism of retinoic acid in hamster intestine and liver. Journal of Biological Chemistry 254, 6296–302.

Roberts, A. B., Frolik, C. A., Nichols, M. D. and Sporn, M. B. (1979b). Retinoid-dependent Induction of the in vivo and in vitro metabolism of retinoic acid in tissues of the vitamin A-deficient hamster. Journal of Biological Chemistry 254, 6303–9.

Sambrook, J., Fritsch E. F. and Maniatis, T. (1989). Molecular Cloning: A Laboratory Manual. Cold Spring Harbor Lab Press, Cold Spring Harbor, N.Y.

Staerz & Bevan (1986a). Proc. Natl. Acad. Sci. (USA) 83, 1453.

Staerz & Bevan (1986b). Immunology Today 7, 241.

Stewart, A. J., Canitrot, Y., Baracchini, E., Dean, N. M., Deeley, R. G., and Cole, S. P. C. (1996). Reduction of Expression of the multidrug resistance protein (MRP) in human tumor cells by antisense phophorothioate oligonucleotides. Biochem. Pharamcol. 51, 461–469.

Taimi, M. and Breitman, T. R. (1997). N-4-hydroxyphenylretinamide enhances retinoic acid-induced differentiation and retinoylation of proteins in the human acute promyelocytic leukemia cell line, NB4, by a mechanism that may involve inhibition of retinoic acid catabolism. Biochemical and Biophysical Research Communications 232, 432–435.

Takatsuka, J., Takahashi, N. and De Luca, L. M. (1996). Retinoic Acid Metabolism and Inhibition of Cell Proliferation: An Unexpected Liaison. Cancer Research 56, 675–678.

Takeda et al.,(1985). Nature 314, 452.

Tanaguchi et al., European Patent Publication EP171496.

Teng, et al. (1982) Math. Enzymol. 92, 3–16.

Thaller, C. and Eichele, G. (1990). Isolation of 3,4-didehydroretinoic acid, a novel morphogenetic signal in the chick wing bud. Nature 345, 815–9.

Van Wauwe, J. P., Coene, M.-C., Goossens, J., Van Nijen, G., Cools, W. and Lauwers, W. (1988). Ketoconazole inhibits the in vitro and in vivo metabolism of all-trans retinoic acid. The Journal of Pharmacology and Experimental Therapeutics 245, 718–722.

Van Wauwe, J. P., Coene, M.-C., Goossens, J., Cools, W. and Monbaliu, J. (1990). Effects of cytochrome P450 inhibitors on the in viva metabolism of all-trans-retinoic acid in rats. The Journal of Pharmacology and Experimental Therapeutics 252, 365–369.

Van Wauwe, J., Van Nyen, G., Coene, M., Stoppie, P., Cools, W., Goossens, J., Borghgraef, P. and Janssen, P. A. J. (1992). Liarazole, an inhibitor of Retinoic Acid Metabolism, Exerts Retinoid-Mimetic Effects in Vivo. The Journal of Pharmacology and Experimental Therapeutics 261, 773–779.

Ward et al., (1989). Nature 341, 544–546.

Warrell, R. J. (1994). Applications for retinoids in cancer therapy. Seminars in Hematol. 31, 1–13.

Warrell, R. J., Maslak, P., Eardley, A., Heller, G., Miller, W. J. and Frankel, S. R. (1994). Treatment of acute promyelocytic leukemia with all-trans retinoic acid: an update of the New York experience. Leukemia 8, 929–933.

White, J. A., Boffa, M. B., Jones, B. and Petkovich, M. (1994). A zebrafish retinoic acid receptor expressed in the regenerating caudal fin. Development 120, 1861–72.

Williams, J. B. and Napoli, J. L. (1987). Inhibition of retinoic acid metabolism by imidazole antimycotics in F9 embryonal carcinoma cells. Biochemical Pharmacology 36, 1386–1388.

Wilson, G. M. and Deeley, R. G. (1995). An episomal expression vector system for monitoring sequence-specific effects on mRNA stability in human cell lines. Plasmid 33, 198–207.

Windhorst, D. B. (1982). The use of isotretinoin in disorders of keratinization. Journal of the American Academy of Dermatology 6, 7089.

Wouters, W., van, D. J., Dillen, A., Coene, M. C., Cools, W. and De, C. R. (1992). Effects of liarazole, a new antitumoral compound, on retinoic acid-induced inhibition of cell growth and on retinoic acid metabolism in MCF-7 human breast cancer cells. Cancer Research 52, 2841–6.

Zierold, C., Darwish, H. M. and DeLuca, H. F. (1995). Two vitamin D response elements function in the rat 1,25-dihydroxyvitamin D 24-hydroxylase promoter. Journal of Biological Chemistry 270, 16756–8.

What is claimed is:

1. A microsomal preparation of a cell that has been transfected with a nucleic acid molecule encoding a protein, or of a desendent cell thereof, wherein said protein oxidizes all-trans retinoic acid at the C4-position of the β-ionone ring, said nucleic acid molecule comprising a nucleic acid sequence that hybridizes under high strigency conditions, wherein high stringency conditions include a wash step of about 0.2×SCC at 65° C., to a polynucleotide having a nucleotide sequence shown as SEQ ID NO:3, said microsomal preparation comprising said protein.

2. A microsomal preparation of a cell that has been transfected with a nucleic acid molecule encoding a protein, or of a desendent cell thereof, wherein said protein hydroxylates all-trans retinoic acid at the C4-position of the β-ionone ring, said nucleic acid molecule comprising a nucleotide sequence that hybridizes under high strigency conditions, wherein high stringency conditions include a wash step of about 0.2×SCC at 65° C., to a nucleic acid molecule having a nucleotide sequence shown as SEQ ID NO:3, said microsomal preparation comprising said protein.

3. The preparation of claim 1, wherein the protein comprises the amino acid sequence identified as SEQ ID NO:2.

4. The preparation of claim 1, wherein the nucleic acid molecule encodes an amino acid sequence that is at least 95 percent conserved with respect to SEQ ID NO:2.

5. The preparation of claim 1, wherein the protein additionally hydroxylates the C18-position of all-trans retinoic acid.

6. The preparation of claim 2, wherein the nucleic acid molecule encodes an amino acid sequence that is at least 95 percent conserved with respect to SEQ ID NO:2.

7. The preparation of claim 2, wherein the protein additionally hydroxylates the C18-position of all-trans retinoic acid.

8. A microsomal preparation of a cell that has been transfected with a nucleic acid molecule encoding a protein, or of a desendent cell thereof, wherein said protein oxidizes all-trans retinoic acid at the C4-position of the β-ionone ring, said nucleic acid molecule encoding an amino acid sequence that is at least 95 percent conserved with respect to SEQ ID NO:2, said microsomal preparation comprising said protein.

9. The preparation of claim 8, wherein the protein additionally hydroxylates the C18-position of all-trans retinoic acid.

10. A microsomal preparation of a cell that has been transfected with a nucleic acid molecule encoding a protein, or of a desendent cell thereof, wherein said protein hydroxylates all-trans retinoic acid at the C4-position of the β-ionone ring, said nucleic acid molecule encoding an amino acid sequence that is at least 95 percent conserved with respect to SEQ ID NO:2, said microsomal preparation comprising said protein.

11. The preparation of claim 10, wherein the protein additionally hydroxylates the C18-position of all-trans retinoic acid.

* * * * *